(12) United States Patent
Allerheiligen et al.

(10) Patent No.: US 8,198,267 B2
(45) Date of Patent: Jun. 12, 2012

(54) SUBSTITUTED OXAZOLIDINONES AND THEIR USE

(75) Inventors: Swen Allerheiligen, Essen (DE);
Marcus Bauser, Berlin (DE); Hartmut Schirok, Langenfeld (DE); Michael Härter, Leverkusen (DE); Stephan Siegel, Berlin (DE); Ulrich Rester, Wuppertal (DE); Christoph Gerdes, Köln (DE); Stefan Heitmeier, Wülfrath (DE); Georges Von Degenfeld, Leverkusen (DE); Anja Buchmüller, Essen (DE); Elke Dittrich-Wengenroth, Wuppertal (DE); Uwe Saatman, Wuppertal (DE); Julia Strassburger, Wuppertal (DE); Mark Jean Gnoth, Mettman (DE); Dieter Lang, Velbert (DE)

(73) Assignee: Bayer Intellectual Property GmbH, Monheim (DE)

( * ) Notice: Subject to any disclaimer, the term of this patent is extended or adjusted under 35 U.S.C. 154(b) by 53 days.

(21) Appl. No.: 12/665,728

(22) PCT Filed: Jun. 13, 2008

(86) PCT No.: PCT/EP2008/004746
§ 371 (c)(1),
(2), (4) Date: Jun. 28, 2010

(87) PCT Pub. No.: WO2008/155069
PCT Pub. Date: Dec. 24, 2008

(65) Prior Publication Data
US 2010/0298293 A1 Nov. 25, 2010

(30) Foreign Application Priority Data
Jun. 20, 2007 (DE) .......................... 10 2007 028 406

(51) Int. Cl.
C07D 413/14 (2006.01)
A61K 31/4439 (2006.01)
A61P 7/02 (2006.01)

(52) U.S. Cl. ............ 514/211.03; 514/255.05; 514/252.1; 514/326; 514/340; 514/342; 540/488; 544/316; 544/405; 546/208; 546/271.4

(58) Field of Classification Search .................. 540/488; 544/316, 405; 546/208, 271.4; 514/211.03, 514/255.05, 252.1, 326, 340, 342
See application file for complete search history.

(56) References Cited

U.S. PATENT DOCUMENTS

| 7,157,456 | B2 | 1/2007 | Straub et al. |
| 7,576,111 | B2 | 8/2009 | Straub et al. |
| 7,767,702 | B2 | 8/2010 | Straub et al. |
| 2003/0153610 | A1 | 8/2003 | Straub et al. |
| 2006/0069260 | A1 | 3/2006 | Zhang et al. |
| 2006/0258724 | A1 | 11/2006 | Straub et al. |
| 2008/0200674 | A1 | 8/2008 | Straub et al. |
| 2008/0306070 | A1 | 12/2008 | Perzborn |

FOREIGN PATENT DOCUMENTS

WO  WO 03/000256  *  1/2003

OTHER PUBLICATIONS

Heart Disease: A Textbook of Cardiovascular Medicine, Eugene Braunwald, 5. Auflage, 1997, W.B. Saunders Company, Philadelphia.
Pschyrembel, Klinisches Wörterbuch, 257. Auflage, 1994, Walter de Gruyter Verlag, Seite 610, Stichwort „Heparin.
Römpp Lexikon Chemie, Version 1.5, 1998, Georg Thieme Verlag Stutt¬ gart, Stichwort „Heparin.
J. Hirsh, J. Dalen, D.R. Anderson et al., "Oral anticoagulants: Mechanism of action, clinical effectiveness, and optimal therapeutic range" Chest 2001, 119, 8S-21S.
J. Ansell, J. Hirsh, J. Dalen et al., "Managing oral anticoagulant therapy" Chest 2001, 119, 22S-38S.
P.S. Wells, A.M. Holbrook, N.R. Crowther et al., "Interactions of warfarin with drugs and food" Ann. Intern. Med. 1994, 121, 676-683.
J.H. Sohn, et al., Appl. Microbiolog. Biotechn. 2001, 57, 606-613.
T. Gladwell, Clin. Ther. 2002, 24, 38-58.
G. Escolar, Drugs of Today, 2006, 42, 223.
J. Hauptmann, J. Stürzebecher, Thrombosis Research 1999, 93, 203-241.
S.A.V Raghavan, M. Dikshit, "Recent advances in the status and targets of antithrombotic agents" Drugs Fut. 2002, 27, 669-683.
H.A. Wieland, V. Laux, D. Kozian, M. Lorenz, "Approaches in anticoagulation: Rationales for target positioning" Curr. Opin. Investig. Drugs 2003, 4, 264-271.
U.J. Ries, W. Wienen, "Serine proteases as targets for antithrombotic therapy" Drugs Fut. 2003, 28, 355-370.
L.-A. Linkins, J.I. Weitz, "New anticoagulant therapy" Annu. Rev. Med. 2005, 56, 63-77.
A. Casimiro-Garcia et al., "Progress in the discovery of Factor Xa inhibitors", Expert Opin. Ther. Patents, 2006, 15, 119-145.
J.M. Walenga, W.P. Jeske, D. Hoppensteadt, J. Fareed, "Factor Xa Inhibitors: Today and beyond" Curr. Opin. Investig. Drugs 2003, 4, 272-281.
J. Ruef, H.A. Katus, "New anti¬ thrombotic drugs on the horizon" Expert Opin. Investig. Drugs 2003, 12, 781-797.
M.L. Quan, J.M. Smallheer, "The race to an orally active Factor Xa inhibitor: Recent advances" Curr. Opin. Drug Discovery & Development 2004, 7, 460-469.
Journal of Thrombosis and Haemostasis, 4, pp. 834-841, (2005).

(Continued)

*Primary Examiner* — Bruck Kifle
(74) *Attorney, Agent, or Firm* — Jonathan R. Harris; Thomas C. Blankinship

(57) ABSTRACT

The invention relates to novel substituted oxazolidinones, to processes for preparation thereof, to the use thereof for treatment and/or prophylaxis of diseases, and to the use thereof for producing medicaments for treatment and/or prophylaxis of diseases, especially of thromboembolic disorders.

8 Claims, No Drawings

OTHER PUBLICATIONS

International Search Report, Appl. No. PCT/EP2008/004563, dated Sep. 17, 2008.
International Search Report, Appl. No. PCT/EP2008/004746, dated Sep. 3, 2008.
International Search Report, Appl. No. PCT/EP2008/004562, dated Sep. 17, 2008.
Copending U.S. Appl. No. 12/665,718, filed Dec. 20, 2009.
Copending U.S. Appl. No. 12/665,729, filed Dec. 21, 2009.

* cited by examiner

SUBSTITUTED OXAZOLIDINONES AND THEIR USE

The invention relates to novel substituted oxazolidinones, to processes for preparation thereof, to the use thereof for treatment and/or prophylaxis of diseases, and to the use thereof for producing medicaments for treatment and/or prophylaxis of diseases, especially of thromboembolic disorders.

Blood coagulation is a protective mechanism of the organism, which helps to "seal" defects in the wall of the blood vessels quickly and reliably. Thus, loss of blood can be avoided or kept to a minimum. Hemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here, factors Xa and IIa (thrombin) play key roles.

Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin.

Through an array of reactions, thrombin transfers the signals from the cascade to the coagulation state of the blood. Thrombin cleaves fibrinogen directly to fibrin. It activates factor XIII, which is required for stabilizing the fibrin clot, to factor XIIIa. In addition, thrombin is a potent trigger of platelet aggregation (via PAR-1 activation), which also contributes considerably to hemostasis. By activating TAFI (thrombin-activatable fibrinolysis inhibitor) to TAFIa, thrombin in a complex with thrombomodulin inhibits the dissolution of the clot. Activation of factors V and VIII potentates the production of thrombin and thus in turn amplifies the coagulation reaction; the activated protein C, produced in a complex with thrombomodulin, antagonizes this increased thrombin production, thus preventing excessive hemostasis (thrombosis).

In addition to unbound factor X and thrombin in the blood, bound forms are also known. During the formation of a fibrin clot, thrombin and prothrombinase (factor Xa in a complex) are bound to the fibrin skeleton. These enzyme molecules are still active and cannot be inhibited by endogenous antithrombin III. Thus, in this manner, clots still have a general coagulative potential.

During the course of many cardiovascular and metabolic disorders, as a result of systemic factors, such as, for example, hyperlipidaemia, diabetes or smoking, owing to changes in the blood with stasis, such as, for example, atrial fibrillation, or owing to pathologic changes of the vascular walls, for example endothelial dysfunctions or atherosclerosis, there is an increased tendency of coagulation and platelet activation. This unwanted and excessive hemostasis can, by forming fibrin- and platelet-rich thrombi, cause thromboembolic disorders and thrombotic complications with life-threatening states.

Hemostasis is subject to a complex regulatory mechanism. Uncontrolled activation of the coagulation system or defect inhibition of the activation processes may lead to the formation of local thromboses or embolisms in vessels (arteries, veins, lymph vessels) or cardiac cavities. This may lead to serious thrombotic or thromboembolic disorders. In addition, systemic hypercoagulability may lead to consumption coagulopathy in the context of a disseminated intravasal coagulation. Thromboembolic complications are also encountered in microangiopathic hemolytic anaemias, extracorporeal circulatory systems, such as hemodialysis, and also prosthetic heart valves and stents.

Thromboembolic disorders are the most frequent cause of morbidity and mortality in most industrialized countries [Heart Disease: A Textbook of Cardiovascular Medicine, Eugene Braunwald, 5th edition, 1997, W.B. Saunders Company, Philadelphia].

The anticoagulants known from the prior art, for example substances for inhibiting or preventing blood coagulation, have various, frequently grave disadvantages. Accordingly, in practice, an efficient treatment method or the prophylaxis of thrombotic/thromboembolic disorders is found to be very difficult and unsatisfactory.

One agent used in the therapy and prophylaxis of thromboembolic disorders is heparin, which is administered parenterally or subcutaneously. Owing to more favorable pharmacokinetic properties, low molecular weight heparin is increasingly being preferred nowadays; however, the known disadvantages outlined hereinafter, which exist in treatment with heparin, cannot be avoided as a result. For instance, heparin is ineffective orally and possesses only a comparatively short half-life. Furthermore, there is a high risk of hemorrhage; more particularly, brain hemorrhage and hemorrhage in the gastrointestinal tract can occur, which can result in thrombopenia, alopecia medicomentosa or osteoporosis [Pschyrembel, Klinisches Wörterbuch [Clinical Dictionary], 257th edition, 1994, Walter de Gruyter Verlag, page 610, "Heparin"; Römpp Lexikon Chemie, Version 1.5, 1998, Georg Thieme Verlag Stuttgart, "Heparin"]. Although low molecular weight heparins possess a lower probability of developing heparin-induced thrombocytopenia, they are also administrable only subcutaneously. This is also true of fondaparinux, a synthetic selective factor Xa inhibitor with a long half-life.

A second class of anticoagulants is that of the vitamin K antagonists. These include, for example, 1,3-indandiones, but in particular compounds such as Warfarin, phenprocoumon, Dicumarol and other coumarin derivatives, which unselectively inhibit the synthesis of various products of particular vitamin K-dependent coagulation factors in the liver. As a result of the mechanism of action, the action sets in only very slowly (latent time until onset of action 36 to 48 hours). Although the compounds can be administered orally, the high risk of hemorrhage and the narrow therapeutic index necessitate laborious individual establishment of dose and observation of the patient [J. Hirsh, J. Dalen, D. R. Anderson et al., "Oral anticoagulants: Mechanism of action, clinical effectiveness, and optimal therapeutic range" *Chest* 2001, 119, 8S-21S; J. Ansell, J. Hirsh, J. Dalen et al., "Managing oral anticoagulant therapy" *Chest* 2001, 119, 22S-38S; P. S. Wells, A. M. Holbrook, N. R. Crowther et al., "Interactions of warfarin with drugs and food" *Ann. Intern. Med.* 1994, 121, 676-683]. Furthermore, further side effects such as gastrointestinal disorders, hair loss and skin necroses are described.

In addition, thrombin inhibitors are used to a minor degree. Hirudin is a protein which is a very potent thrombin inhibitor. In recombinant form, it is administered intravenously as a reserve anticoagulant. In bivalirudin a 20-amino acid fragment from Hirudin is available, which has a very short half-life and is also not administrable orally. The same applies to the direct non-peptidic low molecular weight thrombin inhibitor Argatroban [J. H. Sohn, et al. *Appl. Microbiol. Bio-* technol. 2001, 57, 606-613; T. Galdwell *Clin. Ther.* 2002, 24, 38-58; G. Escolar, *Drugs of Today* 2006, 42, 223].

A further treatment approach envisages the sole inhibition of factor Xa [J. Hauptmann, J. Stürzebecher, *Thrombosis Research* 1999, 93, 203; S. A. V. Raghavan, M. Dikshit, "Recent advances in the status and targets of antithrombotic agents" *Drugs Fut.* 2002, 27, 669-683; H. A. Wieland, V. Laux, D. Kozian, M. Lorenz, "Approaches in anticoagulation: Rationales for target positioning" *Curr. Opin. Investig. Drugs* 2003, 4, 264-271; U. J. Ries, W. Wienen, "Serine proteases as targets for antithrombotic therapy" *Drugs Fut.* 2003, 28, 355-370; L.-A. Linkins, J. I. Weitz, "New anticoagulant therapy" *Annu. Rev. Med.* 2005, 56, 63-77; A. Casimiro-Garcia et al., "Progress in the discovery of Factor Xa inhibitors" *Expert Opin. Ther. Patents* 2006, 15, 119-145].

In this context, it has been found that various, both peptidic and nonpeptidic, compounds are effective as factor Xa inhibitors in animal models. A large number of direct factor Xa inhibitors has become known to date [J. M. Walenga, W. P. Jeske, D. Hoppensteadt, J. Fareed, "Factor Xa Inhibitors: Today and beyond" *Curr. Opin. Investig. Drugs* 2003, 4, 272-281; J. Ruef, H. A. Katus, "New antithrombotic drugs on the horizon" *Expert Opin. Investig. Drugs* 2003, 12, 781-797; M. L. Quan, J. M. Smallheer, "The race to an orally active Factor Xa inhibitor: Recent advances" *Curr. Opin. Drug Discovery & Development* 2004, 7, 460-469]. Oxazolidinones as nonpeptidic, low molecular weight factor Xa inhibitors are described in WO 01/47919.

Recently, approaches have been described, in which low molecular weight thrombin and factor Xa inhibitors were tested in vitro and in vivo in various mixing ratios. A strong synergistic potential was found. In tanogitran, a low molecular weight substance has been described, which inhibits both thrombin and factor Xa, but possesses a strong preference for thrombin inhibition. This substance which is still in development is not bioavailable orally.

For antithrombotic medicaments, the therapeutic breadth is of central importance: The distance between the therapeutically active dose for coagulation inhibition and the dose where bleeding may occur should be as big as possible so that maximum therapeutic activity is achieved at a minimum risk profile.

As shown by the experiments with mixtures of low molecular weight thrombin and factor Xa inhibitors, compounds which inhibit both thrombin and factor Xa would, by virtue of their dual character, have a particularly strong synergism, thus being particularly effective in controlling the formation of thrombi. In this manner, the compounds inhibit the two key enzymes of the coagulation cascade, without completely blocking the individual enzymes. The remaining rest of factor Xa and thrombin results in an intact hemostasis and thus a particularly advantageous therapeutic width. In an arteriovenous shunt model in rabbits, it was possible to demonstrate that coadministration of only weakly antithrombotically active dosages of the selective factor Xa inhibitor PD0313052 and the selective thrombin inhibitor argatroban results in a strong superadditive antithrombotic effect. In addition, when the individual doses with the maximum synergistic effect were combined, no increased bleeding was observed. These observations allow the conclusion to be drawn that simultaneous inhibition of thrombin and factor Xa increases the therapeutic width with respect to the distance between antithrombotic action and bleeding risk (Journal of Thrombosis and Haemostasis, 4: 834-841).

This synergism is particularly pronounced when the prothrombin time as a function of the substance concentration is studied by direct comparison with pure factor Xa and thrombin inhibitors. This strong effect on the two key enzymes of the coagulation cascade is considered to be particularly advantageous when a high risk of thrombi formation is present, or when the formation of thrombi may result in a fatal disease. Both are relevant, for example, in the case of atherothrombotic disorders of the acute coronary syndrome type or the situation after an acute myocardial infarction.

Furthermore, in contrast to heparins, hirudin and vitamin K antagonists, compounds inhibiting both thrombin and factor Xa would also be active against coagulation factors bound to fibrin clots. The limitation of the thrombotic potential of an already existing clot is a critical point in the prevention of arterial occlusion. This is achieved particularly effectively by inhibiting both the present thrombin activity and the formation of new thrombin in the clot. Whereas a pure thrombin inhibitor cannot prevent the avalanche-like thrombin production by the clot-bound factor Xa-containing prothrombinase complex and the inhibitory effect can thus be overcompensated in a highly stimulated coagulation by the large amount of thrombin produced, pure factor Xa inhibitors are not capable of inhibiting the thrombin activity already present. Since inhibition is likewise not possible by physiological mechanisms, this clot-bound thrombin poses a particularly large risk. In contrast, dual compounds, i.e. compounds inhibiting both thrombin and factor Xa, are capable of inhibiting both the thrombin production and the thrombin activity on clots, thus also preventing a potential clot growth.

Accordingly, it is an object of the present invention to provide dual compounds, i.e. compounds which inhibit both thrombin and factor Xa and which, by inhibiting thrombin production and thrombin activity on clots, prevent their potential growth, with a broad therapeutic window, for controlling diseases, in particular thromboembolic disorders, in humans and animals.

The invention provides compounds of the formula

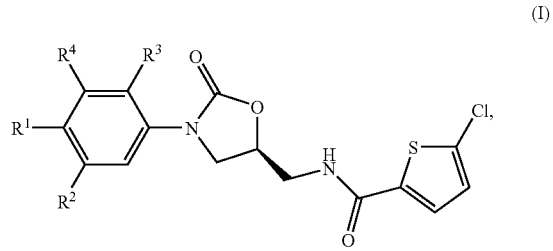

(I)

in which
$R^1$ is a group of the formula

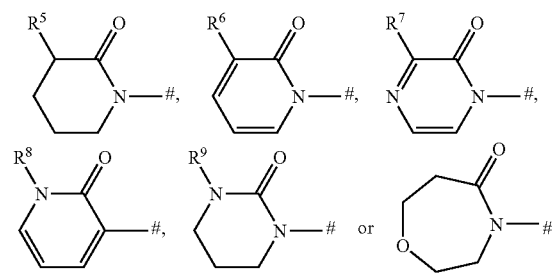

where
# is the attachment site to the phenyl ring,
$R^5$ is hydrogen or $C_1$-$C_3$-alkyl, in which alkyl may be substituted by a hydroxyl substituent,
$R^6$ is hydrogen, trifluoromethyl, trifluoromethoxy, difluoromethoxy, $C_1$-$C_3$-alkyl or $C_1$-$C_4$-alkoxy,
in which alkoxy may be substituted by a substituent, which substituent is selected from the group consisting of halogen, hydroxy, trifluoromethyl, aminocarbonyl, $C_1$-$C_3$-alkoxy, $C_1$-$C_3$-alkylcarbonyl, $C_1$-$C_4$-alkylaminocarbonyl and morpholinocarbonyl,
$R^7$ is hydrogen, $C_1$-$C_3$-alkyl or $C_1$-$C_4$-alkoxy,
in which $C_2$-$C_3$-alkyl and $C_2$-$C_4$-alkoxy may be substituted by a hydroxyl substituent,
$R^8$ is hydrogen or $C_1$-$C_3$-alkyl,
in which $C_2$-$C_3$-alkyl may be substituted by a hydroxyl substituent,
$R^9$ is hydrogen or $C_1$-$C_3$-alkyl,
in which $C_2$-$C_3$-alkyl may be substituted by a hydroxyl substituent,
$R^2$ is chlorine, trifluoromethyl, trifluoromethoxy, difluoromethoxy, methyl, ethyl, n-propyl, isopropyl, methoxy, ethoxy, methoxymethyl, ethoxymethyl or cyclopropyl,
$R^3$ is hydrogen, $C_1$-$C_3$-alkoxy or $C_1$-$C_3$-alkylamino,
$R^4$ is hydrogen or methyl,
and salts thereof, solvates thereof and the solvates of salts thereof.

Inventive compounds are the compounds of the formula (I) and the salts thereof, solvates thereof and solvates of the salts thereof, the compounds which are embraced by formula (I) and are of the formulae specified below and the salts thereof, solvates thereof and solvates of the salts thereof, and the compounds which are embraced by formula (I) and are specified below as working examples and salts thereof, solvates thereof and solvates of the salts thereof, if the compounds which are embraced by formula (I) and are specified below are not already salts, solvates and solvates of the salts.

Depending on their structure, the inventive compounds may exist in stereoisomeric forms (enantiomers, diastereomers). The invention therefore embraces the enantiomers or diastereomers and the particular mixtures thereof. The stereoisomerically homogeneous constituents can be isolated in a known manner from such mixtures of enantiomers and/or diastereomers.

When the inventive compounds can occur in tautomeric forms, the present invention embraces all tautomeric forms.

In the context of the present invention, preferred salts are physiologically acceptable salts of the inventive compounds. Also included are salts which are not suitable themselves for pharmaceutical applications, but, for example, can be used for the isolation or purification of the inventive compounds.

Physiologically acceptable salts of the inventive compounds include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalene-disulfonic acid, acetic acid, trifluoroacetic acid, propionic acid, lactic acid, tartaric acid, maleic acid, citric acid, fumaric acid, maleic acid and benzoic acid.

Physiologically acceptable salts of the inventive compounds also include salts of customary bases, for example and with preference alkali metal salts (e.g. sodium and potassium salts), alkaline earth metal salts (e.g. calcium and magnesium salts) and ammonium salts derived from ammonia or organic amines having 1 to 16 carbon atoms, for example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the inventive compounds which, in the solid or liquid state, form a complex by coordination with solvent molecules. Hydrates are a specific form of the solvates, in which the coordination is with water. Preferred solvates in the context of the present invention are hydrates.

In addition, the present invention also embraces prodrugs of the inventive compounds. The term "prodrugs" embraces compounds which may themselves be biologically active or inactive, but are converted to inventive compounds (for example metabolically or hydrolytically) during the residence time thereof in the body.

In the context of the present invention, the substituents, unless specified otherwise, are defined as follows:

alkyl per se and "alk" and "alkyl" in alkoxy, alkylamino, alkylcarbonyl and alkylaminocarbonyl is a linear alkyl radical having generally 1 to 3, preferably 1 or 2, carbon atoms, for example and with preference methyl, ethyl and n-propyl.

Alkoxy is, for example and with preference, methoxy, ethoxy and n-propoxy.

Alkylamino is an alkylamino radical having one or two (independently selected) alkyl substituents, for example and with preference methylamino, ethylamino, n-propylamino, isopropylamino, N,N-dimethylamino, N,N-diethylamino, N-ethyl-N-methylamino, N-methyl-N-n-propylamino and N-isopropyl-N-n-propylamino. $C_1$-$C_3$-Alkylamino is, for example, a monoalkylamino radical having 1 to 3 carbon atoms or a dialkylamino radical having in each case 1 to 3 carbon atoms per alkyl substituent.

Alkylcarbonyl is, for example and with preference, methylcarbonyl, ethylcarbonyl, n-propylcarbonyl and isopropylcarbonyl.

Alkylaminocarbonyl is an alkylaminocarbonyl radical having one or two (independently selected) alkyl substituents, for example and with preference methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl is, for example, a monoalkylaminocarbonyl radical having 1 to 4 carbon atoms or a dialkylaminocarbonyl radical having in each case 1 to 4 carbon atoms per alkyl substituent.

In the formulae of the group which can represent $R^1$, the end point of the line with a # alongside in each case is not a carbon atom or a $CH_2$ group, but rather is part of the bond to the atom to which $R^1$ is bonded.

A symbol * on a carbon atom means that the compound is present in enantiomerically pure form with regards to the configuration at this carbon atom, which is understood in the context of the present invention to mean an enantiomeric excess of more than 90% (>90% ee).

Preference is given to compounds of the formula (I) in which
$R^1$ is a group of the formula

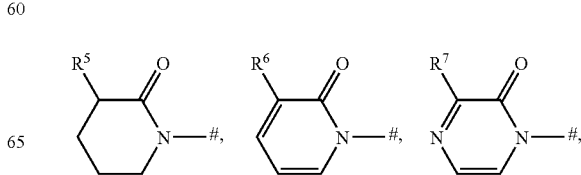

-continued

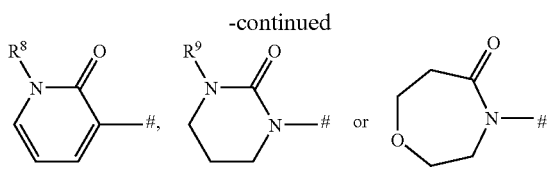

where
# is the attachment site to the phenyl ring,
$R^5$ is hydrogen or $C_1$-$C_3$-alkyl,
in which alkyl may be substituted by a hydroxyl substituent,
$R^6$ is hydrogen, trifluoromethyl, trifluoromethoxy, $C_1$-$C_3$-alkyl or $C_1$-$C_4$-alkoxy,
in which alkoxy may be substituted by a substituent, which substituent is selected from the group consisting of halogen, hydroxy, trifluoromethyl, aminocarbonyl, $C_1$-$C_3$-alkoxy, $C_1$-$C_3$-alkylcarbonyl, $C_1$-$C_4$-alkylaminocarbonyl and morpholinocarbonyl,
$R^7$ is $C_1$-$C_4$-alkoxy,
$R^8$ is $C_1$-$C_3$-alkyl,
$R^9$ is hydrogen or $C_1$-$C_3$-alkyl,
in which $C_2$-$C_3$-alkyl may be substituted by a hydroxyl substituent,
$R^2$ is chlorine, trifluoromethyl, methyl, ethyl, n-propyl, isopropyl, methoxy, ethoxy, methoxymethyl, ethoxymethyl or cyclopropyl,
$R^3$ is hydrogen, $C_1$-$C_3$-alkoxy or $C_1$-$C_3$-alkylamino,
$R^4$ is hydrogen or methyl,
and salts thereof, solvates thereof and the solvates of salts thereof.

Preference is also given to compounds of the formula (I) in which
$R^1$ is a group of the formula

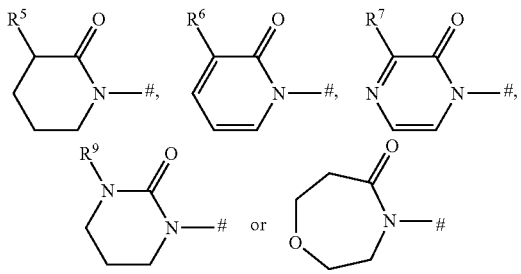

where
# is the attachment site to the phenyl ring,
$R^5$ is hydrogen or $C_1$-$C_3$-alkyl,
in which alkyl may be substituted by a hydroxyl substituent,
$R^6$ is hydrogen, trifluoromethyl, trifluoromethoxy, $C_1$-$C_3$-alkyl or $C_1$-$C_4$-alkoxy,
in which alkoxy may be substituted by a substituent, which substituent is selected from the group consisting of halogen, hydroxy, trifluoromethyl, aminocarbonyl, $C_1$-$C_3$-alkoxy, $C_1$-$C_3$-alkylcarbonyl, $C_1$-$C_4$-alkylaminocarbonyl and morpholinocarbonyl,
$R^7$ is $C_1$-$C_4$-alkoxy,
$R^9$ is hydrogen or $C_1$-$C_3$-alkyl,
in which $C_2$-$C_3$-alkyl may be substituted by a hydroxyl substituent,
$R^2$ is chlorine, trifluoromethyl, methyl, ethyl, n-propyl, isopropyl, methoxy, ethoxy, methoxymethyl, ethoxymethyl or cyclopropyl,
$R^3$ is hydrogen, $C_1$-$C_3$-alkoxy or $C_1$-$C_3$-alkylamino,
$R^4$ is hydrogen or methyl,
and the salts thereof, solvates thereof and the solvates of salts thereof.

Preference is also given to compounds of the formula (I) in which
$R^1$ is a group of the formula

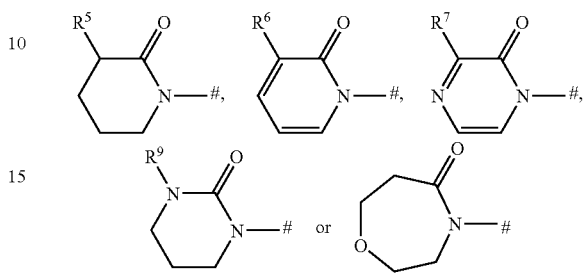

where
# is the attachment site to the phenyl ring,
$R^5$ is hydrogen or $C_1$-$C_3$-alkyl,
in which alkyl may be substituted by a hydroxyl substituent,
$R^6$ is hydrogen, $C_1$-$C_3$-alkyl or $C_1$-$C_4$-alkoxy,
in which alkoxy may be substituted by a substituent, which substituent is selected from the group consisting of hydroxy, aminocarbonyl, $C_1$-$C_3$-alkoxy, $C_1$-$C_3$-alkylcarbonyl and $C_1$-$C_4$-alkylaminocarbonyl,
$R^7$ is $C_1$-$C_4$-alkoxy,
$R^9$ is hydrogen or $C_1$-$C_3$-alkyl,
in which $C_2$-$C_3$-alkyl may be substituted by a hydroxyl substituent,
$R^2$ is chlorine, methyl, ethyl, n-propyl, isopropyl, methoxy, ethoxy, methoxymethyl, ethoxymethyl or cyclopropyl,
$R^3$ is hydrogen,
$R^4$ is hydrogen or methyl,
and salts thereof, solvates thereof and the solvates of salts thereof.

Preference is also given to compounds of the formula (I) in which
$R^1$ is a group of the formula

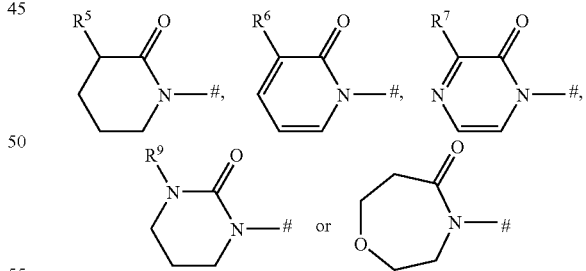

where
# is the attachment site to the phenyl ring,
$R^5$ is hydrogen,
$R^6$ is hydrogen or $C_1$-$C_4$-alkoxy,
in which alkoxy may be substituted by a hydroxyl substituent,
$R^7$ is ethoxy,
$R^9$ is hydrogen, methyl or 2-hydroxyeth-1-yl,
$R^2$ is methyl, isopropyl, methoxy, ethoxy, methoxymethyl or cyclopropyl,
$R^3$ is hydrogen,
$R^4$ is hydrogen or methyl, and salts thereof, solvates thereof and the solvates of salts thereof.

Preference is also given to compounds of the formula (I) in which
R¹ is a group of the formula

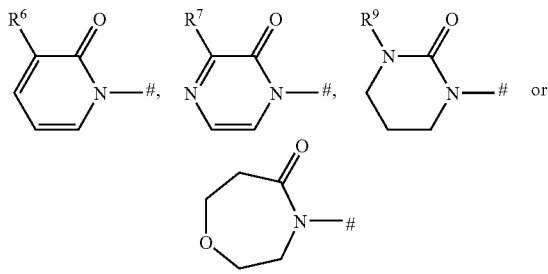

where
# is the attachment site to the phenyl ring,
R⁶ is hydrogen or $C_1$-$C_4$-alkoxy,
in which alkoxy may be substituted by a hydroxyl substituent,
R⁷ is ethoxy,
R⁹ is hydrogen, methyl or 2-hydroxyeth-1-yl.

Preference is also given to compounds of the formula (I) in which
R¹ is a group of the formula

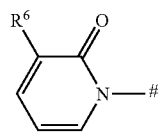

where
# is the attachment site to the phenyl ring,
R⁶ is hydrogen or $C_1$-$C_4$-alkoxy,
in which alkoxy may be substituted by a hydroxyl substituent.

Preference is also given to compounds of the formula (I) in which
R¹ is a group of the formula

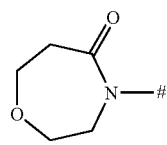

where
# is the attachment site to the phenyl ring.

Preference is also given to compounds of the formula (I) in which R² is chlorine, trifluoromethyl, methyl, ethyl, n-propyl, isopropyl, methoxy, ethoxy, methoxymethyl, ethoxymethyl or cyclopropyl.

Preference is also given to compounds of the formula (I) in which R² is methyl, isopropyl, methoxy, ethoxy, methoxymethyl or cyclopropyl.

Preference is also given to compounds of the formula (I) in which R² is chlorine, methyl or methoxy.

Preference is also given to compounds of the formula (I) in which R² is methyl.

Preference is also given to compounds of the formula (I) in which R³ is hydrogen.

Preference is also given to compounds of the formula (I) in which R⁴ is hydrogen.

Preference is also given to compounds of the formula (I) in which R⁶ is hydrogen, trifluoromethyl, trifluoromethoxy, $C_1$-$C_3$-alkyl or $C_1$-$C_4$-alkoxy, in which alkoxy may be substituted by a substituent, where the substituent is selected from the group consisting of halogen, hydroxy, trifluoromethyl, aminocarbonyl, $C_1$-$C_3$-alkoxy, $C_1$-$C_3$-alkylcarbonyl, $C_1$-$C_4$-alkylaminocarbonyl and morpholinocarbonyl.

The specific radical definitions given in the particular combinations or preferred combinations of radicals are, irrespective of the particular combination of the radical specified, also replaced by any radical definitions of other combinations.

Very particular preference is given to combinations of two or more of the abovementioned preferred ranges.

The invention further provides a process for preparing the compounds of the formula (I), or salts thereof, solvates thereof or the solvates of salts thereof, wherein

[A] the compound of the formula

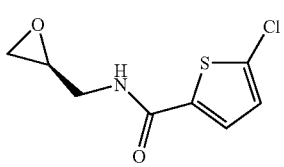

is reacted in the first stage with compounds of the formula

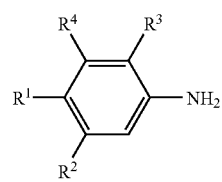

in which R¹, R², R³ and R⁴ are each as defined above
to give compounds of the formula

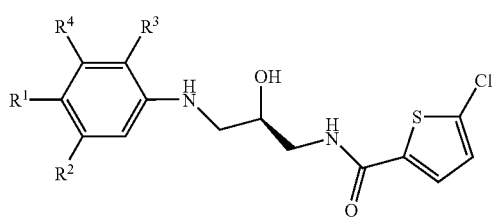

in which R¹, R², R³ and R⁴ are each as defined above,
and, in the second stage, in the presence of phosgene or phosgene equivalents such as carbonyldiimidazole (CDI), the compounds are cyclized to the compounds of the formula (I), or

[B] the compounds of the formula

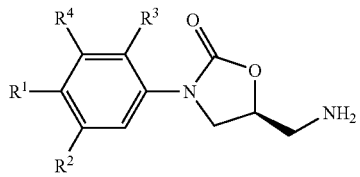

in which $R^1$, $R^2$, $R^3$ and $R^4$ are each as defined above are reacted with compounds of the formula

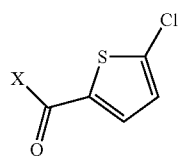

in which

X is halogen, preferably bromine or chlorine, or hydroxy.

When hydroxy groups are protected during the process, for example by a silyl protective group, they are detached by methods known to those skilled in the art after process [A] or [B] has ended, for example by reaction with tetrabutylammonium fluoride in a solvent, for example tetrahydrofuran, or by reaction with hydrogen chloride in methanol.

The free base of the salts can be obtained, for example, by chromatography on a reversed phase column using an acetonitrile/water gradient with addition of a base, in particular by using an RP18 Phenomenex Luna C18(2) column and diethylamine as base, or by dissolving the salts in an organic solvent and extracting with aqueous solutions of basic salts such as sodium bicarbonate.

The invention further provides a process for preparing the compounds of the formula (I) or solvates thereof, in which salts of the compounds or solvates of the salts of the compounds are converted to the compounds by chromatography with addition of a base.

The reaction of the first stage in process [A] is generally effected in inert solvents in the presence of a Lewis acid, preferably in a temperature range of from room temperature up to reflux of the solvent at atmospheric pressure.

Inert solvents are, for example, polar aprotic solvents, for example acetonitrile, butyronitrile, dichloromethane or chloroform; preference is given to acetonitrile.

Lewis acids are, for example, magnesium perchlorate, ytterbium(III) trifluoromethanesulfonate, lithium bromide, magnesium triflate or aluminum trichloride; preference is given to magnesium perchlorate.

The reaction of the second stage in process [A] is generally carried out in inert solvents, in the presence of a base, preferably in a temperature range of from room temperature to reflux of the solvent at atmospheric pressure.

Inert solvents are, for example, polar aprotic solvents, for example acetonitrile or butyronitrile.

Bases are, for example, strong tertiary amine bases, for example 4-N,N-dimethylaminopyridine.

Preference is given to the reaction with N,N'-carbonyldiimidazole as carbonic acid equivalent with addition of 4-N,N-dimethylaminopyridine as base.

When X in process [B] is halogen, the reaction is generally effected in inert solvents, optionally in the presence of a base, preferably in a temperature range of from −30° C. to 50° C. at atmospheric pressure.

Inert solvents are, for example, tetrahydrofuran, methylene chloride, pyridine, dioxane or dimethylformamide, preference is given to tetrahydrofuran or methylene chloride.

Bases are, for example, triethylamine, diisopropylethylamine or N-methylmorpholine; preference is given to diisopropylethylamine.

When X in process [B] is hydroxy, the reaction is generally effected in inert solvents, in the presence of a dehydrating reagent, optionally in the presence of a base, preferably in a temperature range of from −30° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is also possible to use mixtures of the solvents. Particular preference is given to dichloromethane or dimethylformamide.

Suitable dehydrating reagents here are, for example, carbodiimides, for example N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds, such as carbonyldiimidazole, or 1,2-oxazolium compounds, such as 2-ethyl-5-phenyl-1,2-oxazolium 3-sulfate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates, for example sodium carbonate or potassium carbonate, or sodium bicarbonate or potassium bicarbonate, or organic bases, such as trialkylamines, for example triethylamine, N-methylmorpholine, N-methylpiperidine, 4-dimethylaminopyridine or diisopropylethylamine.

The condensation with HATU or with EDC is preferably carried out in the presence of HOBt.

The compounds of the formulae (II) and (VI) are known or can be synthesized by known processes from the corresponding starting compounds.

The compounds of the formula (III) are known or can be prepared by reducing the nitro group in compounds of the formula

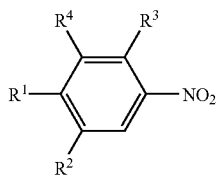

in which $R^1$, $R^2$, $R^3$ and $R^4$ are each as defined above.

The reaction is generally effected using a reducing agent in inert solvents, preferably in a temperature range of from room temperature to reflux of the solvents at from atmospheric pressure to 3 bar.

Reducing agents are, for example, palladium on activated carbon and hydrogen, tin dichloride, titanium trichloride, hydrazine hydrate and Raney nickel, or ammonium formate and palladium on activated carbon in a mixture of ethanol and ethyl acetate; preference is given to palladium on activated carbon and hydrogen or tin dichloride.

Inert solvents are, for example, ethers such as diethyl ether, methyl tert-butyl ether, 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or mineral oil fractions, or other solvents such as dimethylformamide, dimethylacetamide, acetonitrile or pyridine; preferred solvents are methanol, ethanol, isopropanol or, in the case of tin dichloride, in dimethylformamide.

The compounds of the formula (VII) are known, can be synthesized by known processes from the corresponding starting materials or can be prepared analogously to the process described in the examples section.

The compounds of the formula (V) are known or can be prepared by detaching the phthalimide protective group from compounds of the formula

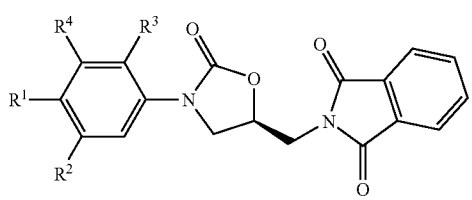

in which $R^1$, $R^2$, $R^3$ and $R^4$ are each as defined above.

The reaction is generally effected using an aqueous methylamine solution or a solution of hydrazine hydrate in ethanol, preferably using an aqueous methylamine solution at reflux of the solvents under atmospheric pressure.

The compounds of the formula (VIII) are known, can be prepared as described under process [A] or can by synthesized by known processes from the corresponding starting compounds.

The preparation of the inventive compounds can be illustrated by the following synthesis scheme:

Scheme 1

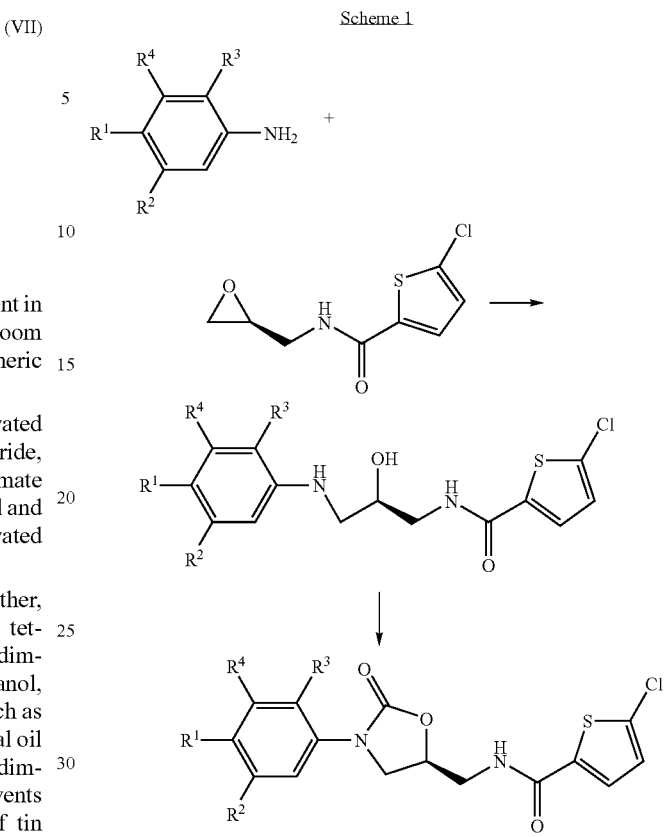

The inventive compounds have an unforeseeable useful spectrum of pharmacological activity.

Accordingly they are suitable for use as medicaments for treatment and/or prophylaxis of diseases in humans and animals.

The inventive compounds are dual inhibitors of the blood coagulation factors Xa and thrombin (factor IIa), which act, in particular, as anticoagulants. The compounds inhibit both thrombin and factor Xa, prevent their potential growth by inhibiting thrombin production and activity on clots, and have a wide therapeutic window.

The present invention further provides for the use of the inventive compounds for treatment and/or prophylaxis of disorders, preferably thromboembolic disorders and/or thromboembolic complications.

"Thromboembolic disorders" in the sense of the present invention are in particular disorders such as myocardial infarction with ST segment elevation (STEMI) and without ST segment elevation (non-STEMI), stable angina pectoris, unstable angina pectoris, reocclusions and restenoses after coronary interventions such as angioplasty or aortocoronary bypass, peripheral arterial occlusion diseases, pulmonary embolisms, deep venous thromboses and kidney venous thromboses, transitory ischemic attacks and also thrombotic and thromboembolic stroke.

Accordingly, the inventive compounds are also suitable for the prevention and treatment of cardiogenic thromboembolisms, for example cerebral ischemias, stroke and systemic thromboembolisms and ischemias, in patients having acute, intermittent or persistent cardial arrhythmias, for example atrial fibrillation, and those undergoing cardioversion, and also in patients having cardiac valve disorders or having artificial cardiac valves.

Thromboembolic complications are also encountered in microangiopathic hemolytic anemias, extracorporeal circulatory systems, such as hemodialysis, and prosthetic heart valves.

In addition, the inventive compounds are also suitable for the prophylaxis and/or treatment of atherosclerotic vascular disorders and inflammatory disorders such as rheumatic disorders of the locomotor apparatus, and in addition also for the prophylaxis and/or treatment of Alzheimer's disease. In addition, the inventive compounds can be used for inhibiting tumor growth and formation of metastases, for microangiopathies, age-related macula degeneration, diabetic retinopathy, diabetic nephropathy and other microvascular disorders, and also for the prevention and treatment of thromboembolic complications, for example venous thromboembolisms, for tumor patients, in particular those undergoing major surgical interventions or chemo- or radiotherapy.

In addition, the inventive compounds are also suitable for the prophylaxis and/or treatment of pulmonary hypertension.

The term "pulmonary hypertension" includes certain forms of pulmonary hypertension, as determined, for example, by the World Health Organization (WHO) (*Clinical Classification of Pulmonary Hypertension*, Venice 2003). Examples include pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" comprises idiopathic pulmonary arterial hypertension (IPAH, formerly also referred to as primary pulmonary hypertension), familiar pulmonary arterial hypertension (FPAH) and associated pulmonary-arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasy, hemoglobinopathies, myeloproliferative disorders, splenectomy), with disorders having a significant venous/capillary contribution, such as pulmonary-venoocclusive disorder and pulmonary-capillary hemangiomatosis, and also persisting pulmonary hypertension of neonates.

Pulmonary hypertension associated with disorders of the left heart comprises a diseased left atrium or ventricle and mitral or aorta valve defects.

Pulmonary hypertension associated with pulmonary disorders and/or hypoxia comprises chronic obstructive pulmonary disorders, interstitial pulmonary disorder, sleep apnea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumor, parasites, foreign bodies).

The present invention further provides for the use of the inventive compounds for producing medicaments for treatment and/or prophylaxis of pulmonary hypertension associated with sarcoidosis, histiocytosis X and lymphangiomatosis.

In addition, the inventive substances may also be suitable for treatment of pulmonary and hepatic fibroses.

In addition, the inventive compounds may also be suitable for the treatment and/or prophylaxis of sepsis (or septicemia), systemic inflammatory syndrome (SIRS), septic organ dysfunction, septic organ failure and multiorgan failure, acute respiratory distress syndrome (ARDS), acute lung injury (ALI), septic shock, DIC (disseminated intravascular coagulation or consumption coagulopathy) and/or septic organ failure.

"Sepsis" is defined as the presence of an infection and a systemic inflammatory response syndrome (referred to hereinafter as "SIRS"). SIRS occurs in association with infections, but also other states such as injuries, burns, shock, operations, ischemia, pancreatitis, reanimation or tumors. The definition of the ACCP/SCCM Consensus Conference Committee from 1992 (Crit Care Med 1992; 20:864-874) describes the diagnosis symptoms and measuring parameters required for the diagnosis of "SIRS" (including body temperature change, increased pulse, breathing difficulties and changed blood picture). The later (2001) SCCM/ESICM/ACCP/ATS/SIS International Sepsis Definitions Conference essentially kept the criteria, but fine-tuned details (Levy et al., Crit Care Med 2003; 31:1250-1256).

In the course of sepsis, there may be a generalized activation of the coagulation system (disseminated intravascular coagulation or consumption coagulopathy, referred to hereinafter as "DIC") with microthromboses in various organs and secondary hemorrhagic complications. Moreover, there may be endothelial damage with increased permeability of the vessels and seeping of fluids and proteins into the extravasal space. As the sepsis progresses, there may be failure of an organ (for example kidney failure, liver failure, respiratory failure, central-nervous deficits and/or cardiovascular failure) or multiorgan failure. "Septic shock" refers to the onset of hypotension requiring treatment, which hypotension promotes further organ damage and is associated with a worsening of the prognosis.

Pathogens may be bacteria (Gram-negative and Gram-positive), fungi, viruses and/or eukaryotes. Entrance point or primary infection may be, for example, pneumonia, an infection of the urinary tract or peritonitis. Infection can be, but is not necessarily, associated with bacteremia.

DIC and/or SIRS may occur during sepsis, but also as a result of operations, tumor diseases, burns or other injuries. In DIC, there is a massive activation of the coagulatory system at the surface of damaged endothelial cells, the surfaces of foreign bodies or injured extravascular tissue. As a result, there is coagulation in small vessels of various organs with associated hypoxia and subsequent organ dysfunction. Secondarily, there is a consumption of coagulation factors (for example factor X, prothrombin and fibrinogen) and platelets, which reduces the ability of the blood to coagulate and may result in serious bleeding.

Treatment of sepsis consists, firstly, of consequent elimination of the infectious cause, for example by operative focal reconstruction and antibiosis. Secondly, it consists in temporary intensive medical support of the affected organ systems. Therapies of various stages of this disease have been described, for example, in the following publication (Dellinger et al., Crit Care Med 2004; 32:858-873). For DIC, there are no proven effective therapies.

The invention further provides medicaments comprising an inventive compound and one or more further active ingredients, in particular for treatment and/or prophylaxis of the disorders mentioned above. Exemplary and preferred active ingredient combinations are:

Antibiotic Therapy

Various antibiotics or antifungal medicament combinations are suitable, either as calculated therapy (prior to the presence of the microbial diagnosis) or as specific therapy.

Fluid Therapy
for example crystalloids or colloidal fluids.
Vasopressors
for example norepinephrins, dopamines or vasopressin
Inotropic Therapy
for example dobutamine
Corticosteroids
for example hydrocortisone, or fludrocortisone
Recombinant Human Activated Protein C
Xigris
Blood Products
for example erythrocyte concentrates, platelet concentrates, erythropoietin or fresh frozen plasma
Artificial Ventilation in the Case of Sepsis-Induced Acute Lung Injury (ALI) or Acute Respiratory Distress Syndrome (ARDS)
for example permissive hypercapnia, reduced tidal volumes
Sedation, Analgesia and Neuromuscular Blockade
Sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium
Glucose Control
for example insulin, glucose
Renal Replacement Methods
for example continuous veno-venous hemofiltration or intermittent hemodialysis. Low doses of dopamine for renal protection.
Anticoagulants
for example for thrombosis prophylaxis or renal replacement methods, for example unfractionated heparins, low-molecular-weight heparins, heparinoids, hirudin, bivalirudin or argatroban.
Bicarbonate Therapy
Stress Ulcer Prophylaxis
for example H2-receptor inhibitors, antacids
In addition, the inventive compounds can also be used for prevention of coagulation ex vivo, for example for preservation of blood and plasma products, for cleaning/pretreatment of catheters and other medical aids and instruments, for coating of synthetic surfaces of medical aids and instruments used in vivo or ex vivo or for biological samples comprising factor Xa and/or factor IIa.

The present invention further provides for the use of the inventive compounds for treatment and/or prophylaxis of disorders, in particular the disorders mentioned above.

The present invention further provides for the use of the inventive compounds for preparing a medicament for treatment and/or prophylaxis of disorders, in particular the disorders mentioned above.

The present invention further provides a method for treatment and/or prophylaxis of disorders, in particular the disorders mentioned above, using an anticoagulatory effective amount of the inventive compound.

The present invention further provides a method for preventing the coagulation of blood in vitro, in particular in banked blood or biological samples containing factor Xa and/or factor IIa, which method is characterized in that an anticoagulatory effective amount of the inventive compound is added.

The present invention further provides medicaments comprising an inventive compound and one or more further active ingredients, in particular for treatment and/or prophylaxis of the disorders mentioned above. Preferred examples of suitable combinations of active ingredients include:

lipid-lowering substances, in particular HMG-CoA-(3-hydroxy-3-methylglutaryl-coenzyme A) reductase inhibitors, for example lovastatin (Mevacor; U.S. Pat. No. 4,231,938), simvastatin (Zocor; U.S. Pat. No. 4,444,784), pravastatin (Pravachol; U.S. Pat. No. 4,346,227), fluvastatin (Lescol; U.S. Pat. No. 5,354,772) and atorvastatin (Lipitor; U.S. Pat. No. 5,273,995);

coronary therapeutics/vasodilatators, in particular ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan (U.S. Pat. No. 5,863,930), losartan, valsartan, irbesartan, candesartan, eprosartan and temisartan, or β-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase (WO 98/16223, WO 98/16507, WO 98/23619, WO 00/06567, WO 00/06568, WO 00/06569, WO 00/21954, WO 00/66582, WO 01/17998, WO 01/19776, WO 01/19355, WO 01/19780, WO 01/19778, WO 07/045, 366, WO 07/045,367, WO 07/045,369, WO 07/045,370, WO 07/045,433);

plasminogen activators (thrombolytics/fibrinolytics) and compounds which promote thrombolysis/fibrinolysis, such as inhibitors of the plasminogen activator inhibitor (PAI inhibitors) or inhibitors of the thrombin-activated fibrinolysis inhibitor (TAFI inhibitors), for example tissue plasminogen activator (t-PA), streptokinase, reteplase and urokinase;

anticoagulatory substances (anticoagulants), for example heparin (UFH), low-molecular-weight heparins (NMH), for example tinzaparin, certoparin, parnaparin, nadroparin, ardeparin, enoxaparin, reviparin, dalteparin, danaparoid, AVE 5026 (Sanofi-Aventis, *Company Presentation* 2008, Feb. 12), M118 (Momenta Pharmaceuticals Inc, *Press Release* 2008, Feb. 14), ORG42675 (Organon International Inc, *Company World Wide Website* 2007, April), and direct thrombin inhibitors (DTI), for example

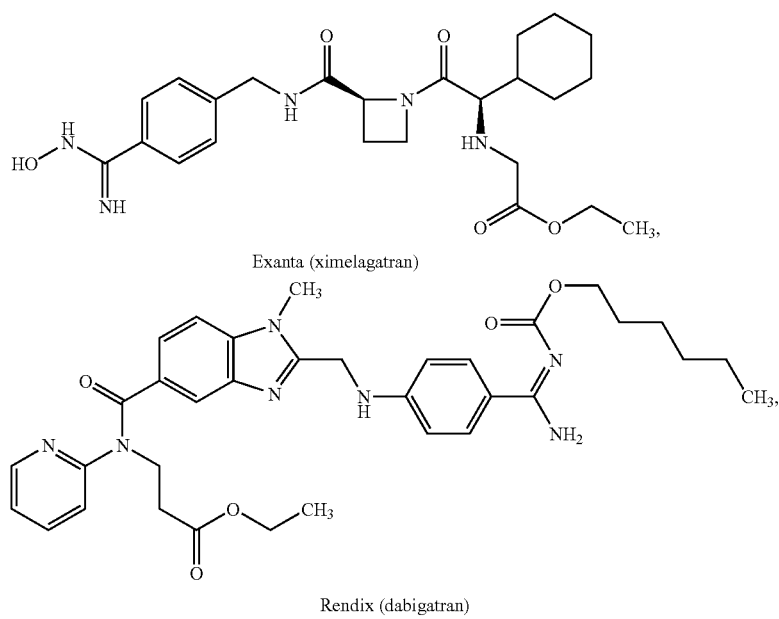

Exanta (ximelagatran)

Rendix (dabigatran)

AZD-0837 [AstraZeneca Annual Report 2006, Mar. 19, 2007]

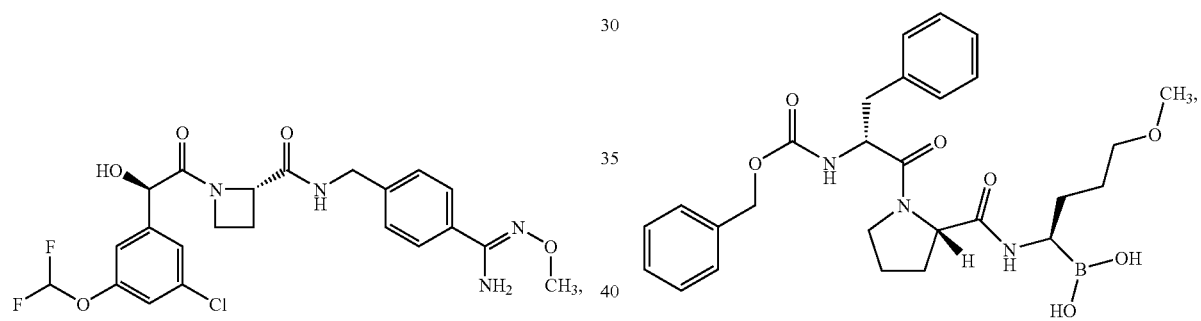

SSR-182289A [J. Lorrain et al. *Journal of Pharmacology and Experimental Therapeutics* 2003, 304, 567-574; J-M Altenburger et al. *Bioorg. Med. Chem.* 2004, 12, 1713-1730]

Sofigatran [*WHO Drug Information* 2007, 21, 77]

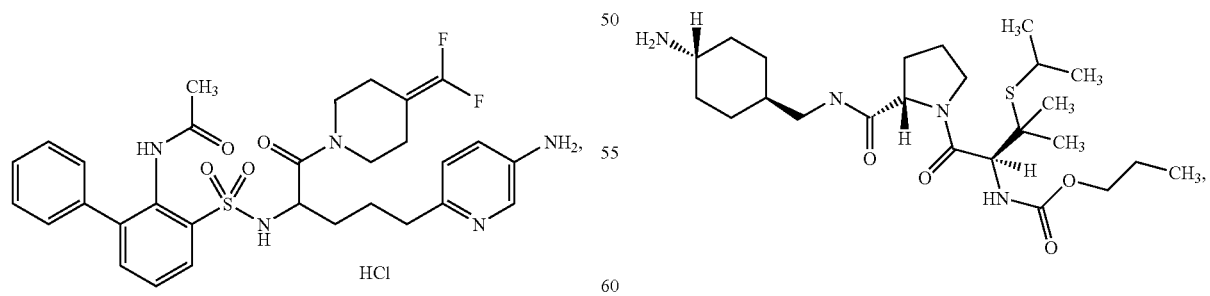

TGN-167 [S. Combe et al. *Blood* 2005, 106, abstract 1863 (ASH 2005)],

N-[(benzyloxy)carbonyl]-L-phenylalanyl-N-[(1S)-1-(dihydroxyboryl)-4-methoxybutyl]-D-prolinamide [WO 2005/084685]

MCC-977 [Mitsubishi Pharma website pipeline 2006, Jul. 25, 2006],

MPC-0920 [Press Release: "Myriad Genetics Begins Phase 1 Trial of Anti-Thrombin Drug MPC-0920", Myriad Genetics Inc, May 2, 2006] and TGN-255 (flovagatran)

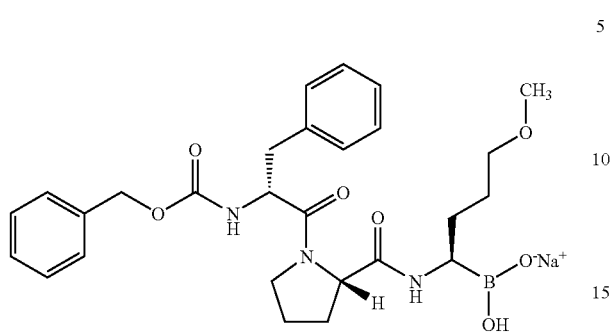

and direct factor Xa inhibitors, for example rivaroxaban (BAY 59-7939): 5-chloro-N-({(5S)-2-oxo-3-[4-(3-oxomorpholin-4-yl)phenyl]-1,3-oxazolidin-5-yl}methyl)thiophene-2-carboxamide [WO 2001/47919]

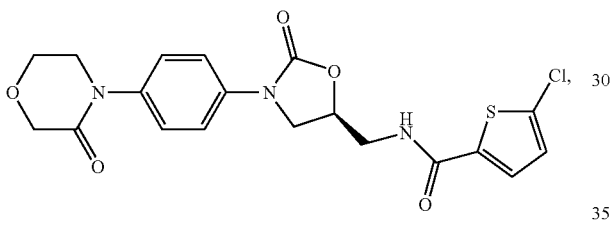

AX-1826 [S. Takehana et al. *Japanese Journal of Pharmacology* 2000, 82 (Suppl. 1), 213P; T. Kayahara et al. *Japanese Journal of Pharmacology* 2000, 82 (Suppl. 1), 213P], tanogitran (BIBT-986, prodrug: BIBT-1011): N-[(1R)-1-{2-[({4-[amino(imino)methyl]phenyl}amino)methyl]-1-methyl-1H-benzimidazol-5-yl}-1-methyl-2-oxo-2-pyrrolidin-1-ylethyl]glycine [American Chemical Society—226th National Meeting, New York City, N.Y., USA, 2003]

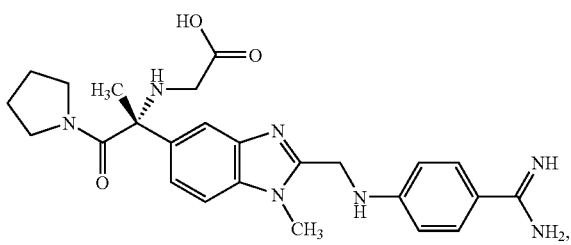

compounds disclosed in WO 2004/056784,

YM-150 [Y. Iwatsuki et al. *Blood* 2006, 108, abstract 911 (ASH 2006)],

N-{4-bromo-2-[(5-chloropyridin-2-yl)carbamoyl]-6-hydroxyphenyl}-1-isopropylpiperidine-4-carboxamide [JP 2005/179272]

compounds disclosed in WO 2000/242270,

AZ12300547: 6-[4-({(2S)-4-[(3-chloro-1H-indol-6-yl)sulfonyl]-2-methyl-6-oxopiperazin-1-yl}methyl)phenyl]-2-methylpyridazin-3(2H)-one [K. L Granberg et al. American Chemical Society—232nd National Meeting, San Francisco, USA, 2006, MEDI 391]

compounds disclosed in WO 2007/008142, razaxaban (DPC-906): 1-(3-amino-1,2-benzisoxazol-5-yl)-N-(4-{2-[(dimethylamino)methyl]-1H-imidazol-1-yl}-2-fluorophenyl)-3-(trifluoromethyl)-1H-pyrazole-5-carboxamide [*J. Med. Chem.* 2005, 48, 1729-1744]

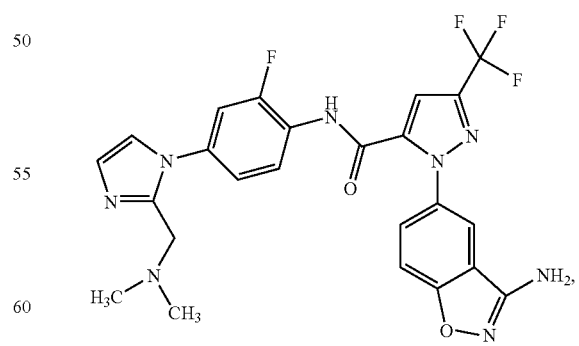

apixaban (BMS-562247): 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide [WO 2003/026652, WO 2003/049681]

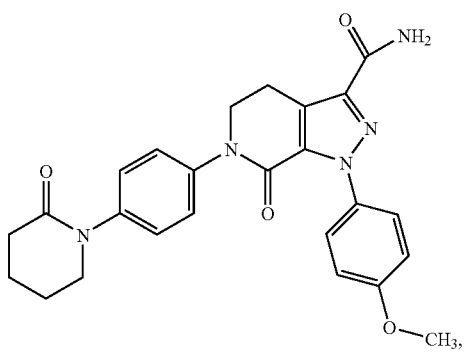

BMS-691648: 3-chloro-N-[(3S,4R)-1-(methylsulfonyl)-4-{[4-(2-oxopyridin-1(2H)-yl)benzoyl]amino}piperidin-3-yl]-1H-indole-6-carboxamide [T. Güngör et al. *Drugs Fut.* 2006, 31(Suppl A): abstract P118; WO 2004/082687]

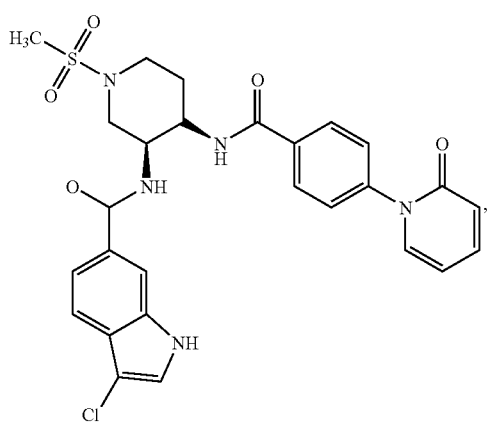

DX-9065a: (2S)-3-{7-[amino(imino)methyl]-2-naphthyl}-2-(4-{[(3S)-1-ethanimidoyl-pyrrolidin-3-yl]oxy}phenyl)propanoic acid [T. Nagahara et al. *J. Med. Chem.* 1994, 37, 1200-1207]

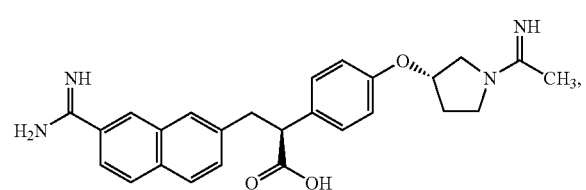

DU-176b [Y. Morishima et al. *Blood* 2004, 104, abstract 1862 (ASH 2004); T. Fukuda et al. *Blood* 2004, 104, abstract 1852 (ASH 2004); T. Furugohri et al. *Blood* 2004, 104, abstract 1851 (ASH 2004)], N-(5-chloropyridin-2-yl)-N'-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide [US 2005/0020645, WO 2005/47296]

compounds disclosed in US 2005/0020645,

LY517717: N-{(1R)-2-[4-(1-methylpiperidin-4-yl)piperazin-1-yl]-2-oxo-1-phenylethyl}-1H-indole-6-carboxamide [WO 2000/76971, WO 2002/100847]

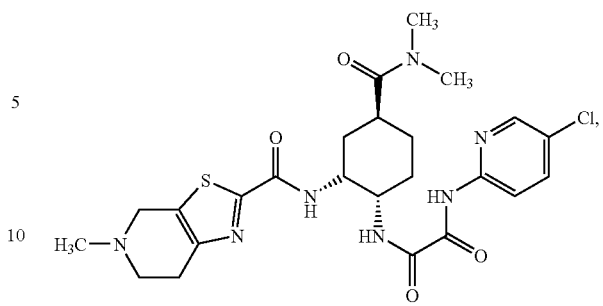

813893 [Proteinase Inhibitor Design—Fourth SCI-RSC Symposium, Proteinase 2004: Strategies for New Medicines (Part I), London], 6-chloro-N-{(3S)-1-[(1S)-1-methyl-2-morpholin-4-yl-2-oxoethyl]-2-oxopyrrolidin-3-yl}naphthalene-2-sulfonamide [N. S. Watson et al. *Bioorg. Med. Chem. Lett.* 2006, 16, 3784; WO 2002/100830; WO 2002/100886]

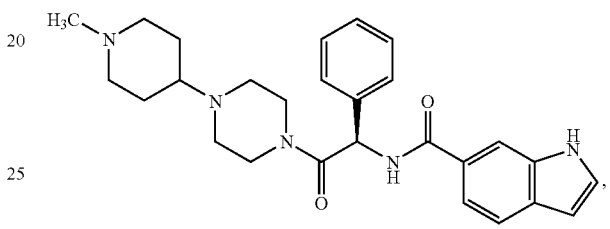

KFA-1982 (prodrug of KFA-1829) [T. Koizumi et al. *Journal of Thrombosis and Hemostasis* 2003, 1 Suppl 1, P2022], EMD-503982 [Merck KGaA Annual Report 2006, 48-49], EMD-495235: 5-chloro-N-[(1R)-1-(methoxymethyl)-2-{[3-methyl-4-(3-oxomorpholin-4-yl)-phenyl]amino}-2-oxoethyl]thiophene-2-carboxamide [*Bioorg. Med. Chem. Lett.* 2004, 14, 5817-5822]

M-55113: 4-[(6-chloro-2-naphthyl)sulfonyl]-1-[(1-pyridin-4-ylpiperidin-4-yl)methyl]piperazin-2-one [H. Nishida et al. *Chem. Pharm. Bull.* 2001, 49, 1237-1244]

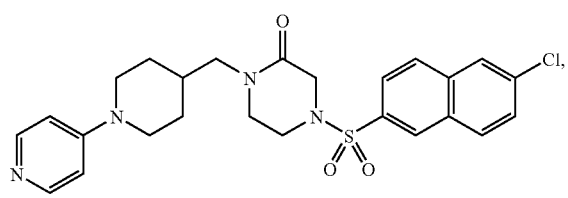

M-55551/M-55555: (2R)-4-[(6-chloro-2-naphthyl)sulfonyl]-6-oxo-1-[(1-pyridin-4-ylpiperidin-4-yl)methyl]piperazine-2-carboxylic acid [H. Nishida et al. *Chem. Pharm. Bull.* 2002, 50, 1187-1194]

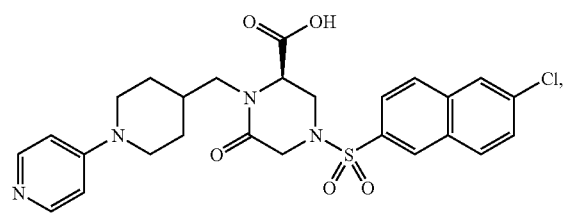

M-55190: ethyl (2R)-4-[(6-chloro-2-naphthyl)sulfonyl]-6-oxo-1-[(1-pyridin-4-ylpiperidin-4-yl)methyl]piperazine-2-carboxylate [H. Nishida et al. 16th Int Symp Med Chem, Bologna, Sep. 18-22, 2000, Abst PA-125]

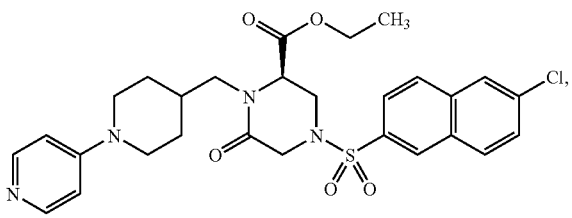

M-55532: 7-[(6-chloro-2-naphthyl)sulfonyl]-8a-(methoxymethyl)-1'-pyridin-4-yltetrahydro-5H-spiro[1,3-oxazolo[3,2-a]pyrazine-2,4'-piperidin]-5-one [H. Nishida et al. 228th ACS National Meeting, Philadelphia, Aug. 22-26, 2004, MEDI-251; H. Nishida et al. *Chem. Pharm. Bull.* 2004, 52, 406-412; ditto 459-462]

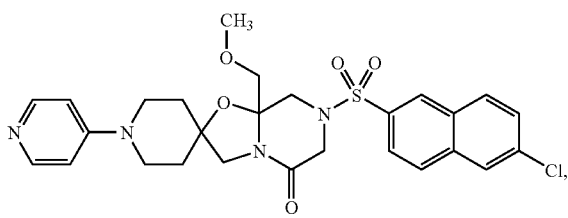

N-({7-[(5-chloro-1H-indol-2-yl)sulfonyl]-5-oxo-1'-propionyltetrahydro-8aH-spiro[1,3-oxazolo-[3,2-a]pyrazine-2,4'-piperidin]-8a-yl}methyl)-N-methylglycine [WO 2006/106804]

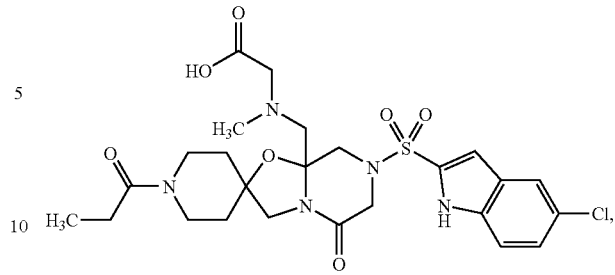

PRT54021 [U. Sinha et al. *Blood* 2006, 108, abstract 907 (ASH 2006); K. Abe et al. *Blood* 2006, 108, abstract 901 (ASH 2006)], compounds disclosed in WO 2006/002099, otamixaban (FXV-673, RPR-130673): methyl (2R,3R)-2-{3-[amino(imino)methyl]benzyl}-3-{[4-(1-oxidopyridin-4-yl)benzoyl]amino}butanoate [V. Chu et al. *Thrombosis Research* 2001, 103, 309-324; K. R. Guertin et al. *Bioorg Med. Chem. Lett.* 2002, 12, 1671-1674]

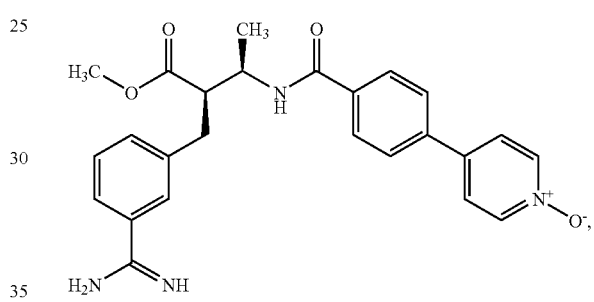

AVE3247 [Sanofi Aventis Company Presentation, Paris 2007, Feb. 13],

SAR377142 (SSR-7142) [Sanofi Aventis Company Presentation, Paris 2007, Feb. 13], HMR-2906 [XVIIth Congress of the International Society for Thrombosis and Haemostasis, Washington D.C., USA, Aug. 14-21, 1999; Generating greater value from our products and pipeline. Aventis SA Company Presentation, Feb. 5, 2004], idraparinux [Harry R. Büller et al. *Blood*, 2006, 108, abstract 571 (ASH 2006)] and fondaparinux;

substances which inhibit the aggregation of platelets (platelet aggregation inhibitors, thrombocyte aggregation inhibitors), for example acetylsalicylic acid (for example aspirin), ticlopidine (ticlid), clopidogrel (plavix) and prasugrel;

fibrinogen receptor antagonists (glycoprotein-IIb/IIIa antagonists), for example abciximab, eptifibatide, tirofiban, lamifiban, lefradafiban and fradafiban;

and antiarrhythmics.

The present invention further relates to medicaments which comprise at least one inventive compound, normally together with one or more inert, nontoxic, pharmaceutically suitable excipients, and to the use thereof for the aforementioned purposes.

The inventive compounds can act systemically and/or locally. For this purpose, they can be administered in a suitable way, for example by the oral, parenteral, pulmonary, nasal, sublingual, lingual, buccal, rectal, dermal, transdermal, conjunctival, optic route or as implant or stent.

The inventive compounds can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay and control the release of the inventive compound), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration include preparations for injection and infusion in the form of solutions, suspensions, emulsions, lyophilizates or sterile powders.

Suitable for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The inventive compounds can be converted into the stated administration forms. This can take place in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colors (e.g. inorganic pigments, for example iron oxides) and masking flavors and/or odors.

It has generally been found to be advantageous, in the case of parenteral administration, to administer amounts of about 0.001 to 5 mg/kg, preferably about 0.01 to 1 mg/kg, of body weight to achieve effective results. In the case of oral administration, the dose is about 0.01 to 100 mg/kg, preferably about 0.01 to 20 mg/kg, and most preferably 0.1 to 10 mg/kg of body weight.

It may nevertheless be necessary in some cases to deviate from the stated amounts, in particular as a function of the body weight, route of administration, individual response to the active ingredient, nature of the preparation and time or interval over which administration takes place. For instance, less than the aforementioned minimum amount may be sufficient in some cases, whereas in other cases the stated upper limit must be exceeded. In the case of administration of larger amounts, it may be advisable to divide these into a plurality of individual doses over the day.

The following working examples illustrate the invention. The invention is not restricted to the examples.

The percentages in the following tests and examples are, unless stated otherwise, percentages by weight; parts are parts by weight. Solvent ratios, dilution ratios and concentration data for the liquid/liquid solutions are each based on volume.

A. EXAMPLES

Abbreviations approx. approximately
CDI carbonyldiimidazole
d day(s), doublet (in NMR)
TLC thin-layer chromatography
DCI direct chemical ionization (in MS)
dd doublet of doublets (in NMR)
DMAP 4-dimethylaminopyridine
DMF N,N-dimethylformamide
DMSO dimethyl sulfoxide
of theory of theory (in yield)
eq. equivalent(s)
ESI electrospray ionization (in MS)
h hour(s)
HPLC high pressure, high performance liquid chromatography
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
RP reversed phase (in HPLC)
RT room temperature
$R_t$ retention time (in HPLC)
s singulet (in NMR)
THF tetrahydrofuran

LC-MS and HPLC Methods

Method 1 (HPLC): Instrument: HP 1100 with DAD detection; column: Kromasil 100 RP-18, 60 mm×2.1 mm, 3.5 µm; mobile phase A: 5 ml of perchloric acid (70%)/l of water, mobile phase B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; column temperature: 30° C.; detection: UV 210 nm.

Method 2 (HPLC): Instrument: HP 1100 with DAD detection; column: Kromasil 100 RP-18, 60 mm×2.1 mm, 3.5 µm; mobile phase A: 5 ml of perchloric acid (70%)/l of water, mobile phase B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; detection: UV 210 nm.

Method 3 (LC-MS): MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC-MS): MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 5 (LC-MS): Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 6 (LC-MS): MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 7 (LC-MS): Instrument: Micromass Platform LCZ with HPLC Agilent Series 1100; column: Thermo Hypersil GOLD 3μ 20 mm×4 mm; mobile phase A: 1 l of water+0.5 ml of 50% formic acid, mobile phase B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 8 (LC-MS): MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% formic acid, mobile phase B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Method 9 (GC-MS): Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 1.7 min).

Method 10 (GC-MS): Instrument: Micromass GCT, GC6890; column: Restek RTX-35, 15 m×200 μm×0.33 μm; constant helium flow: 0.88 ml/min; oven: 70° C.; inlet: 250° C.; gradient: 70° C., 30° C./min→310° C. (hold for 3 min).

Method 11 (HPLC, enantiomer separation): column: Daicel Chiralpak AD-H, 5 μm, 250 mm×4.6 mm; eluent: 70:30 ethanol/isohexane; flow rate: 1 ml/min; temperature: 40° C.; UV detection: 220 nm.

Starting Compounds

Example 1A

5-Chloro-N-[(2S)-oxiran-2-ylmethyl]thiophene-2-carboxamide

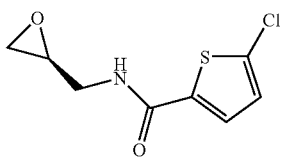

Example 1A is prepared as described in WO04/101557 (example 6A).

Example 2A 1-(2-Chloro-4-nitrophenyl)-3-methoxypyridin-2(1H)-one

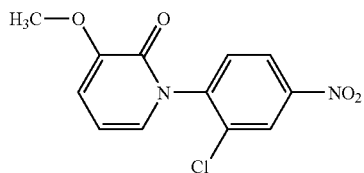

15 g (120 mmol) of 3-methoxypyridone are dissolved in 120 ml of anhydrous dimethyl sulfoxide and admixed with 16.1 g (144 mmol) of potassium tert-butoxide with stirring. After 30 min, 21.0 g (120 mmol) of 3-chloro-4-fluoronitrobenzene are added and the mixture is heated to 80° C. After 16 h, the mixture is allowed to cool, admixed with 1N hydrochloric acid and extracted repeatedly with dichloromethane. The combined dichloromethane phases are washed with water and saturated sodium chloride solution, dried over sodium sulfate, filtered and concentrated to dryness under reduced pressure. The resulting residue is stirred with tert-butyl methyl ether and filtered. The solid is dried under reduced pressure. 22.8 g (60% of theory) of the desired compound are obtained.

$^1$H NMR (400 MHz, DMSO-$d_6$, δ/ppm): 8.55 (d, 1H), 8.3 (dd, 1H), 7.85 (d, 1H), 7.15 (d, 1H), 6.9 (d, 1H), 6.3 (t, 1H), 3.65 (s, 3H).

HPLC (Method 4): $R_t$=1.80 min.

MS (ESIpos, m/z): 281 (M+H)$^+$.

Example 3A 1-(4-Amino-2-chlorophenyl)-3-methoxypyridin-2(1H)-one

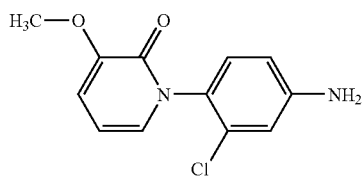

309 mg (0.72 mmol) of example 2A are dissolved in 7.5 ml of ethanol and admixed with 994 mg (4.41 mmol) of tin chloride dihydrate. The mixture is heated to reflux for 1 h and then the reaction is ended by adding 50 ml of water. Sodium hydroxide solution is used to adjust the pH to 10, and extraction is effected three times with ethyl acetate. The combined organic phases are dried over sodium sulfate. Subsequently, the mixture is filtered and the filtrate is freed of the solvent. The product is converted further without further purification.

$^1$H NMR (400 MHz, DMSO-$d_6$, δ/ppm): 7.05-6.94 (m, 2H), 6.84 (dd, 1H), 6.72 (d, 1H), 6.56 (dd, 1H), 6.17 (dd, 1H), 5.63 (br.s, 2H), 3.12 (s, 3H).

HPLC (Method 1): $R_t$=3.38 min

MS (DCI, m/z): 251 (M+H)$^+$..

Example 4A 1-(2-Chloro-4-nitrophenyl)-3-hydroxypyridin-2(1H)-one

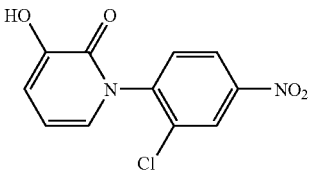

22.8 g (81 mmol) of example 2A are dissolved in 600 ml of anhydrous dichloromethane and cooled to 0° C. At this temperature, 203 ml (203 mmol) of a 1N boron tribromide solution in dichloromethane are added dropwise. The mixture is stirred at 0° C. for a further 2 h before it is diluted with water. The cooling is removed, the mixture is diluted with dichloromethane and the organic phase is removed. The water phase is extracted with dichloromethane; the combined organic phases are washed with saturated sodium chloride solution, dried over sodium sulfate, filtered and concentrated to dryness under reduced pressure. The residue is stirred with diisopropyl ether, filtered and dried under reduced pressure. This affords 17.8 g (82% of theory) of the desired compound.

$^1$H NMR (400 MHz, DMSO-d$_6$, δ/ppm): δ=9.55 (s, 1H), 8.6 (s, 1H), 8.35 (dd, 1H), 7.85 (d, 1H), 7.05 (d, 1H), 6.8 (d, 1H), 6.3 (t, 1H).

LC-MS (Method 4): R$_t$=1.48 min
MS (ESIpos): m/z=267 (M+H)$^+$

Example 5A 1-(2-Chloro-4-nitrophenyl)-3-(2-hydroxyethoxy)pyridin-2(1H)-one

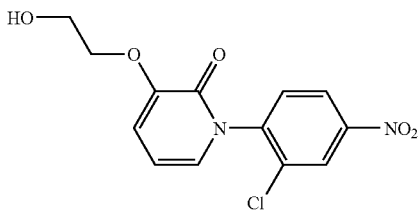

17.8 g (66.7 mmol) of example 4A are dissolved in 500 ml of anhydrous N,N-dimethylformamide and admixed with 18.5 g (134 mmol) of potassium carbonate. After 30 min, 13.1 g (100 mmol) of 2-bromethanol are added and the mixture is heated to 60° C. After 5 h, the mixture is cooled to RT and brought to pH 2 with 1N hydrochloric acid. The reaction solution is extracted repeatedly with dichloromethane and the combined organic phases are washed with saturated sodium chloride solution, dried over sodium sulfate, filtered and concentrated to dryness under reduced pressure. The residue is recrystallized from ethyl acetate, and the crystals are filtered off and dried under reduced pressure. This affords 13.4 g (65% of theory) of the desired compound.

$^1$H NMR (400 MHz, DMSO-d$_6$, δ/ppm): δ=8.5 (s, 1H), 8.35 (dd, 1H), 7.85 (d, 1H), 7.15 (d, 1H), 6.95 (d, 1H), 6.3 (t, 1H), 4.95 (t, 1H), 3.9 (m, 2H), 3.7 (m, 2H).

LC-MS (Method 4): R$_t$=1.83 min
MS (ESIpos): m/z=311 (M+H)$^+$

Example 6A 3-(2-{[tert-Butyl(diphenyl)silyl]oxy}ethoxy)-1-(2-chloro-4-nitrophenyl)pyridin-2(1H)-one

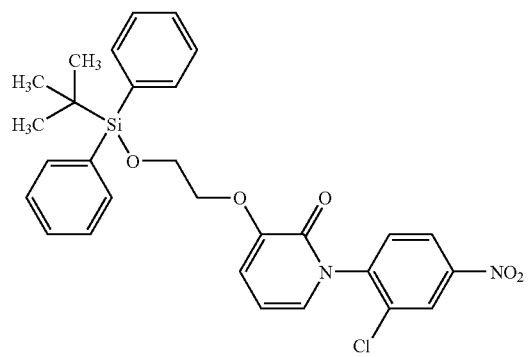

13.4 g (43.1 mmol) of example 5A are dissolved in 50 ml of anhydrous N,N-dimethylformamide and admixed with 3.5 g (52 mmol) of imidazole. At RT, 13.0 g (47 mmol) of tert-butyl(chloro)diphenylsilane are added dropwise. After the addition has ended, the mixture is stirred at RT for a further 4 h, then diluted with water, and the reaction solution is extracted repeatedly with ethyl acetate. The combined organic phases are washed twice with 1N hydrochloric acid and once with saturated sodium chloride solution, dried over sodium sulfate, filtered and concentrated to dryness under reduced pressure. The residue is dried under reduced pressure. This affords 25.4 g (91% of theory) of the desired compound.

$^1$H NMR (400 MHz, DMSO-d$_6$, δ/ppm): δ=8.55 (d, 1H), 8.35 (dd, 1H), 7.85 (d, 1H), 7.7 (m, 5H), 7.4 (m, 5H), 7.2 (d, 1H), 6.95 (d, 1H), 6.3 (t, 1H), 4.1 (m, 2H), 3.9 (m, 2H), 1.0 (s, 9H).

LC-MS (Method 4): R$_t$=3.12 min
MS (ESIpos): m/z=549 (M+H)$^+$

Example 7A 1-(4-Amino-2-chlorophenyl)-3-(2-{[tert-butyl(diphenyl)silyl]oxy}ethoxy)pyridin-2(1H)-one

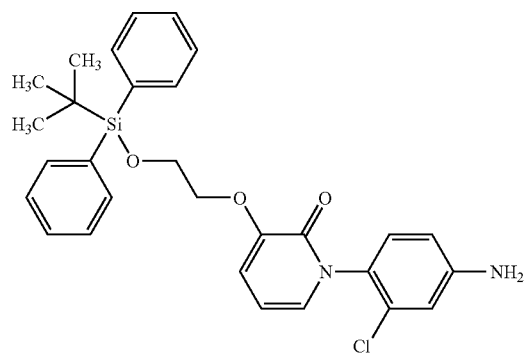

25.4 g (41.6 mmol) of example 6A are dissolved in 300 ml of tetrahydrofuran and admixed with 0.5 g of Raney Nickel.

5.2 g (104 mmol) of hydrazine hydrate are added and the reaction mixture is heated to 80° C. Vigorous evolution of gas sets in, which abates after 1 h. The same amounts of Raney Nickel and hydrazine hydrate are added again and the mixture is heated further. This is repeated twice until complete reduction. The mixture is then allowed to cool, filtered through silica gel and washed with tetrahydrofuran. The solution is concentrated to dryness under reduced pressure and the residue is dried under reduced pressure. This affords 20.0 g (93% of theory) of the desired compound.

$^1$H NMR (400 MHz, DMSO-d$_6$, δ/ppm): δ=7.7 (d, 4H), 7.45 (m, 6H), 7.2 (m, 2H), 6.9 (dd, 1H), 6.65 (d, 1H), 6.6 (dd, 1H), 6.15 (t, 1H), 5.65 (m, 2H), 4.1 (m, 2H), 3.95 (m, 2H), 1.0 (s, 9H).

LC-MS (Method 5): R$_t$=3.14 min
MS (ESIpos): m/z=519 (M+H)$^+$

Example 8A

N-[(2R)-3-({4-[3-(2-{[tert-Butyl(diphenyl)silyl]oxy}ethoxy)-2-oxopyridin-1(2H)-yl]-3-chlorophenyl}amino)-2-hydroxypropyl]-5-chlorothiophene-2-carboxamide 690 mg (1.33 mmol) of example 7A are dissolved in 10 ml of anhydrous acetonitrile and admixed at 0° C. with 318 mg (1.46 mmol) of example 1A. 445 mg (1.99 mmol) of magnesium perchlorate are added and the cooling is removed. After 6 h, another 318 mg (1.46 mmol) of example 1A are added and the mixture is stirred at RT for a further 16 h. The reaction solution is diluted with water and extracted repeatedly with ethyl acetate. The combined organic phases are dried over sodium sulfate, filtered and concentrated to dryness under reduced pressure, and the residue is dried under reduced pressure. This affords 1.4 g (99% of theory) of the desired compound.

LC-MS (Method 5): R$_t$=3.25 min
MS (ESIpos): m/z=736 (M+H)$^+$

Example 9A

N-[((5S)-3-{4-[3-(2-{[tert-Butyl(diphenyl)silyl]oxy}ethoxy)-2-oxopyridin-1(2H)-yl]-3-chlorophenyl}-2-oxo-1,3-oxazolidin-5-yl)methyl]-5-chlorothiophene-2-carboxamide

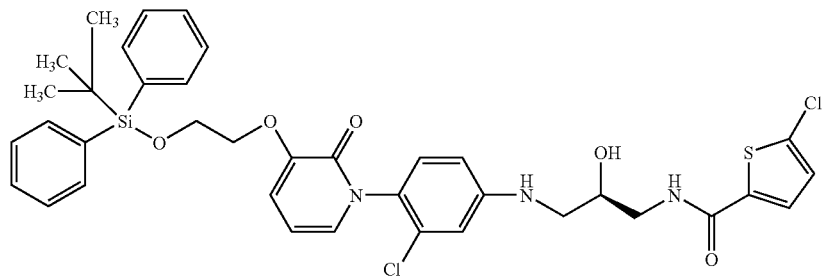

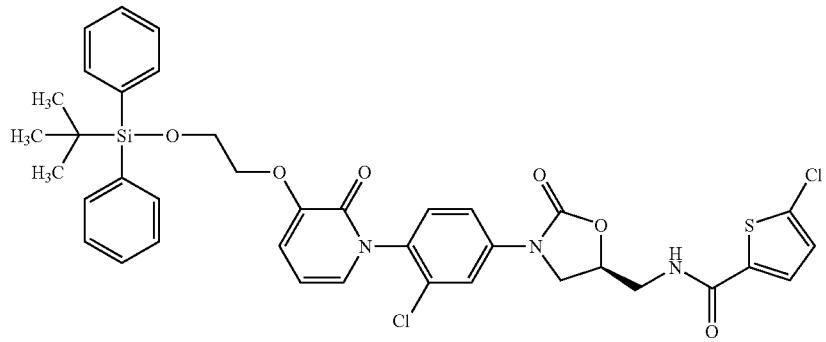

1.4 g (2 mmol) of example 8A are dissolved in 25 ml of anhydrous butyronitrile and admixed with 5 mg (0.04 mmol) of 4-dimethylaminopyridine and 658 mg (4.1 mmol) of N,N-carbonyldiimidazole. The mixture is heated to reflux for 5 h. The mixture is allowed to cool and diluted with 150 ml of dichloromethane. The organic phase is removed, washed with water and saturated sodium chloride solution, dried over sodium sulfate, filtered and concentrated to dryness under reduced pressure. The residue is dissolved in dimethyl sulfoxide and separated with preparative HPLC using a water/acetonitrile gradient. This affords 0.74 g (48% of theory) of the desired compound.

$^1$H NMR (400 MHz, DMSO-$d_6$, δ/ppm): δ=9.0 (t, 1H), 7.9 (d, 1H), 7.7 (m, 5H), 7.6 (m, 2H), 7.35-7.55 (m, 6H), 7.2 (d, 1H), 7.1 (dd, 1H), 6.9 (d, 1H), 6.2 (t, 1H), 4.9 (m, 1H), 4.3 (t, 1H), 4.1 (m, 2H), 3.95 (m, 2H), 3.9 (m, 1H), 3.6 (m, 2H), 1.0 (s, 9H).

LC-MS (Method 5): $R_t$=3.13 min
MS (ESIpos): m/z=762 (M+H)$^+$

Example 10A

3-Methoxy-1-(2-methyl-4-nitrophenyl)pyridin-2(1H)-one

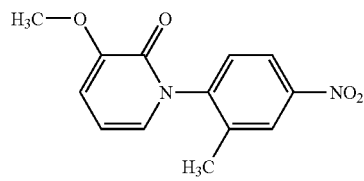

28.5 g (228 mol) of 3-methoxypyridin-2(1H)-one are dissolved in 850 ml of dimethyl sulfoxide and admixed at RT with 31 g (273 mmol) of potassium tert-butoxide. The suspension is stirred at RT for 30 min, before 35 g (228 mmol) of 1-fluoro-2-methyl-4-nitrobenzene are added, and the reaction solution is heated to 80° C. for 20 h. The mixture is then cautiously diluted with 1 l of water and brought to pH 1-2 with 1N hydrochloric acid. The solution is extracted repeatedly with dichloromethane. The combined organic extracts are washed with water and saturated sodium chloride solution, dried over sodium sulfate, filtered and concentrated under reduced pressure. The resulting solid is washed with a little tert-butyl methyl ether, filtered off and dried under reduced pressure. This affords 42.8 g (72% of theory) of the desired compound.

$^1$H NMR (400 MHz, DMSO-$d_6$, δ/ppm): δ=8.35 (d, 1H), 8.18 (dd, 1H), 7.57 (d, 1H), 7.13 (d, 1H), 6.95 (dd, 1H), 6.32 (t, 1H), 3.75 (s, 3H), 2.25 (s, 3H).

LC-MS (Method 3): $R_t$=1.45 min
MS (ESIpos): m/z=261 (M+H)$^+$

Example 11A

3-Hydroxy-1-(2-methyl-4-nitrophenyl)pyridin-2(1H)-one

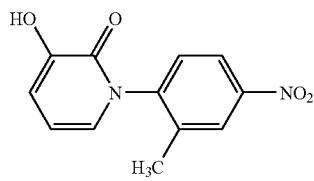

23.3 g (90 mmol) of example 10A are dissolved in 730 ml of anhydrous dichloromethane and cooled to 0° C. Within 10 minutes, 224 ml (224 mmol) of a 1N boron tribromide solution in dichloromethane are added dropwise, before stirring at this temperature for a further 1.5 h. The mixture is admixed with 200 ml of water and the water phase is extracted three times with dichloromethane. The combined organic phases are washed with saturated sodium chloride solution, dried over sodium sulfate and filtered. The solvent is removed under reduced pressure and the resulting solid is washed with tert-butyl methyl ether and filtered off. This affords 20.1 g (91% of theory) of the desired compound.

$^1$H NMR (400 MHz, DMSO-$d_6$, δ/ppm): δ=9.50 (s, 1H), 8.42 (d, 1H), 8.20 (dd, 1H), 7.6 (d, 1H), 7.05 (d, 1H), 6.85 (dd, 1H), 6.25 (t, 1H), 2.25 (s, 3H).

LC-MS (Method 3): $R_t$=1.45 min
MS (ESIpos): m/z=246 (M+H)$^+$

Example 12A

3-[(2-Methoxyethoxy)methoxy]-1-(2-methyl-4-nitrophenyl)pyridin-2(1H)-one

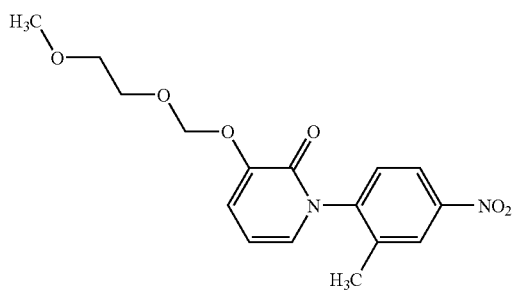

10.0 g (41 mmol) of example 11A are dissolved in anhydrous dichloromethane and admixed with 13.6 g (89 mmol) of 1,8-diazabicyclo(5.4.0)undec-7-ene. To this solution are added, at 25° C., slowly and in portions, 8.6 g (69 mmol) of 1-(chloromethoxy)-2-methoxyethane. After a further hour, the solution is filtered through silica gel and concentrated to dryness under reduced pressure. This affords 20.1 g (91% of theory) of the desired compound.

$^1$H NMR (400 MHz, DMSO-$d_6$, δ/ppm): δ=8.32 (d, 1H), 8.19 (dd, 1H), 7.6 (d, 1H), 7.22 (dd, 1H), 7.15 (dd, 1H), 6.3 (t, 1H), 5.25 (s, 2H), 3.78-3.72 (m, 2H), 3.51-3.45 (m, 2H), 3.23 (s, 3H), 2.15 (s, 3H).

LC-MS (Method 3): $R_t$=1.79 min
MS (ESIpos): m/z=335 (M+H)$^+$

Example 13A

1-(4-Amino-2-methylphenyl)-3-[(2-methoxyethoxy)methoxy]pyridin-2(1H)-one

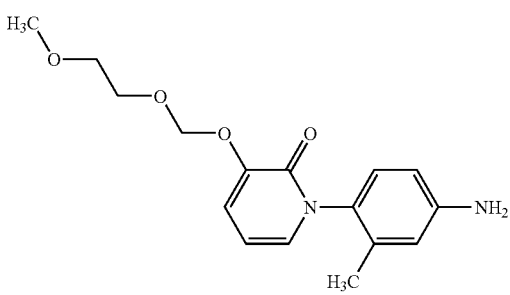

12 g (36 mmol) of example 12A are dissolved in 1.2 l of a 1:1 mixture of ethyl acetate and ethanol, and admixed with 0.1 equivalent of palladium on carbon and with 11.3 g (180 mmol) of ammonium formate. The mixture is heated to 80° C. for 2 hours. The mixture is allowed to cool and filtered through silica gel, and the solvent is removed under reduced pressure. This affords 10.6 g (88% of theory) of the desired compound.

$^1$H NMR (400 MHz, DMSO-d$_6$, δ/ppm): δ=7.12-7.05 (m, 1H), 6.80 (d, 1H), 6.51-6.42 (m, 2H), 6.17 (t, 1H), 5.21 (s, 2H), 3.76-3.71 (m, 2H), 3.49-3.45 (m, 2H), 3.23 (s, 3H), 1.85 (s, 3H).

LC-MS (Method 3): R$_t$=1.10 min
MS (ESIpos): m/z=305 (M+H)$^+$

Example 14A

5-Chloro-N-[((5S)-3-{4-[3-[(2-methoxyethoxy)methoxy]-2-oxopyridin-1(2H)-yl]-3-methylphenyl}-2-oxo-1,3-oxazolidin-5-yl)methyl]thiophene-2-carboxamide

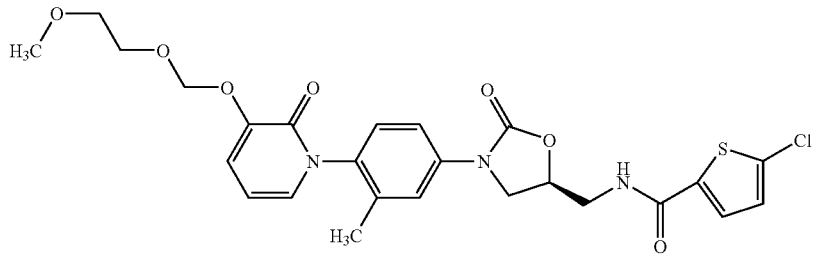

9.2 g (30 mmol) of example 13A are dissolved in 580 ml of acetonitrile and cooled to 0° C. At this temperature, 7.3 g (34 mmol) of example 1A are added and then the mixture is stirred for a further 10 minutes. The mixture is admixed with 10.2 g (46 mmol) of magnesium perchlorate, the cooling is removed and stirring is continued for a further 17 hours. Then 14.8 g (91 mmol) of carbonyldiimidazole and 0.37 g (3 mmol) of N,N-4-dimethylaminopyridine are added, and the mixture is heated to 60° C. for 4 h. After cooling, the mixture is stirred at RT for a further 16 h and then concentrated to dryness under reduced pressure. The residue is admixed with 1N hydrochloric acid and ethyl acetate, and stirred vigorously. After 15 min, the phases are separated, the aqueous phase is extracted three times with ethyl acetate, and the organic phases are combined. After washing with saturated sodium chloride solution, the product is dried and concentrated to dryness under reduced pressure. This affords 17.2 g (95% of theory) of the desired compound.

$^1$H NMR (400 MHz, DMSO-d$_6$, δ/ppm): δ=9.0 (t, 1H), 7.70 (d, 1H), 7.56-7.49 (m, 2H), 7.26 (d, 1H), 7.20 (d, 1H), 6.95 (dd, 1H), 6.80 (dd, 1H), 6.20 (t, 1H), 4.90-4.81 (m, 1H), 4.24 (t, 1H), 3.92-3.85 (m, 1H), 3.70-3.55 (m, 3H), 3.52-3.25 (m, 2H), 2.55 (s, 3H), 2.08-2.02 (m, 3H), 1.9 (s, 3H).

LC-MS (Method 4): R$_t$=2.13 min
MS (ESIpos): m/z=548 (M+H)$^+$

Example 15A

5-Chloro-N-({(5S)-3-[4-(3-hydroxy-2-oxopyridin-1(2H)-yl)-3-methylphenyl]-2-oxo-1,3-oxazolidin-5-yl}methyl)thiophene-2-carboxamide

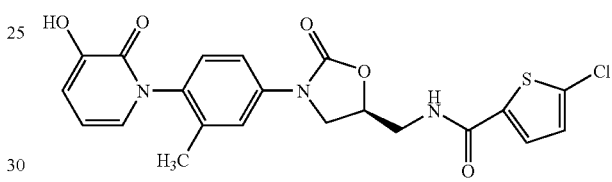

18 g (33 mmol) of example 14A are dissolved in 50 ml of trifluoroacetic acid and stirred for a further 3 h before concentrating to dryness under reduced pressure. The residue (22.3 g) is dissolved in portions, each of 2 g, in 8.5 ml of dimethyl sulfoxide each time, and purified by preparative HPLC with a water/acetonitrile gradient. The product fractions are combined and freed of acetonitrile, and the crystals formed are filtered off. The filtrate is extracted with ethyl acetate, and the ethyl acetate phases are combined and washed with saturated sodium chloride solution, dried and concentrated under reduced pressure. The residue is combined with the crystals and dried under reduced pressure. This affords 9.95 g (65% of theory) of the desired compound.

$^1$H NMR (400 MHz, DMSO-d$_6$, δ/ppm): δ=9.2 (br. s, 1H), 9.00 (t, 1H), 7.70 (d, 1H), 7.56-7.48 (m, 2H), 7.26 (d, 1H), 7.20 (d, 1H), 6.95 (dd, 1H), 6.86 (dd, 1H), 6.2 (t, 1H), 4.92-4.80 (m, 1H), 4.22 (t, 1H), 3.92-3.82 (m, 1H), 3.62 (t, 2H), 2.04 (s, 3H).

LC-MS (Method 4) R$_t$=2.09 min
MS (ESIpos): m/z=460 (M+H)$^+$

Example 16A 1-(4-Amino-2-methylphenyl)-3-methoxypyridin-2(1H)-one

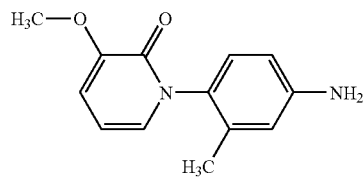

188 mg (0.724 mmol) of example 10A are dissolved in 10 ml of ethanol and admixed with 654 g (2.89 mmol) of tin chloride dihydrate. The mixture is heated to reflux for 1 h, then cooled and diluted with 50 ml of water. Sodium hydroxide solution is used to adjust the pH to 10, and the mixture is then extracted three times with ethyl acetate. The combined organic phases are dried over sodium sulfate. After filtration, the filtrate is freed of the solvent. The reaction product is converted without further purification.

$^1$H NMR (400 MHz, DMSO-$d_6$, δ/ppm): 6.96 (dd, 1H), 6.85 (dd, 1H), 6.77 (d, 1H), 6.49-6.41 (m, 2H), 6.16 (dd, 1H), 5.21 (br.s, 2H), 3.72 (s, 3H), 1.84 (s, 3H).

LC-MS (Method 2): $R_t$=2.70 min.

MS (ESIpos, m/z): 231 (M+H)$^+$.

Example 17A 1-(2,6-Dimethyl-4-nitrophenyl)-3-methoxypyridin-2(1H)-one

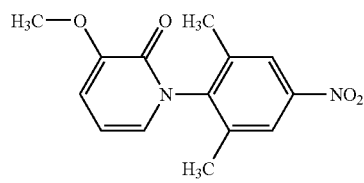

336 mg (2.69 mmol) of 3-methoxypyridinone in 10 ml of DMF are admixed at 0° C. with 452 mg (4.03 mmol) of potassium tert-butoxide, and the mixture is stirred at room temperature for 30 min. 500 mg (2.96 mmol) of 1-fluoro-2,5-dimethyl-4-nitrobenzene are added and the mixture is stirred at 80° C. After 22 h, the mixture is heated to 120° C. and stirred for a further 20 h. Then the mixture is cooled and added to 100 ml of water and 15 ml of saturated aqueous sodium chloride solution. Extraction is effected three times with 300 ml each time of ethyl acetate, and the combined organic phases are dried over sodium sulfate. After filtration, the solvents are removed under reduced pressure and the residue is purified by chromatography on silica gel (1:1 cyclohexane/ethyl acetate). This affords 383 mg (52% of theory) of the desired compound.

$^1$H NMR (300 MHz, DMSO-$d_6$, δ/ppm): 8.16 (s, 2H), 7.04 (dd, 1H), 6.97 (dd, 1H), 6.38 (dd, 1H), 3.77 (s, 3H), 2.08 (s, 6H).

HPLC (Method 1): $R_t$=2.84 min.

MS (DCI, m/z): 275 (M+H)$^+$.

Example 18A 1-(4-Amino-2,6-dimethylphenyl)-3-methoxypyridin-2(1H)-one

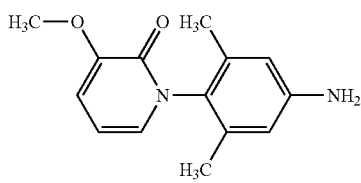

300 mg (1.09 mmol) of example 17A are dissolved in 20 ml of ethanol and admixed with 987 g (4.38 mmol) of tin chloride dihydrate. The mixture is heated to reflux for 1 h, then cooled and diluted with 150 ml of water. Sodium hydroxide solution is used to adjust the pH to 10, and then the mixture is extracted three times with ethyl acetate. The combined organic phases are dried over sodium sulfate. After filtration, the filtrate is freed of the solvent. The reaction product (204 mg) is converted without further purification.

$^1$H NMR (300 MHz, DMSO-$d_6$, δ/ppm): 6.93-6.83 (m, 2H), 6.33 (s, 2H), 6.19 (dd, 1H), 5.12 (br.s, 2H), 3.72 (s, 3H), 1.78 (s, 6H).

LC-MS (Method 1): $R_t$=2.90 min.

MS (DCI, m/z): 245 (M+H)$^+$.

Example 19A 1-(2,6-Dimethyl-4-nitrophenyl)-3-hydroxypyridin-2(1H)-one

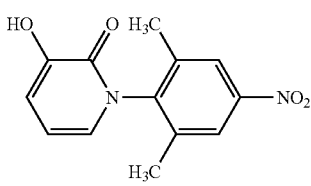

1.95 g (7.11 mmol) of example 17A in 30 ml of dichloromethane are admixed at 0° C. with 17.7 ml (17.7 mmol) of a 1 molar solution of boron tribromide in dichloromethane. After 2.5 h the mixture is cooled and diluted with 150 ml of dichloromethane. Subsequently, the mixture is admixed cautiously with 150 ml of water and stirred for 10 min. After phase separation, the aqueous phase is washed with dichloromethane. The combined organic phases are washed with saturated aqueous sodium chloride solution and then dried over sodium sulfate. After filtration, the solvents are removed under reduced pressure. The reaction product thus obtained (1.85 g) is converted without further purification.

$^1$H NMR (400 MHz, DMSO-$d_6$, δ/ppm): 9.45 (s, 1H), 8.16 (s, 2H), 6.94 (dd, 1H), 6.86 (dd, 1H), 6.31 (dd, 1H), 2.10 (s, 6H).

LC-MS (Method 3): $R_t$=1.58 min.

MS (ESIpos, m/z): 261 (M+H)$^+$.

Example 20A 1-(2,6-Dimethyl-4-nitrophenyl)-3-[(2-methoxyethoxy)methoxy]pyridin-2(1H)-one

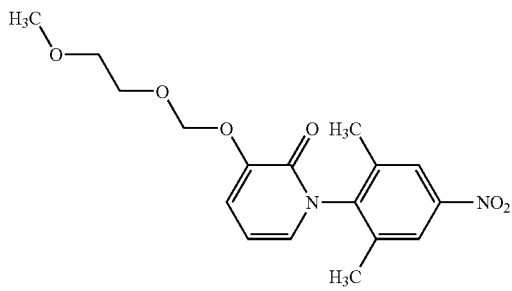

1.37 g (5.28 mmol) of example 19A in 60 ml of dichloromethane and 1.73 ml (11.6 mmol) of 1,8-diazabicyclo (5.4.0)undec-7-ene are admixed at 0° C. with a solution of 1.12 g (8.97 mmol) of methoxyethoxymethyl chloride in 15 ml of dichloromethane. The mixture is stirred at RT for 1 h. The solvents are removed under reduced pressure and the resulting reaction product is purified by chromatography on silica:gel (2:1 cyclohexane/ethyl acetate). This affords 1.02 g (55% of theory) of the desired compound.

$^1$H NMR (400 MHz, DMSO-d$_6$, δ/ppm): 8.16 (s, 2H), 7.22-7.13 (m, 2H), 6.37 (dd, 1H), 5.26 (s, 2H), 3.79-3.73 (m, 2H), 3.50-3.45 (m, 2H), 3.31 (s, 3H), 2.10 (s, 6H).

HPLC (Method 1): R=3.85 min.
MS (ESIpos, m/z): 349 (M+H)$^+$.

Example 21A 1-(4-Amino-2,6-dimethylphenyl)-3-[(2-methoxyethoxy)methoxy]pyridin-2(1H)-one

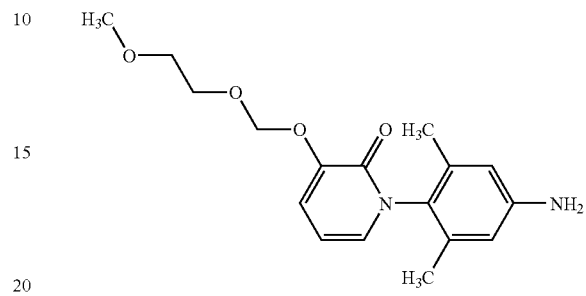

1.00 g (2.81 mmol) of example 20A in 14 ml of ethanol is admixed with 905 mg (14.4 mmol) of ammonium formate and 50 mg of palladium on carbon. The mixture is stirred at 90° C. for 2 h. After cooling, the mixture is filtered with suction through kieselguhr and rinsed twice with ethanol. The solvents of the collected filtrates are removed under reduced pressure. The resulting reaction product (895 mg) is converted without further purification.

LC-MS (Method 6): R$_t$=1.42 min.
MS (ESIpos, m/z): 319 (M+H)$^+$.

Example 22A

5-Chloro-N-{[(5S)-3-(4-{3-[(2-methoxyethoxy)methoxy]-2-oxopyridin-1(2H)-yl}-3-methylphenyl)-2-oxo-1,3-oxazolidin-5-yl]methyl}thiophene-2-carboxamide

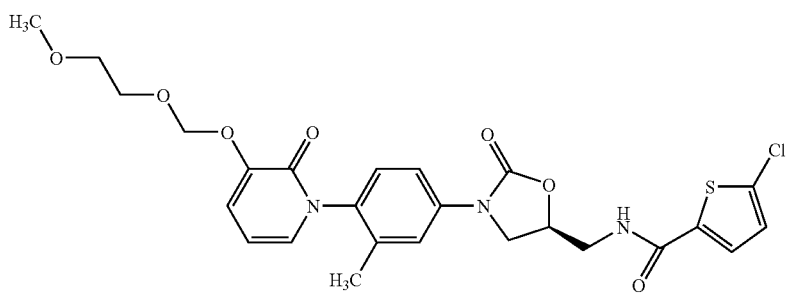

A solution of 875 mg (2.75 mmol) of the product from example 21A in 50 ml of acetonitrile is admixed with 658 mg (3.03 mmol) of the product from example 1A. To the suspension are added 921 mg (4.13 mmol) of magnesium perchlorate, after which the mixture is left to stir at RT for 6.5 h. Then 1.15 g (6.88 mmol) of 1,1'-carbonyldiimidazole and 33 mg (0.28 mmol) of DMAP are added, and the mixture is stirred at RT. After 17 h, the mixture is diluted with 140 ml of water and 100 ml of ethyl acetate. The water phase is extracted twice with ethyl acetate and the combined organic phases are dried over sodium sulfate. After filtration, the mixture is freed of the solvent and the residue is purified by chromatography on silica gel (40:1→20:1 dichloromethane/ethanol). After removing the solvent, 853 mg (50% of theory) of the desired product are obtained.

HPLC (Method 1): $R_t$=4.11 min.
MS (ESIpos, m/z): 562 (M+H)$^+$.

Example 23A

5-Chloro-N-({(5S)-3-[4-(3-hydroxy-2-oxopyridin-1(2H)-yl-3,5-dimethylphenyl]-2-oxo-1,3-oxazolidin-5-yl}methyl)thiophene-2-carboxamide

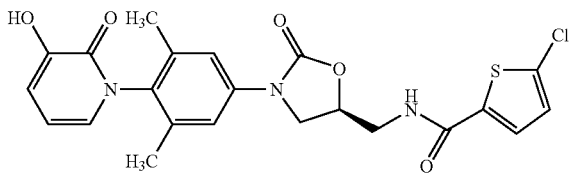

To a solution of 750 mg (1.33 mmol) of the product from example 22A in 3 ml of dichloromethane are slowly added dropwise, at 0° C., 13.3 ml (173 mmol) of trifluoroacetic acid. After 5 h at 0° C., the mixture is diluted with 200 ml of water and 80 ml of ethyl acetate. Sodium hydrogen carbonate is then used to adjust the pH to 6 and the phases are separated. The water phase is extracted twice with ethyl acetate and the combined organic phases are dried over sodium sulfate. After filtration, the mixture is freed of the solvent. This affords 652 mg (100% of theory) of the desired product.

$^1$H NMR (400 MHz, DMSO-d$_6$, δ/ppm): 9.25 (s, 1H), 8.98 (t, 1H), 7.70 (d, 1H), 7.39 (dd, 2H), 7.20 (d, 1H), 6.84 (dd, 1H), 6.24 (dd, 1H), 4.91-4.80 (m, 1H), 4.21 (dd, 1H), 3.90-3.83 (m, 1H), 3.70-3.57 (m, 2H), 1.97 (s, 6H).

HPLC (Method 1): $R_t$=4.09 min.
MS (DCI, m/z): 474 (M+H)$^+$.

Example 24A

1-[2-(Difluoromethoxy)-4-nitrophenyl]-3-methoxy-pyridin-2(1H)-one

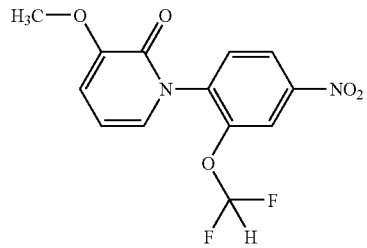

302 mg (2.41 mmol) of 3-methoxypyridone are dissolved in 8.2 ml of anhydrous dimethyl sulfoxide and admixed with 325 mg (2.89 mmol) of potassium tert-butoxide. After 30 min, 500 mg (2.41 mmol) of 2-(difluoromethoxy)-1-fluoro-4-nitrobenzene are added and the mixture is heated to 80° C. for 20 h. The reaction solution is diluted with dichloromethane and washed with water and 1N hydrochloric acid. After the organic phase has been dried over sodium sulfate, it is filtered and concentrated to dryness under reduced pressure. The residue is dissolved in dimethyl sulfoxide and purified by preparative HPLC with a water/acetonitrile gradient. The product fractions are combined and concentrated to dryness under reduced pressure. This affords 207 mg (28% of theory) of the desired product.

$^1$H NMR (400 MHz, DMSO-d$_6$, δ/ppm): δ=8.3 (dd, 1H), 8.2 (d, 1H), 7.8 (d, 1H), 7.4 (t, 1H), 7.2 (d, 1H), 6.9 (d, 1H), 6.3 (t, 1H), 3.75 (s, 3H).

LC-MS (Method 4): $R_t$=1.83 min
MS (ESIpos): m/z=313 (M+H)$^+$

Example 25A

1-[4-Amino-2-(difluoromethoxy)phenyl]-3-methoxypyridin-2(1H)-one

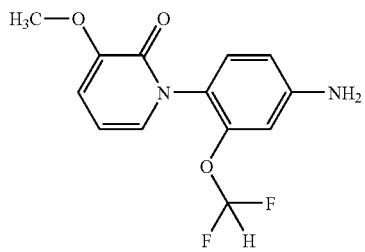

200 mg (0.641 mmol) of example are dissolved in 20 ml of a 1:1 mixture of ethanol and ethyl acetate, and admixed with 202 mg (3.20 mmol) of ammonium formate and 50 mg of palladium on carbon. The mixture is heated to 80° C. After 1 h, it is allowed to cool and filtered through silica gel. Then it is washed with a 1:1 mixture of ethanol and ethyl acetate, and the filtrate is concentrated to dryness under reduced pressure. This affords 190 mg (100% of theory) of the desired product.

$^1$H NMR (400 MHz, DMSO-d$_6$, δ/ppm): δ=6.75-7.15 (m, 4H), 6.5 (s, 2H), 6.2 (t, 1H), 5.65 (m, 2H), 3.7 (s, 3H).

LC-MS (Method 3): $R_t$=1.30 min
MS (ESIpos): m/z=283 (M+H)$^+$

Example 26A 2-(Bromomethyl)-1-fluoro-4-nitrobenzene

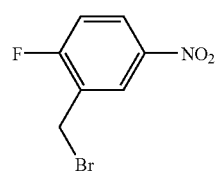

186 g (1.2 mol) of 2-fluoro-5-nitrotoluene are dissolved in 1.2 l of tetrachloromethane and admixed with 214 g (1.20 mol) of N-bromosuccinimide. 19.7 g (120 mmol) of azodiisobutyronitrile are added and the mixture is heated under reflux. After 16 h, the mixture is allowed to cool, filtered and concentrated to dryness under reduced pressure. The residue is dissolved in 300 ml of dichloromethane and admixed with 300 g of Seesand. Then the mixture is concentrated to dryness under reduced pressure again, and the residue is applied to a 1 kg silica gel column. It is chromatographed with a 20:1 mixture of cyclohexane and ethyl acetate, and the product fractions are concentrated to dryness under reduced pressure. The residue is crystallized with cyclohexane and dried under reduced pressure. This affords 92 g (32% of theory) of the desired product.

$^1$H NMR (400 MHz, DMSO-d$_6$, δ/ppm): δ=8.57-8.52 (m, 1H), 8.33-8.27 (m, 1H), 7.56 (t, 1H), 4.62 (s, 2H).

GC-MS (Method 9): R$_t$=7.79 min
MS (ESIpos): m/z=154 (M–Br)$^+$

Example 27A

1-Fluoro-2-(methoxymethyl)-4-nitrobenzene

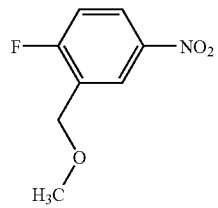

30 g (128 mmol) of the compound from example 26A are dissolved in 1.3 l of anhydrous toluene and admixed with 45 g (192 mmol) of silver(I) oxide and 24.6 g (769 mmol) of anhydrous methanol. The mixture is heated to 60° C. for 16 h. It is then allowed to cool and filtered through silica gel. The product is fractionally eluted with a gradient of cyclohexane and 25:1 cyclohexane/ethyl acetate. The product fractions are concentrated to dryness under reduced pressure and dried under reduced pressure. This affords 17 g (72% of theory) of the desired product.

$^1$H NMR (400 MHz, DMSO-d$_6$, δ/ppm): δ=8.41-8.36 (m, 1H), 8.22-8.16 (m, 1H), 7.26 (t, 1H), 4.58 (s, 2H), 3.49 (s, 3H).

GC-MS (Method 9): Rt=6.52 min
MS (ESIpos): m/z=154 (M–OCH$_3$)$^+$

Example 28A

3-Methoxy-1-[2-(methoxymethyl)-4-nitrophenyl]pyridin-2(1H)-one

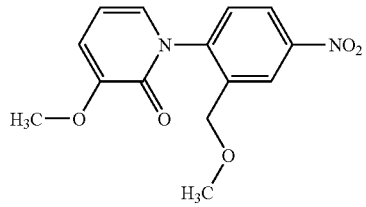

1.69 g (13.5 mmol) of 3-methoxypyridone are dissolved in 50 ml of anhydrous dimethyl sulfoxide and admixed with 1.82 g (16.2 mmol) of potassium tert-butoxide. After 1 h, 2.5 g (13.5 mmol) of example 27A dissolved in 10 ml of anhydrous dimethyl sulfoxide are added, and the mixture is heated to 80° C. for 3 h. The reaction solution is allowed to cool and left to stand for a further 48 h, before being diluted with ethyl acetate and washed with water and 1N hydrochloric acid. The organic phase is dried over magnesium sulfate, filtered and concentrated to dryness under reduced pressure. The residue is admixed with tert-butyl methyl ether, and the crystals which separate out are filtered off and dried under reduced pressure. This affords 2.05 g (52% of theory) of the desired product.

$^1$H NMR (400 MHz, DMSO-d$_6$, δ/ppm): δ=8.45 (d, 1H), 8.25 (dd, 1H), 7.6 (d, 1H), 7.15 (d, 1H), 6.9 (d, 1H), 6.3 (t, 1H), 4.25 (q, 2H), 3.75 (s, 3H) 3.2 (s, 3H).

LC-MS (Method 4): R$_t$=1.82 min
MS (ESIpos): m/z=291 (M+H)$^+$

Example 29A

1-[4-Amino-2-(methoxymethyl)phenyl]-3-methoxypyridin-2(1H)-one

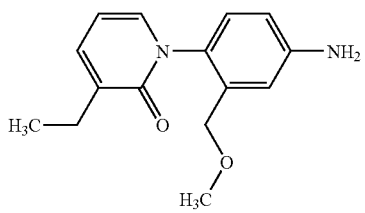

2.00 g (6.89 mmol) of example 28A are dissolved in 140 ml of a 1:1 mixture of ethanol and ethyl acetate, and admixed with 2.17 g (34.4 mmol) of ammonium formate and 200 mg of palladium on carbon. The mixture is heated to 80° C. After 30 min, it is allowed to cool and filtered through silica gel. It is washed with a 1:1 mixture of ethanol and ethyl acetate, and the filtrate is concentrated to dryness under reduced pressure. This affords 1.90 g (99% of theory) of the desired product.

LC-MS (Method 4): R$_t$=1.34 min
MS (ESIpos): m/z=261 (M+H)$^+$

Example 30A

1-[2-(Methoxymethyl)-4-nitrophenyl]-3-methylpyridin-2(1H)-one

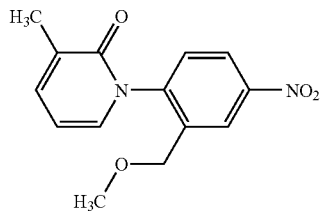

1.47 g (13.5 mmol) of 3-methyl-2-pyridone are dissolved in 50 ml of anhydrous dimethyl sulfoxide and admixed with 1.82 g (16.2 mmol) of potassium tert-butoxide. After 1 h, 2.5 g (13.5 mmol) of example 27A dissolved in 10 ml of anhydrous dimethyl sulfoxide are added, and the mixture is heated to 80° C. for 3 h. It is left to cool and stand for a further 48 h, before the reaction solution is diluted with ethyl acetate and washed with water and 1N hydrochloric acid. The organic phase is dried over magnesium sulfate, filtered and concentrated to dryness under reduced pressure. The residue is applied to silica gel and separated on silica gel with a mixture of 1:1 cyclohexane and ethyl acetate. The product fractions are combined and concentrated to dryness under reduced pressure. This affords 2.05 g (55% of theory) of the desired product.

$^1$H NMR (400 MHz, DMSO-$d_6$, δ/ppm): δ=8.45 (d, 1H), 8.25 (dd, 1H), 7.6 (d, 1H), 7.4 (m, 2H), 6.3 (t, 1H), 4.4-4.1 (q, 2H), 3.25 (s, 3H) 2.05 (s, 3H).

Example 31A

1-[4-Amino-2-(methoxymethyl)phenyl]-3-methylpyridin-2(1H)-one

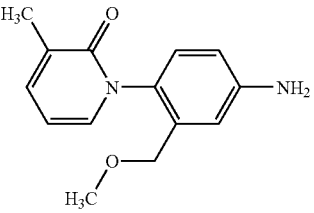

2.00 g (7.29 mmol) of example 30A are dissolved in 150 ml of a 1:1 mixture of ethanol and ethyl acetate, and admixed with 2.60 g (36.5 mmol) of ammonium formate and 200 mg of palladium on carbon. The mixture is heated to 80° C. After 30 min, it is allowed to cool and filtered through silica gel. It is washed with a 1:1 mixture of ethanol and ethyl acetate, and the filtrate is concentrated to dryness under reduced pressure. This affords 1.81 g (99% of theory) of the desired product.

LC-MS (Method 4): R=1.47 min
MS (ESIpos): m/z=245 (M+H)$^+$

Example 32A 2-(Ethoxymethyl)-1-fluoro-4-nitrobenzene

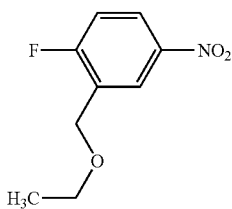

15 g (64.1 mmol) of example 26A are dissolved in 500 ml of anhydrous toluene and admixed with 22.3 g (96.1 mmol) of silver(I) oxide and 187 ml (3.20 mol) of anhydrous ethanol. After 96 h at 60° C., the mixture is allowed to cool and filtered through silica gel. It is washed with toluene, and the filtrate is concentrated to dryness under reduced pressure. The residue is purified by preparative HPLC with a gradient of water and acetonitrile. The product fractions are combined and concentrated to dryness under reduced pressure. This affords 3.0 g (24% of theory) of the desired product.

$^1$H NMR (400 MHz, DMSO-$d_6$, δ/ppm): δ=8.45 (m, 1H), 8.25 (m, 1H), 7.5 (t, 1H), 4.6 (s, 2H), 3.55 (q, 2H), 1.2 (t, 3H).
GC-MS (Method 9): R$_f$=6.91 min
MS (ESIpos): m/z=154 (M−OC$_2$H$_5$)$^+$ Example 33A 1-[2-(Ethoxymethyl)-4-nitrophenyl]-3-methylpyridin-2(1H)-one

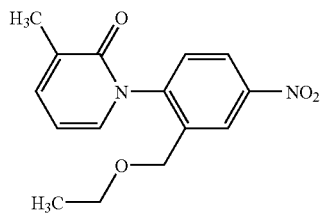

273 mg (2.51 mmol) of 3-methyl-2-pyridone are dissolved in 10 ml of anhydrous dimethyl sulfoxide and admixed with 338 g (3.01 mmol) of potassium tert-butoxide. After 1 h, 500 mg (2.51 mmol) of example 32A are added, and the mixture is heated to 80° C. for 16 h. The mixture is allowed to cool and admixed with saturated sodium chloride solution. The mixture is extracted repeatedly with dichloromethane, and the organic phase is washed twice with water and twice with saturated sodium chloride solution, dried over sodium sulfate, filtered and concentrated to dryness under reduced pressure. The residue is dissolved in 5 ml of dimethyl sulfoxide and purified by preparative HPLC with a gradient of water and acetonitrile. The product fractions are combined and concentrated to dryness under reduced pressure. This affords 430 mg (59% of theory) of the desired product.

$^1$H NMR (400 MHz, DMSO-$d_6$, δ/ppm): δ=8.4 (d, 1H), 8.3 (dd, 1H), 7.6 (d, 1H), 7.45 (m, 2H), 6.3 (t, 1H), 4.4-4.1 (q, 2H), 3.4 (m, 2H) 2.05 (s, 3H), 1.1 (t, 3H).
LC-MS (Method 4) R$_f$=2.04 min
MS (ESIpos): m/z=289 (M+H)$^+$ Example 34A 1-[4-Amino-2-(ethoxymethyl)phenyl]-3-methylpyridin-2(1H)-one

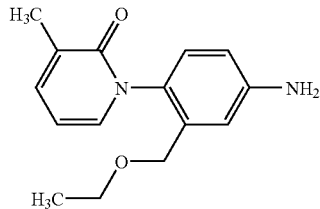

425 mg (1.47 mmol) of example 33A are dissolved in 30 ml of a 1:1 mixture of ethanol and ethyl acetate, and admixed with 465 mg (7.37 mmol) of ammonium formate and 50 mg of palladium on carbon. The mixture is heated to 80° C. After 30 min, it is allowed to cool and filtered through silica gel. It is washed with ethyl acetate, and the filtrate is concentrated to dryness under reduced pressure. This affords 388 mg (99% of theory) of the desired product.

LC-MS (Method 4): R$_f$=1.28 min
MS (ESIpos): m/z=259 (M+H)$^+$

Example 35A (2-Fluoro-5-nitrobenzyl)(triphenyl)phosphonium Bromide

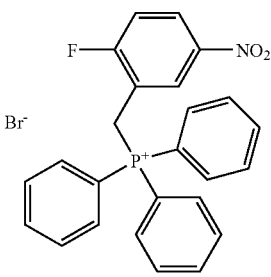

20 g (85.5 mmol) of the compound from example 26A are dissolved in 250 ml of anhydrous toluene and admixed with 22.4 g (85.5 mmol) of triphenylphosphine. The solution is heated under reflux for 16 h, in the course of which a precipitate separates out. The mixture is allowed to cool and the precipitate is filtered off. After washing with diethyl ether, it is dried under reduced pressure. This affords 39 g (92% of theory) of the desired product.

$^1$H NMR (400 MHz, DMSO-$d_6$, δ/ppm): δ=8.30-8.23 (m, 1H), 7.98-7.88 (m, 4H), 7.81-7.70 (m, 12H), 7.45 (t, 1H), 5.32 (d, 2H).

Example 36A

1-Fluoro-4-nitro-2-[prop-1-en-1-yl]benzene

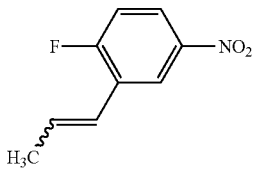

At 10° C., 5.99 g (32.7 mmol) of sodium bis(trimethylsilyl)amide are added dropwise to a solution of 13.5 g (27.3 mmol) of the compound from example 35A in 145 ml of dioxane. The mixture is stirred at this temperature for 1 h. Then a solution of 2.40 g (54.5 mmol) of acetaldehyde in 5 ml of dioxane is added and the mixture is stirred at RT for 1 h, then admixed with 400 ml of water and extracted three times with dichloromethane, and the combined organic phases are washed twice with saturated aqueous sodium chloride solution. After drying over sodium sulfate and subsequent filtration, the solvent is removed under reduced pressure. It is purified by means of chromatography on silica gel (eluent: cyclohexane/ethyl acetate=40:1). This affords 5.2 g (100% of theory) of the desired product as an E/Z isomer mixture.

$^1$H NMR (400 MHz, DMSO-$d_6$, δ/ppm): δ=8.47-8.05 (m, 2H), 7.58-7.42 (m, 1H), 6.70-6.05 (m, 2H), 1.90-1.78 (m, 3H).

GC-MS (Method 10): $R_t$=2.64 and 2.70 min

MS (ESIpos): m/z=181 (M+H$^+$)$^+$

Example 37A

1-{4-Nitro-2-[prop-1-en-1-yl]phenyl}pyridin-2(1H)-one

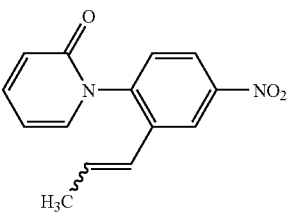

223 mg (2.35 mmol) of pyridin-2(1H)-one are dissolved in 10 ml of anhydrous dimethyl sulfoxide and admixed with 315 mg (2.82 mmol) of potassium tert-butoxide. After 1 h, 500 mg (2.76 mmol) of example 36A are added and the mixture is heated to 80° C. for 15 h. The mixture is allowed to cool and diluted with water and saturated sodium chloride solution. The solution is extracted repeatedly with dichloromethane. The combined organic phases are washed with water and with saturated sodium chloride solution, dried over sodium sulfate, filtered and concentrated to dryness under reduced pressure. The residue is purified by preparative HPLC with a gradient of water and acetonitrile. The product fractions are combined and concentrated to dryness under reduced pressure. This affords 103 mg (17% of theory) of the desired product.

$^1$H NMR (400 MHz, DMSO-$d_6$, δ/ppm): δ=8.5 (d, 1H), 8.2 (dd, 1H), 7.65-7.50 (m, 3H), 6.65-6.50 (m, 2H), 6.4 (t, 1H), 6.0 (d, 1H), 1.8 (dd, 3H).

LC-MS (Method 5): $R_t$=1.88 min

MS (ESIpos): m/z=257 (M+H)$^+$

Example 38A 1-(4-Amino-2-propylphenyl)pyridin-2(1H)-one

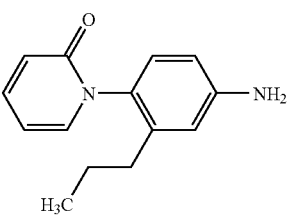

103 mg (0.40 mmol) of example 37A are dissolved in 10 ml of a 1:1 mixture of ethanol and ethyl acetate and hydrogenated flowing through an H-cube (from Thales-Nanotechnologies, Hungary) at standard pressure over palladium on carbon. The resulting solution is concentrated to dryness under reduced pressure. This affords 90 mg (83% of theory) of the desired product.

LC-MS (Method 7): $R_t$=2.77 min

MS (ESIpos): m/z=229 (M+H)$^+$

Example 39A 1-(2-Methyl-4-nitrophenyl)-3-(trifluoromethyl)pyridin-2(1H)-one

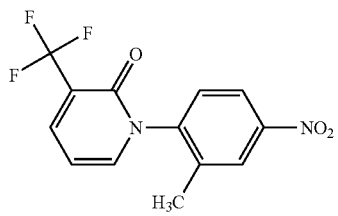

2.5 g (15.3 mmol) of 3-(trifluoromethyl)pyridin-2(1H)-one are dissolved in 40 ml of dimethyl sulfoxide and admixed at room temperature with 2.58 g (22.9 mmol) of potassium tert-butoxide. The suspension is stirred at room temperature for 30 min, before 2.6 g (16.9 mmol) of 1-fluoro-2-methyl-4-nitrobenzene are added and the reaction solution is heated to 80° C. for 20 h. It is diluted cautiously with water. The solution is extracted repeatedly with dichloromethane. The combined organic extracts are washed with water and saturated sodium chloride solution, dried over magnesium sulfate, filtered and concentrated under reduced pressure. The residue is dissolved in acetonitrile and purified by preparative HPLC with a gradient of water and acetonitrile. The product fractions are combined and concentrated to dryness under reduced pressure. This affords 1.87 g (41% of theory) of the desired product.

$^1$H NMR (400 MHz, DMSO-$d_6$, δ/ppm): 8.4 (d, 1H), 8.2 (dd, 1H), 8.15 (d, 1H), 8.0 (dd, 1H), 7.7 (d, 1H), 6.55 (t, 1H), 2.2 (s, 3H).

LC-MS (Method 6): $R_t$=2.26 min
MS (ESIpos): m/z=488 (M+H)$^+$

Example 40A 1-(4-Amino-2-methylphenyl)-3-(trifluoromethyl)pyridin-2(1H)-one

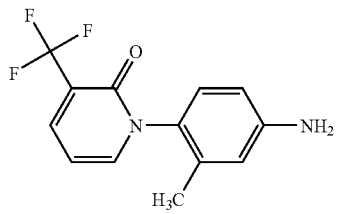

800 mg (2.68 mmol) of example 39A are dissolved in 108 ml of a 1:1 mixture of ethanol and ethyl acetate, and admixed with 1.02 g (16.1 mmol) of ammonium formate and 50 mg of palladium on carbon. The mixture is heated to 80° C. After 45 min, it is allowed to cool and filtered through silica gel. It is washed with ethyl acetate and the filtrate is concentrated to dryness under reduced pressure. This affords 780 mg (100% of theory) of the desired product.

$^1$H NMR (400 MHz, DMSO-$d_6$, δ/ppm): δ=8.05 (d, 1H), 7.8 (d, 1H), 6.9 (d, 1H), 6.5-6.3 (m, 3H), 5.3 (s, 2H), 1.8 (s, 3H).

LC-MS (Method 3): $R_t$=1.42 min
MS (ESIpos): m/z=269 (M+H)$^+$

Example 41A

3-Bromo-1-(2-methyl-4-nitrophenyl)pyridin-2(1H)-one

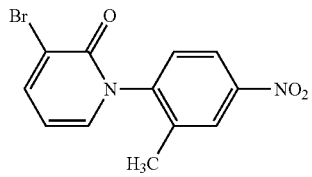

44.5 g (280 mmol) of 3-bromopyridin-2(1H)-one are dissolved in 750 ml of anhydrous dimethyl sulfoxide and admixed at room temperature with 33.4 g (298 mmol) of potassium tert-butoxide in portions. The suspension is stirred at this temperature for 1 h, before 38.5 g (280 mmol) of 1-fluoro-2-methyl-4-nitrobenzene are added and the reaction solution is heated to 80° C. for 20 h. It is allowed to cool and diluted cautiously with water. The precipitated crystalline solid is filtered off, washed with a little water and dried under reduced pressure. This affords 62 g (80% of theory) of the desired product.

$^1$H NMR (400 MHz, DMSO-$d_6$, δ/ppm): δ=8.34 (d, 1H), 8.21 (dd, 1H), 8.10 (dd, 1H), 7.71-7.63 (m, 2H), 6.36 (t, 1H), 2.17 (s, 3H).

LC-MS (Method 3): $R_t$=1.72 min
MS (ESIpos): m/z=309 (M+H)$^+$

Example 42A 1-(2-Methyl-4-nitrophenyl)-3-vinylpyridin-2(1H)-one

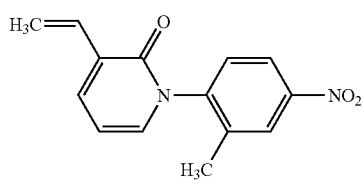

50 g (162 mmol) of the compound from example 41A are dissolved in 700 ml of anhydrous dioxane and admixed with 62 g (194 mmol) of tributylvinyltin and 4.7 g (4.0 mmol) of tetrakis(triphenylphosphine)palladium, and the mixture is heated at reflux for 15 h. It is allowed to cool and filtered through kieselguhr. It is washed with ethyl acetate, and the combined filtrates are concentrated to dryness under reduced pressure. The residue is applied to silica gel and chromatographed on 800 g of silica gel with a gradient of cyclohexane and ethyl acetate. This affords 27 g (62% of theory) of the desired product.

$^1$H NMR (400 MHz, DMSO-$d_6$, δ/ppm): δ=8.35 (d, 1H), 8.2 (dd, 1H), 7.75 (dd, 1H), 7.60 (d, 1H), 7.55 (dd, 1H), 6.75 (dd, 1H), 6.45 (t, 1H), 6.15 (dd, 1H), 5.30 (dd, 1H), 2.17 (s, 3H).

LC-MS (Method 4): R=1.86 min
MS (ESIpos): m/z=257 (M+H)+

Example 43A 3-(2-Hydroxyethyl)-1-(2-methyl-4-nitrophenyl)pyridin-2(1H)-one

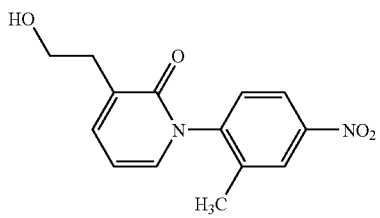

38 g (148 mmol) of the compound from example 42A are admixed while cooling with ice over 45 min with a solution of 40 g (326 mmol) of 9-borabicyclo[3.3.1]nonane in 650 ml of tetrahydrofuran. The mixture is stirred at this temperature for a further hour, before it is admixed with a solution of 30 g (747 mmol) of sodium hydroxide in 740 ml of water within 15 min. 151 ml of a 30% hydrogen peroxide solution are added at such a rate that the temperature does not exceed 30° C. After the addition has ended, the cooling is removed and stirring is continued for a further 30 min. The mixture is extracted repeatedly with ethyl acetate. The combined organic phases are washed with a solution of 780 g (1.63 mol) of sodium disulfite, the organic phase is removed and the aqueous phase is extracted again with ethyl acetate. The combined organic phases are washed with saturated sodium chloride solution, dried over magnesium sulfate and concentrated to dryness under reduced pressure. The residue is applied to silica gel and chromatographed with a gradient of cyclohexane and ethyl acetate. The product-containing fractions are combined and concentrated to dryness under reduced pressure. This affords 38 mg (93% of theory) of the desired product.

$^1$H NMR (400 MHz, DMSO-d$_6$, δ/ppm): δ=8.33 (d, 1H), 8.18 (d, 1H), 7.57 (d, 1H), 7.48-7.40 (m, 2H), 6.33 (t, 1H), 4.58 (t, 1H), 3.62-3.50 (m, 2H), 2.62 (t, 2H), 2.15 (s, 3H).
LC-MS (Method 6): R$_t$=1.57 min
MS (ESIpos): m/z=275 (M+H)+

Example 44A 3-(2-Ethoxyethyl)-1-(2-methyl-4-nitrophenyl)pyridin-2(1H)-one

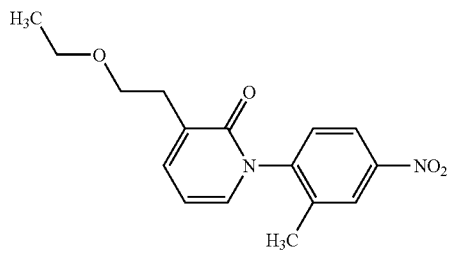

135 mg (0.49 mmol) of example 43A are dissolved in 1 ml of anhydrous N,N-dimethylformamide and admixed with 24 mg (0.59 mmol) of sodium hydride. The mixture is left to stir for a further 30 min, before 153 mg (1 mmol) of iodoethane are added. After 3 h, another 48 mg (1.21 mmol) of sodium hydride and 307 mg (1.97 mmol) of iodoethane are added, before stirring is continued for a further 30 min. The mixture is admixed with water and filtered, and the filtrate is purified by preparative HPLC with a gradient of water and acetonitrile. The product fractions are combined and concentrated to dryness under reduced pressure. This affords 92 mg (62% of theory) of the desired product.

$^1$H NMR (400 MHz, DMSO-d$_6$, δ/ppm): δ=8.35 (d, 1H), 8.2 (dd, 1H), 7.6 (d, 1H), 7.45 (m, 2H), 6.35 (t, 1H), 3.6 (t, 2H), 3.4 (q, 2H), 2.7 (t, 2H), 2.15 (s, 3H), 1.1 (t, 3H).
LC-MS (Method 5): R$_t$=2.00 min
MS (ESIpos): m/z=303 (M+H)+

Example 45A 1-(4-Amino-2-methylphenyl)-3-(2-ethoxyethyl)pyridin-2(1H)-one

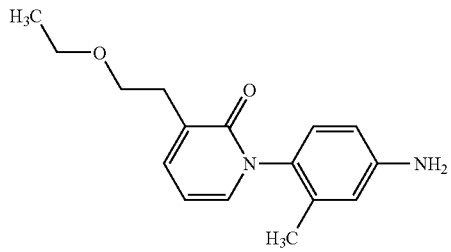

90 mg (0.30 mmol) of example 44A are dissolved in 12 ml of a 1:1 mixture of ethanol and ethyl acetate, and admixed with 113 mg (1.79 mmol) of ammonium formate and 50 mg of palladium on carbon. The mixture is heated to 80° C. It is allowed to cool for 1 h and filtered through silica gel. It is washed with ethyl acetate, and the filtrate is concentrated to dryness under reduced pressure. This affords 80 mg (99% of theory) of the desired product.

$^1$H NMR (400 MHz, DMSO-d$_6$, δ/ppm): δ=7.4 (d, 1H), 7.3 (dd, 1H), 6.8 (d, 1H), 6.5-6.4 (m, 2H), 6.2 (t, 1H), 5.2 (s, 2H), 3.55 (t, 2H), 3.45 (q, 2H), 2.65 (t, 2H), 1.8 (s, 3H), 1.1 (t, 3H).
LC-MS (Method 3): R$_t$=1.30 min
MS (ESIpos): m/z=273 (M+H)+

Example 46A 3-(2-Methoxyethyl)-1-(2-methyl-4-nitrophenyl)pyridin-2(1H)-one

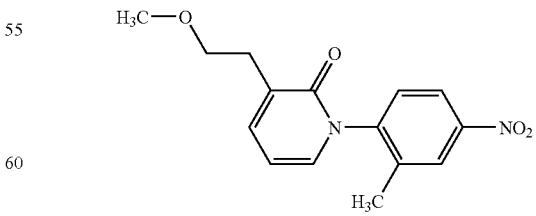

135 mg (0.49 mmol) of example 43A are dissolved in 1 ml of anhydrous N,N-dimethylformamide and admixed with 24 mg (0.59 mmol) of sodium hydride. The mixture is left to stir for a further 30 min, before 139 mg (1 mmol) of iodomethane are added. After 3 h, another 48 mg (1.21 mmol) of sodium hydride and 278 mg (1.97 mmol) of iodomethane are added, before stirring is continued for a further 30 min. Then the mixture is admixed with water and filtered, and the filtrate is purified by preparative HPLC with a gradient of water and acetonitrile. The product fractions are combined and concentrated to dryness under reduced pressure. This affords 94 mg (66% of theory) of the desired product.

$^1$H NMR (400 MHz, DMSO-d$_6$, δ/ppm): δ=8.3 (d, 1H), 8.15 (dd, 1H), 7.6 (d, 1H), 7.45 (d, 2H), 6.35 (t, 1H), 3.55 (t, 2H), 3.3 (s, 3H), 2.7 (t, 2H), 2.15 (s, 3H).

LC-MS (Method 5): R$_t$=1.82 min
MS (ESIpos): m/z=289 (M+H)$^+$

Example 47A 1-(4-Amino-2-methylphenyl)-3-(2-methoxyethyl)pyridin-2(1H)-one

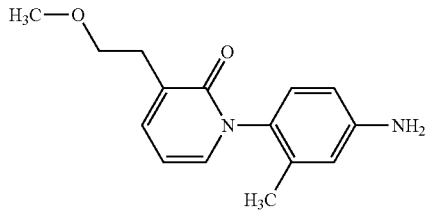

93 mg (0.32 mmol) of example 46A are dissolved in 13 ml of a 1:1 mixture of ethanol and ethyl acetate, and admixed with 122 mg (1.94 mmol) of ammonium formate and 50 mg of palladium on carbon. The mixture is heated to 80° C. It is allowed to cool for 1 h and filtered through silica gel. It is washed with ethyl acetate, and the filtrate is concentrated to dryness under reduced pressure. This affords 83 mg (93% of theory) of the desired product.

$^1$H NMR (400 MHz, DMSO-d$_6$, δ/ppm): δ=7.35 (d, 1H), 7.3 (dd, 1H), 6.8 (d, 1H), 6.5-6.4 (m, 2H), 6.2 (t, 1H), 5.2 (s, 2H), 3.55 (t, 2H), 3.35 (s, 3H), 2.65 (t, 2H), 1.8 (s, 3H).

LC-MS (Method 3): R$_t$=1.12 min
MS (ESIpos): m/z=259 (M+H)$^+$

Example 48A 1-(2-Fluoropyridin-3-yl)propan-1-ol

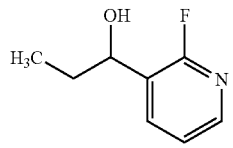

A freshly prepared LDA solution (68.0 mmol) in 500 ml of THF is cooled to −75° C., and 6.00 g (61.8 mmol) of 2-fluoropyridine are added. The mixture is left to stir at this temperature for 2 h, in the course of which a suspension forms. Thereafter, 4.31 g (74.2 mmol) of propanal are added, in the course of which the internal temperature rises to −45° C. After 2 h, the mixture is allowed to come to RT, poured onto saturated ammonium chloride solution and extracted three times with tert-butyl methyl ether. The combined organic phases are washed with sodium chloride solution, dried over sodium sulfate and concentrated. They are purified by chromatography on silica gel (eluent: dichloromethane, then dichloromethane/methanol=25:1). This affords 8.00 g (76% of theory) of the title compound.

$^1$H NMR (400 MHz, DMSO-d$_6$, δ/ppm): 8.13-8.09 (m, 1H), 7.99 (ddd, 1H), 7.36 (ddd, 1H), 5.42 (d, 1H), 4.68 (dq, 1H), 1.72-1.56 (m, 2H), 0.85 (t, 3H).

HPLC (Method 4): R$_t$=1.50 min.
MS (ESIpos, m/z): 156 (M+H)$^+$.

Example 49A 1-(2-Fluoropyridin-3-yl)propyl Acetate

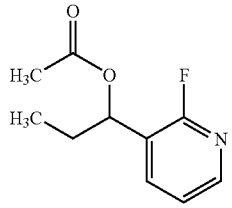

2.75 g (17.7 mmol) of the product from example 48A are dissolved in 12 ml of glacial acetic acid and admixed with 4 ml of concentrated sulfuric acid. The mixture is heated to 130° C. for 30 min and, after cooling, stirred into ice-water. A pH of 8 is established with sodium hydroxide solution, and then extraction is effected with dichloromethane. The combined organic phases are dried over sodium sulfate and concentrated cautiously. This affords 3.30 g (94% of theory) of the title compound, which is converted further without purification.

$^1$H NMR (400 MHz, DMSO-d$_6$, δ/ppm): 8.21-8.18 (m, 1H), 7.97 (ddd, 1H), 7.39 (ddd, 1H), 5.71 (t, 1H), 2.07 (s, 3H), 1.90-1.77 (m, 2H), 0.85 (t, 3H).

HPLC (Method 4): R$_t$=2.16 min.
MS (ESIpos, m/z): 198 (M+H)$^+$.

Example 50A

3-Propyl-2-fluoropyridine

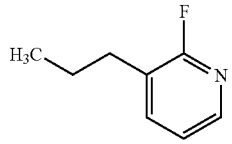

3.50 g (17.7 mmol) of the product from example 49A are dissolved in 30 ml of ethanol and admixed with 2.00 g of 10% palladium on activated carbon. Hydrogenation is effected overnight in a hydrogen atmosphere under standard pressure. The mixture is filtered with suction, washed with ethanol and concentrated cautiously under reduced pressure. This affords 1.9 g of approx. 89% pure product (69% of theory), which is converted further without purification.

$^1$H NMR (400 MHz, DMSO-d$_6$, δ/ppm): 8.08-8.05 (m, 1H), 7.84 (ddd, 1H), 7.28 (ddd, 1H), 2.58 (t, 2H), 1.63-1.54 (m, 2H), 0.90 (t, 3H).

HPLC (Method 6): R$_t$=3.54 min
MS (ESIpos, m/z): 140 (M+H)$^+$..

Example 51A

3-Propylpyridin-2(1H)-one

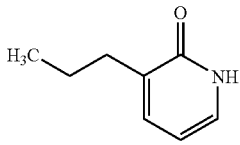

The title compound is synthesized analogously to example 55A from 1.90 g (13.7 mmol) of the product from example 50A. This affords 1.50 g (80% of theory) of the desired compound.

$^1$H NMR (400 MHz, DMSO-d$_6$, δ/ppm): 11.42 (s, broad, 1H), 7.23 (dd, 1H), 7.19 (dd, 1H), 6.09 (t, 1H), 2.33 (t, 2H), 1.55-1.44 (m, 2H), 0.87 (t, 3H).

HPLC (Method 6): R$_t$=2.72 min.
MS (ESIpos, m/z): 138 (M+H)$^+$.

Example 52A 1-(2-Methoxy-4-nitrophenyl)-3-propylpyridin-2(1H)-one

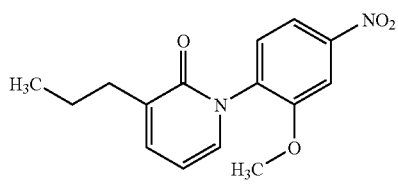

500 mg (3.65 mmol) of the product from example 51A are dissolved in 7.3 ml of DMF and cooled to 0° C. To this are added 613 mg (5.47 mmol) of potassium tert-butoxide, and the mixture is left to stir at RT for 30 min. Then 624 mg (3.65 mmol) of 1-fluoro-2-methoxy-4-nitrobenzene are added. The mixture is stirred at RT for 6 h, water is added and the mixture is extracted four times with ethyl acetate. The combined organic phases are dried over sodium sulfate and concentrated. Purification is effected by preparative HPLC. The resulting product fraction is purified further by chromatography on silica gel (eluent: dichloromethane, then 10:1 dichloromethane/methanol). This affords 158 mg (15% of theory) of the desired compound as a solid.

$^1$H NMR (400 MHz, DMSO-d$_6$, δ/ppm): 7.97 (d, 1H), 7.93 (dd, 1H), 7.61 (d, 1H), 7.40-7.33 (m, 2H), 6.26 (t, 1H), 3.89 (s, 3H), 2.43-2.36 (m, 2H), 1.60-1.48 (m, 2H), 0.91 (t, 3H).

HPLC (Method 5): R$_t$=2.19 min.
MS (ESIpos, m/z): 289 (M+H)$^+$.

Example 53A 1-(4-Amino-2-methoxyphenyl)-3-propylpyridin-2(1H)-one

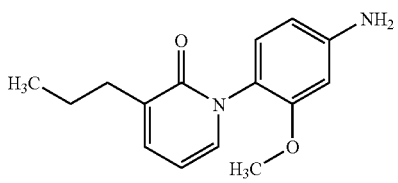

130 mg (0.45 mmol) of the product from example 52A are initially charged in 4 ml of THF. To this are added 50 mg of 10% palladium on activated carbon, and hydrogenation is effected at standard pressure in a hydrogen atmosphere for 1 h. The reaction solution is then filtered through Celite which is rinsed with ethyl acetate. The mixture is concentrated under reduced pressure to obtain 115 mg (99% of theory) of the crystalline title compound.

$^1$H NMR (400 MHz, DMSO-d$_6$, δ/ppm): 7.25-7.19 (m, 2H), 6.80 (d, 1H), 6.32 (d, 1H), 6.17 (dd, 1H), 6.11 (t, 1H), 5.75 (s, broad, 2H), 3.62 (s, 3H), 2.40-2.32 (m, 2H), 1.56-1.46 (m, 2H), 0.90 (t, 3H).

HPLC (Method 3): R$_t$=1.56 min.
MS (ESIpos, m/z): 259 (M+H)$^+$.

Example 54A

2-Fluoro-3-(2-methoxy-4-nitrophenyl)pyridine

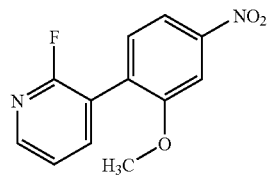

2.00 g (7.17 mmol) of 2-iodo-5-nitroanisole, 2.02 g (14.3 mmol) of (2-fluoropyridin-3-yl)boronic acid (A. Bouillon, J.-C. Lancelot, V. Collot, P. R. Bovy, S. Rault, *Tetrahedron* 2002, 58, 3323-3328.), 1.81 g (21.5 mmol) of sodium hydrogen carbonate and 117 mg (0.14 mmol) of [1,1'-bis(diphenylphosphino)ferrocene]palladium dichloride are heated to 100° C. in a degassed mixture of 40 ml of dioxane and 10 ml of water for 1 h. After cooling, the mixture is diluted with water and extracted three times with ethyl acetate. The combined organic phases are dried over sodium sulfate, clarified over activated carbon and concentrated. Purification is effected by chromatography on silica gel (eluent: dichloromethane) to obtain 1.55 g (87% of theory) of the desired product.

$^1$H NMR (400 MHz, DMSO-d$_6$, δ/ppm): 3.32 (d, 1H), 8.02 (ddd, 1H), 7.95 (dd, 1H), 7.92 (d, 1H), 7.64 (d, 1H), 7.49 (ddd, 1H), 4.10 (s, 3H).

HPLC (Method 6): R$_t$=3.61 min.
MS (ESIpos, m/z): 249 (M+H)$^+$.

Example 55A 3-(2-Methoxy-4-nitrophenyl)pyridin-2(1H)-one

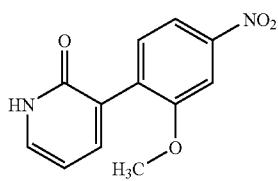

1.50 g (6.04 mmol) of the product from example 54A are heated overnight in a mixture of 75 ml of dioxane and 75 ml of 4-molar hydrochloric acid. The mixture is then alkalized with sodium carbonate solution. The precipitate is filtered off with suction, washed with water and dried. This affords 1.43 g (96% of theory) of the desired compound.

$^1$H NMR (400 MHz, DMSO-d$_6$, δ/ppm): 11.82 (s, broad, 1H), 7.85 (dd, 1H), 7.82 (d, 1H), 7.57 (d, 1H), 7.52 (dd, 1H), 7.44 (dd, 1H), 6.28 (t, 1H), 3.86 (s, 3H).

HPLC (Method 3): R$_t$=1.40 min.

MS (ESIpos, m/z): 247 (M+H)$^+$.

Example 56A

1-Ethyl-3-(2-methoxy-4-nitrophenyl)pyridin-2(1H)-one

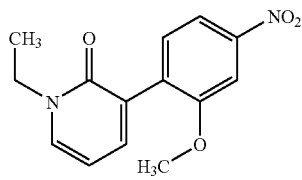

350 mg (1.42 mmol) of the product from example 55A are suspended in 3.5 ml of DMF. To this are added 393 mg (2.84 mmol) of potassium carbonate and 266 mg (1.71 mmol) of iodoethane, and the mixture is left to stir at RT for 3 h. Then it is admixed with water and extracted with dichloromethane. The organic solution is dried over sodium sulfate, concentrated and purified by preparative HPLC. This affords 224 mg (57% of theory) of the title compound.

$^1$H NMR (400 MHz, DMSO-d$_6$, δ/ppm): 7.87-7.81 (m, 2H), 7.78 (d, 1H), 7.56 (d, 1H), 7.48 (dd, 1H), 6.33 (t, 1H), 3.96 (q, 2H), 3.86 (s, 3H), 1.25 (t, 3H).

HPLC (Method 5): R$_t$=1.88 min.

MS (ESIpos, m/z): 275 (M+H)$^+$.

Example 57A 3-(4-Amino-2-methoxyphenyl)-1-ethylpyridin-2(1H)-one BAY 821292, SIRO3378

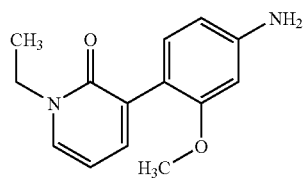

196 mg (0.72 mmol) of the product from example 56A are hydrogenated analogously to example 53A. This affords 184 mg (98% of theory) of the title compound.

$^1$H NMR (400 MHz, DMSO-d$_6$, δ/ppm): 7.57 (dd, 1H), 7.24 (dd, 1H), 6.91 (d, 1H), 6.25 (d, 1H), 6.19 (t, 1H), 6.14 (dd, 1H), 5.14 (s, 2H), 3.91 (q, 2H), 3.61 (s, 3H), 1.21 (t, 3H).

HPLC (Method 3): R$_t$=0.92 min.

MS (ESIpos, m/z): 244 (M+H)$^+$.

Example 58A 3-(2-Methoxy-4-nitrophenyl)-1-methylpyridin-2(1H)-one

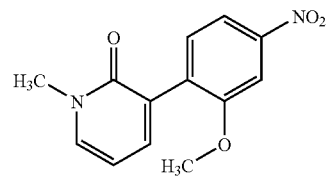

350 mg (1.42 mmol) of the product from example 55A are alkylated analogously to example 56A with 242 mg (1.71 mmol) of methyl iodide. This affords 347 mg (88% of theory) of the title compound.

$^1$H NMR (400 MHz, DMSO-d$_6$, δ/ppm): 7.85 (d, 1H), 7.82 (d, 1H), 7.78 (dd, 1H), 7.54 (d, 1H), 7.48 (dd, 1H), 6.31 (t, 1H), 3.85 (s, 3H), 3.48 (s, 3H).

HPLC (Method 4): R$_t$=1.77 min.

MS (ESIpos, m/z): 261 (M+H)$^+$.

Example 59A 3-(4-Amino-2-methoxyphenyl)-1-methylpyridin-2(1H)-one

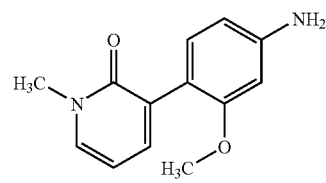

320 mg (1.23 mmol) of the product from example 58A are hydrogenated analogously to example 53A. This affords 320 mg (85% purity, 96% of theory) of the title compound.

$^1$H NMR (400 MHz, DMSO-d$_6$, δ/ppm): 7.57 (dd, 1H), 7.25 (dd, 1H), 6.89 (d, 1H), 6.25 (d, 1H), 6.18 (t, 1H), 6.14 (dd, 1H), 5.14 (s, 2H), 3.61 (s, 3H), 3.43 (s, 3H).

HPLC (Method 3): R$_t$=0.62 min.

MS (ESIpos, m/z): 231 (M+H)$^+$.

Example 60A

1-Methyl-3-(2-methyl-4-nitrophenyl)tetrahydropyrimidin-2(1H)-one

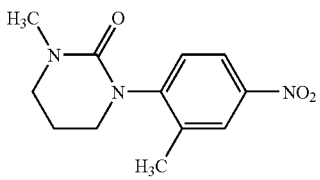

16.1 g (76.1 mmol) of potassium phosphate and 0.362 g (1.90 mmol) of copper(I) iodide are initially charged, and the apparatus is baked out and then flushed with argon. 10.0 g (38.1 mmol) of 1-iodo-2-methyl-4-nitrobenzene, 6.51 g (57.0 mmol) of 1-methyltetrahydropyrimidin-2(1H)-one and 0.394 g (3.80 mmol) of N,N'-dimethylenediamine in 200 ml of dioxane are added, and the mixture is stirred at 110° C. After 19 h, after cooling, the mixture is filtered with suction through kieselguhr and then washed three times with 100 ml of ethyl acetate. The solvent is removed under reduced pressure and the residue is purified by chromatography on silica gel (2:1→1:1 cyclohexane/ethyl acetate). This affords 5.94 g (63% of theory) of the desired compound.

$^1$H NMR (400 MHz, DMSO-d$_6$, δ/ppm): 8.12 (d, 1H), 8.04 (dd, 1H), 7.43 (d, 1H), 3.78-3.61 (m, 1H), 3.46-3.34 (m, 3H), 2.86 (s, 3H), 2.25 (s, 3H), 2.10-2.01 (m, 2H).

HPLC (Method 1): R$_t$=3.73 min.

MS (DCI, m/z): 250 (M+H)$^+$.

Example 61A 1-(4-Amino-2-methylphenyl)-3-methyltetrahydropyrimidin-2(1H)-one

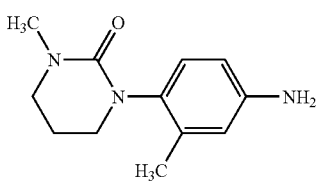

60 mg (0.24 mmol) of example 60A are dissolved in 10 ml of ethanol and admixed with 100 mg of palladium on carbon. Hydrogenation is effected at RT in a hydrogen atmosphere under standard pressure for 18 h. Subsequently, the mixture is filtered through kieselguhr and washed with ethanol, and the filtrate is freed of the solvent. The product (51 mg) is converted further without further purification.

$^1$H NMR (400 MHz, DMSO-d$_6$, δ/ppm): 6.71 (d, 1H), 6.39-6.27 (m, 2H), 4.88 (br.s, 2H), 3.48-3.37 (m, 1H), 3.35-3.19 (m, 3H), 2.80 (s, 3H), 2.03-1.92 (m, 5H).

HPLC (Method 1): R$_t$=3.29 min.

MS (ESIpos, m/z): 220 (M+H)$^+$.

Example 62A 1-(2-Methoxy-4-nitrophenyl)-3-methyltetrahydropyrimidin-2(1H)-one

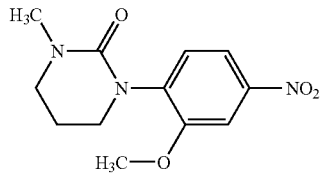

450 mg (3.94 mmol) of 1-methyltetrahydropyrimidin-2(1H)-one in 15 ml of DMF are admixed at 0° C. with 663 mg (5.91 mmol) of potassium tert-butoxide, and the mixture is stirred at room temperature for 30 min. 742 mg (4.33 mmol) of 1-fluoro-2-methoxy-4-nitrobenzene are added and the mixture is stirred at RT. After 2 h, the mixture is admixed with 150 ml of water and 8 ml of saturated aqueous sodium chloride solution, and extracted three times with 30 ml each time of ethyl acetate. The combined organic phases are washed with 30 ml of water and then dried over sodium sulfate. After filtration, the solvents are removed under reduced pressure. The residue is purified by chromatography on silica gel (1:5→1:10 cyclohexane/ethyl acetate). This affords 457 mg (43% of theory) of the desired compound.

$^1$H NMR (400 MHz, DMSO-d$_6$, δ/ppm): 7.85 (m, 2H), 7.44-7.39 (m, 1H), 3.90 (s, 3H), 3.48 (t, 2H), 3.38-3.31 (m, 2H), 2.84 (s, 3H), 2.05-1.93 (m, 2H).

HPLC (Method 1): R$_t$=3.57 min.

MS (DCI, m/z): 266 (M+H)$^+$.

Example 63A 1-(4-Amino-2-methoxyphenyl)-3-methyltetrahydropyrimidin-2(1H)-one

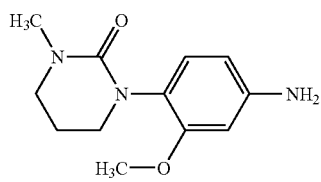

430 mg (1.62 mmol) of example 62A are dissolved in 50 ml of THF and admixed with 100 mg of palladium on carbon. Hydrogenation is effected at RT in a hydrogen atmosphere under standard pressure for 18 h. Subsequently, the mixture is filtered and washed with THF, and the filtrate is freed of the solvent. The reaction product (401 mg) is converted further without further purification.

¹H NMR (400 MHz, DMSO-d₆, δ/ppm): 6.69 (d, 1H), 6.22 (d, 1H), 6.06 (dd, 1H), 5.00 (br.s, 2H), 3.65 (s, 3H), 3.37-3.25 (m, 4H), 2.79 (s, 3H), 2.00-1.91 s (m, 2H).

HPLC (Method 1): $R_t$=2.88 min.

MS (ESIpos, m/z): 236 (M+H)⁺.

Example 64A 1-(2-{[tert-Butyl(diphenyl)silyl]oxy}ethyl)tetrahydropyrimidin-2(1H)-one

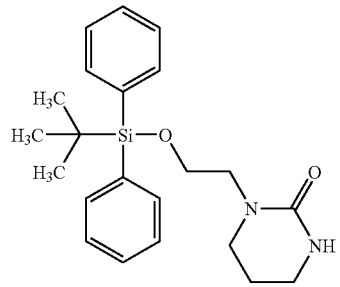

34.3 g (237 mmol) of 1-(2-hydroxyethyl)tetrahydropyrimidin-2(1H)-one (patent; Chem. Werke Huels; DE 1121617; 1962; Chem. Abstr.; EN; 56; 11601 g; 1962) are dissolved in 612 ml of DMF and admixed with 36.1 g (356 mmol) of triethylamine, 1.45 g (11.9 mmol) of DMAP and 85.0 g (309 mmol) of tert-butyl(chloro)diphenylsilane, and stirred at RT for 18 h. Then the mixture is added to 2000 ml of water and extracted three times with dichloromethane. The combined organic phases are washed twice with water and then dried over sodium sulfate. After filtration, the solvents are removed under reduced pressure. The residue is recrystallized from acetonitrile. This affords 71.9 g (78% of theory) of the desired compound.

¹H NMR (400 MHz, DMSO-d₆, δ/ppm): 7.67-7.58 (m, 4H), 7.48-7.39 (m, 6H), 6.17 (br.s, 1H), 3.70 (t, 2H), 3.40-3.26 (m, 4H), 3.17-3.05 (m, 2H), 1.80-1.72 (m, 2H), 0.99 (s, 9H).

HPLC (Method 1): $R_t$=4.86 min.

MS (ESIpos, m/z): 383 (M+H)⁺.

Example 65A 1-(2-{[tert-Butyl(diphenyl)silyl]oxy}ethyl)-3-(2-methyl-4-nitrophenyl)tetrahydropyrimidin-2(1H)-one

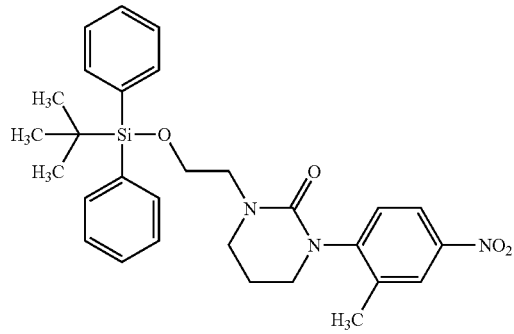

750 mg (1.96 mmol) of example 64A in 9 ml of DMF are admixed at 0° C. with 330 mg (2.94 mmol) of potassium tert-butoxide, and the mixture is stirred at room temperature for 30 min. 335 mg (2.16 mmol) of 1-fluoro-2-methyl-4-nitrobenzene are added and the mixture is stirred at 60° C. After 5 h, the reaction solution is cooled and added to a solution of 100 ml of water with 10 ml of saturated aqueous ammonium chloride solution. Then the mixture is extracted three times with 70 ml each time of ethyl acetate. The combined organic phases are washed with 100 ml of water and then dried over sodium sulfate. After filtration, the solvents are removed under reduced pressure. The residue is purified by chromatography on silica gel (3:1 cyclohexane/ethyl acetate). This affords 135 mg (13% of theory) of the desired compound.

HPLC (Method 1): $R_t$=5.17 min.

MS (DCI, m/z): 518 (M+H)⁺.

Example 66A 1-(4-Amino-2-methylphenyl)-3-(2-{[tert-butyl(diphenyl)silyl]oxy}ethyl)tetrahydropyrimidin-2(1H)-one

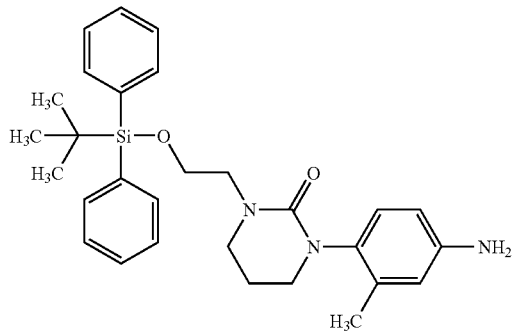

229 mg (0.44 mmol) of example 65A are dissolved in 10 ml of THF and admixed with 50 mg of palladium on carbon. Hydrogenation is effected at RT in a hydrogen atmosphere under standard pressure for 4 h. Subsequently, the mixture is filtered and washed with THF, and the filtrate is freed of the solvent. The reaction product (230 mg, purity 67%) is converted further without further purification.

HPLC (Method 2): $R_t$=4.61 min.

MS (DCI, m/z): 488 (M+H)⁺.

Example 67A

N-{[(5S)-3-{4-[3-(2-{[tert-Butyl(diphenyl)silyl]oxy}ethyl)-2-oxotetrahydropyrimidin-1(2H)-yl]-3-methylphenyl}-2-oxo-1,3-oxazolidin-5-yl]methyl}-5-chlorothiophene-2-carboxamide

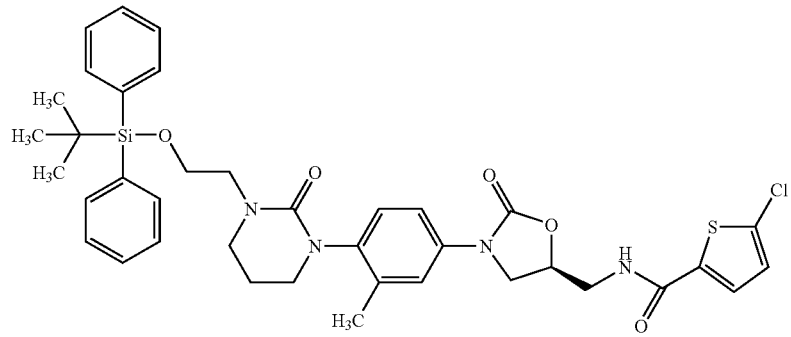

A solution of 215 mg (0.42 mmol) of the product from example 66A in 6 ml of acetonitrile is admixed with 105 mg (0.486 mmol) of the product from example 1A. To the suspension are added 148 mg (0.663 mmol) of magnesium perchlorate, after which the mixture is left to stir at RT for 18 h. Then 179 mg (1.11 mmol) of 1,1'-carbonyldiimidazole and 5 mg (0.04 mmol) of DMAP are added, and the mixture is stirred at 60° C. After 3 h, the mixture is cooled and then added to 50 ml of water. After adding 50 ml of ethyl acetate, the phases are separated and the aqueous phase is extracted three times with ethyl acetate. The combined organic phases are dried over sodium sulfate. The solvents are removed under reduced pressure and the residue is purified by chromatography on silica gel (20:1 dichloromethane/methanol). This affords 241 mg (74% of theory) of the desired compound.

HPLC (Method 2): $R_t$=5.16 min.
MS (ESIpos, m/z): 731 (M+H)$^+$.

Example 68A 1-(2-{[tert-Butyl(diphenyl)silyl]oxy}ethyl)-3-(2-chloro-4-nitrophenyl)tetrahydropyrimidin-2(1H)-one

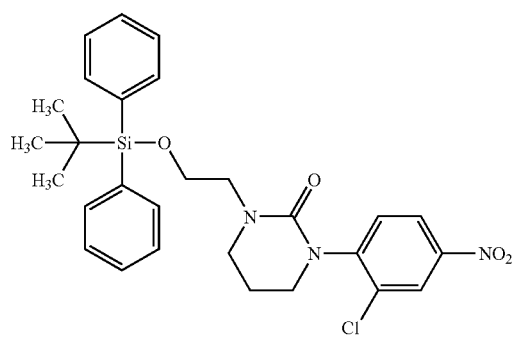

500 mg (1.31 mmol) of example 64A in 6 ml of DMF are admixed at 0° C. with 220 mg (1.96 mmol) of potassium tert-butoxide, and the mixture is stirred at room temperature for 30 min. 252 mg (1.44 mmol) of 2-chloro-1-fluoro-4-nitrobenzene are added, and the mixture is stirred at RT. After 22 h, the reaction solution is cooled and added to a solution of 50 ml of water and 8 ml of saturated aqueous sodium chloride solution. Then the mixture is extracted three times with 30 ml of ethyl acetate each time. The combined organic phases are washed with 30 ml of water and then dried over sodium sulfate. After filtration, the solvents are removed under reduced pressure. The residue is purified by chromatography on silica gel (2:1 cyclohexane/ethyl acetate). This affords 200 mg (28% of theory) of the desired compound.

$^1$H NMR (400 MHz, DMSO-$d_6$, δ/ppm): 8.34 (d, 1H), 8.21 (dd, 1H), 7.68-7.62 (m, 5H), 7.51-7.42 (m, 6H), 3.76 (t, 2H), 3.58-3.41 (m, 6H), 2.07 (tt, 2H), 1.01 (s, 9H).
HPLC (Method 2): $R_t$=5.78 min.
MS (DCI, m/z): 538 (M+H)$^+$.

Example 69A 1-(4-Amino-2-chlorophenyl)-3-(2-{[tert-butyl(diphenyl)silyl]oxy}ethyl)tetrahydropyrimidin-2(1H)-one

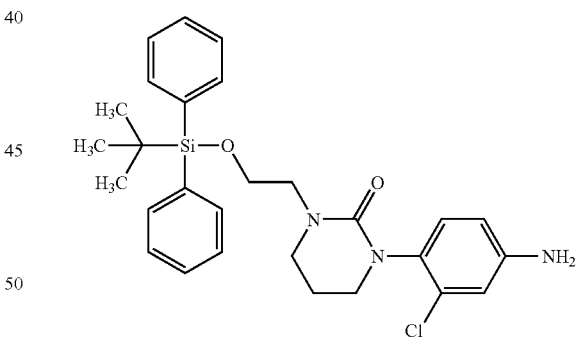

386 mg (0.72 mmol) of example 68A are dissolved in 10 ml of THF and admixed with 50 mg of palladium on carbon. Hydrogenation is effected at RT in a hydrogen atmosphere under standard pressure for 2 h. Subsequently, the mixture is filtered and washed three times with THF, and the filtrate is freed from the solvent. The reaction product (365 mg, 80% purity) is converted further without further purification.

$^1$H NMR (400 MHz, DMSO-$d_6$, δ/ppm): 7.66-7.60 (m, 4H), 7.51-7.40 (m, 6H), 6.88 (d, 1H), 6.62 (d, 1H), 6.45 (dd, 1H), 5.33 (br.s., 2H), 3.77-3.68 (m, 2H), 3.50-3.30 (m, 6H), 2.05-1.94 (m, 2H), 1.01 (s, 9H).
HPLC (Method 2): $R_t$=4.71 min.
MS (ESIpos, m/z): 508 (M+H)$^+$.

Example 70A

N-{[(5S)-3-{4-[3-(2-{[tert-Butyl (diphenyl)silyl]oxy}ethyl)-2-oxotetrahydropyrimidin-1(2H)-yl]-3-chlorophenyl}-2-oxo-1,3-oxazolidin-5-yl]methyl}-5-chlorothiophene-2-carboxamide

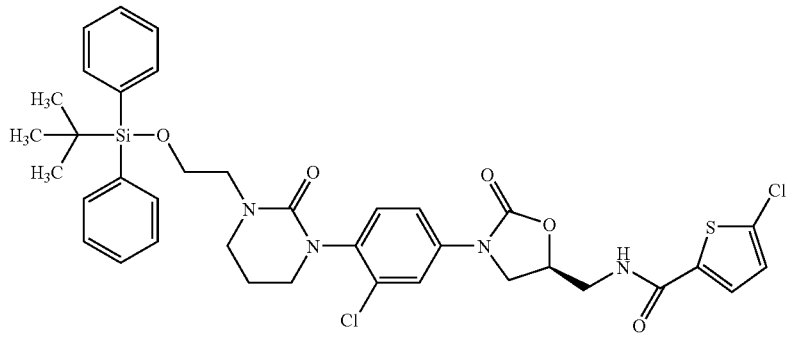

A solution of 364 mg (0.718 mmol) of the product from example 69A in 8 ml of acetonitrile is admixed with 172 mg (0.789 mmol) of the product from example 1A. To the suspension are added 240 mg (1.07 mmol) of magnesium perchlorate, after which the mixture is left to stir at RT for 15 h. Then 291 mg (1.79 mmol) 1,1'-carbonyldiimidazole and 9 mg (0.08 mmol) of DMAP are added, and the mixture is stirred at 60° C. After 3 h, the mixture is cooled and then diluted with 70 ml of water and 50 ml of ethyl acetate. The phases are separated and the aqueous phase is extracted twice with ethyl acetate. The combined organic phases are dried over sodium sulfate. The solvents are removed under reduced pressure and the residue is purified by chromatography on silica gel (20:1 dichloromethane/methanol). This affords 366 mg (59% of theory) of the desired compound.

$^1$H NMR (400 MHz, DMSO-$d_6$, δ/ppm): 8.96 (dd, 1H), 7.70 (d, 1H), 7.66-7.58 (m, 5H), 7.48-7.36 (m, 7H), 7.31 (d, 1H), 7.21-7.16 (m, 1H), 4.89-4.78 (m., 1H), 4.19 (dd, 1H), 3.89-3.82 (m, 1H), 3.80-3.68 (m, 2H), 3.60 (t, 2H), 3.52-3.38 (m, 6H), 2.10-1.95 (m, 2H), 1.01 (s, 9H).

HPLC (Method 2): $R_t$=5.26 min.
MS (ESIpos, m/z): 751 (M+H)$^+$.

Example 71A 1-(2-{[tert-Butyl(diphenyl)silyl]oxy}ethyl)-3-[4-nitro-2-(trifluoromethyl)phenyl]tetrahydro-pyrimidin-2(1H)-one

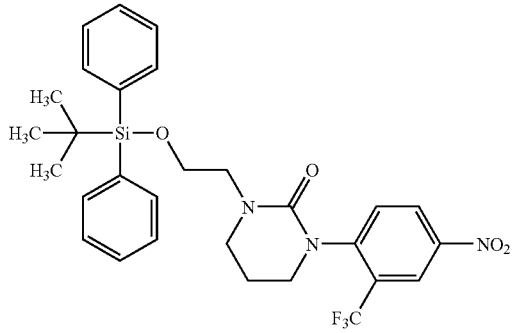

71.8 g (187 mmol) of example 64A in 1300 ml of DMF are admixed at 0° C. with 31.6 g (281 mmol) of potassium tert-butoxide, and the mixture is stirred at room temperature for 30 min. 43.2 g (206 mmol) of 1-fluoro-4-nitro-2-(trifluoromethyl)benzene in 100 ml of DMF are added and the mixture is stirred at RT. After 18 h, the reaction solution is admixed with 2000 ml of water and 50 ml of saturated aqueous sodium chloride solution. After phase separation, the aqueous phase is extracted three times with 500 ml each time of ethyl acetate. The combined organic phases are washed twice with 500 ml of water and then dried over sodium sulfate. After filtration, the solvents are removed under reduced pressure. The residue is purified by chromatography on silica gel (5:1→2:1 cyclohexane/ethyl acetate). This affords 31.3 g (28% of theory) of the desired compound.

$^1$H NMR (400 MHz, DMSO-$d_6$, δ/ppm): 8.56 (dd, 1H), 8.45 (d, 1H), 7.74 (d, 1H), 7.68-7.60 (m, 4H), 7.51-7.39 (m, 6H), 3.80-3.62 (m, 3H), 3.58-3.44 (m, 3H), 3.42-3.31 (m, 2H), 2.05 (tt, 2H), 1.01 (s, 9H).

HPLC (Method 2): $R_t$=5.50 min.
MS (ESIpos, m/z): 572 (M+H)$^+$.

Example 72A

1-[4-Amino-2-(trifluoromethyl)phenyl]-3-(2-{[tert-butyl(diphenyl)silyl]oxy}ethyl)tetrahydro-pyrimidin-2(1H)-one

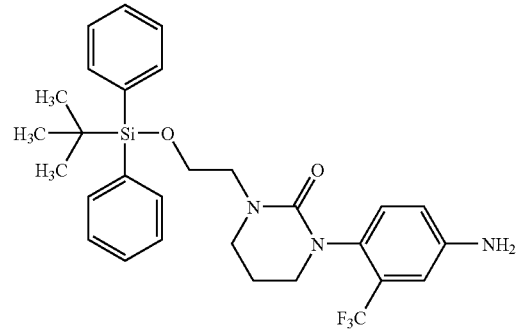

21.2 g (37.1 mmol) of example 71A are dissolved in 700 ml of THF and admixed with 200 mg of palladium on carbon.

Hydrogenation is effected at RT in a hydrogen atmosphere under standard pressure for 2 h. Subsequently, the mixture is filtered and washed three times with THF, and the filtrate is freed of the solvent. The reaction product (20.5 g) is converted further without further purification.

$^1$H NMR (400 MHz, DMSO-$d_6$, δ/ppm): 7.68-7.61 (m, 4H), 7.51-7.40 (m, 6H), 6.94 (d, 1H), 6.84 (d, 1H), 6.75 (dd, 1H), 5.53 (br.s., 2H), 3.77-3.65 (m, 2H), 3.50-3.23 (m, 6H), 2.05-1.92 (m, 2H), 1.01 (s, 9H).

HPLC (Method 2): $R_t$=5.41 min.
MS (ESIpos, m/z): 542 (M+H)$^+$.

Example 73A

N-{[(5S)-3-{4-[3-(2-{[tert-Butyl(diphenyl)silyl]oxy}ethyl)-2-oxotetrahydropyrimidin-1(2H)-yl]-3-(trifluoromethyl)phenyl}-2-oxo-1,3-oxazolidin-5-yl]methyl}-5-chlorothiophene-2-carboxamide

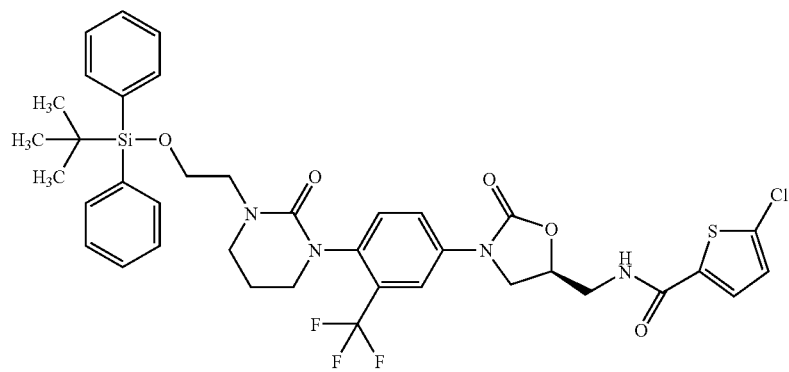

A solution of 20.5 g (37.8 mmol) of the product from example 72A in 300 ml of acetonitrile is admixed with 9.06 g (41.6 mmol) of the product from example 1A. To the suspension are added 12.7 g (56.7 mmol) of magnesium perchlorate, after which the mixture is left to stir at RT for 15 h. Then 15.3 g (94.6 mmol) of 1,1'-carbonyldiimidazole and 462 mg (3.78 mmol) of DMAP are added, and the mixture is stirred at RT. After 15 h, the mixture is added to 1500 ml of water, the phases are separated and the aqueous phase is extracted three times with ethyl acetate. The combined organic phases are dried over sodium sulfate. The solvents are removed under reduced pressure and the residue is purified by chromatography on silica gel (1:5 cyclohexane/ethyl acetate). This affords 19.7 g (60% of theory) of the desired compound.

$^1$H NMR (400 MHz, DMSO-$d_6$, δ/ppm): 8.96 (dd, 1H), 7.96 (dd, 1H), 7.69 (d, 1H), 7.66-7.61 (m, 5H), 7.48-7.38 (m, 7H), 7.19 (d, 1H), 4.89-4.80 (m, 1H), 4.28-4.19 (m, 1H), 3.92-3.84 (m, 1H), 3.80-3.68 (m, 2H), 3.65-3.25 (m, 8H), 2.08-1.98 (m, 2H), 1.01 (s, 9H).

HPLC (Method 2): $R_t$=6.27 min.
MS (ESIpos, m/z): 785 (M+H)$^+$.

Example 74A

1-[2-(Ethoxymethyl)-4-nitrophenyl]piperidin-2-one

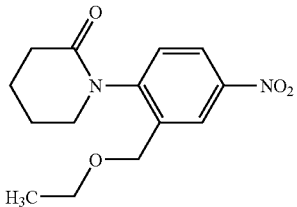

248 mg (2.51 mmol) of piperidin-2-one are dissolved in 10 ml of anhydrous dimethyl sulfoxide and admixed with 338 g (3.01 mmol) of potassium tert-butoxide. After 1 h, 500 mg of example 32A are added and the mixture is heated to 80° C. for 16 h. The mixture is allowed to cool and admixed with saturated sodium chloride solution. The mixture is extracted repeatedly with dichloromethane, and the organic phase is washed twice with water and twice with saturated sodium chloride solution, dried over sodium sulfate, filtered and concentrated to dryness under reduced pressure. The residue is dissolved in 5 ml of dimethyl sulfoxide and purified by preparative HPLC with a gradient of water and acetonitrile. The product fractions are combined and concentrated to dryness under reduced pressure. This affords 162 mg (23% of theory) of the desired product.

$^1$H NMR (400 MHz, DMSO-$d_6$, δ/ppm): δ=8.3 (d, 1H), 8.2 (dd, 1H), 7.55 (d, 1H), 4.45 (m, 2H), 3.7 (b, 1H), 3.5 (q, 2H), 3.4 (b, 1H), 2.4 (b, 2H), 1.9 (b, 4H), 1.15 (t, 3H).

LC-MS (Method 6): $R_t$=1.99 min
MS (ESIpos): m/z=279 (M+H)$^+$

Example 75A

1-[4-Amino-2-(ethoxymethyl)phenyl]piperidin-2-one

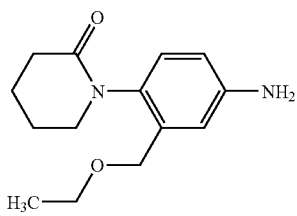

160 mg (0.58 mmol) of example 74A are dissolved in 10 ml of a 1:1 mixture of ethanol and ethyl acetate, and admixed with 181 mg (2.17 mmol) of ammonium formate and 20 mg of palladium on carbon. The mixture is heated to 80° C. for 30 min, allowed to cool and filtered through silica gel. It is washed with ethyl acetate and ethanol, and the filtrate is concentrated to dryness under reduced pressure. This affords 147 mg (99% of theory) of the desired product.

LC-MS (Method 6): $R_t$=1.04 min

MS (ESIpos): m/z=249 (M+H)$^+$

Example 76A 4-(2-Methyl-4-nitrophenyl)-1,4-oxazepan-5-one

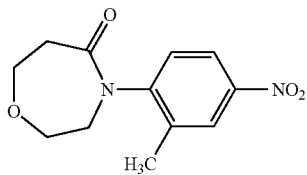

3.32 g (15.6 mmol) of potassium phosphate are mixed with 0.5 g (2.6 mmol) of copper(I) iodide in a round-bottom flask, and baked out and filled with argon in repeated alternation. Subsequently, 10 ml of anhydrous dioxane, 1.5 g (13.0 mmol) of 1,4-oxazepan-5-one, 3.43 g (13.0 mmol) of 1-iodo-2-methyl-4-nitrobenzene and 0.46 g (5.21 mmol) of N,N-dimethylethylenediamine are added, and the mixture is heated to 110° C. for 15 h. The mixture is allowed to cool and filtered through silica gel, and the silica gel is washed with dioxane. The combined filtrates are concentrated to dryness under reduced pressure. The residue is dissolved in acetonitrile and purified by preparative HPLC with a gradient of water and acetonitrile. The product fractions are combined and concentrated to dryness under reduced pressure. This affords 430 mg (13% of theory) of the desired product.

$^1$H NMR (400 MHz, DMSO-d$_6$, δ/ppm): δ=8.2 (s, 1H), 8.1 (d, 1H), 7.5 (d, 1H), 3.9 (m, 5H), 3.8 (m, 1H), 2.9 (m, 1H), 2.8 (m, 1H), 2.3 (s, 3H).

LC-MS (Method 6): $R_t$=1.58 min

MS (ESIpos): m/z=251 (M+H)$^+$

Example 77A 4-(4-Amino-2-methylphenyl)-1,4-oxazepan-5-one

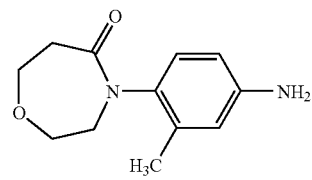

430 mg (1.72 mmol) of example 76A are dissolved in 40 ml of a 1:1 mixture of ethanol and ethyl acetate, and admixed with 650 mg (10.3 mmol) of ammonium formate and 50 mg of palladium on carbon. The mixture is heated to 80° C. and, after 45 min, allowed to cool and filtered through silica gel. It is washed with ethyl acetate and the filtrate is concentrated to dryness under reduced pressure. This affords 373 mg (98% of theory) of the desired product.

LC-MS (Method 7): $R_t$=1.84 min

MS (ESIpos): m/z=221 (M+H)$^+$

Example 78A 4-(2-Bromo-4-nitrophenyl)-1,4-oxazepan-5-one

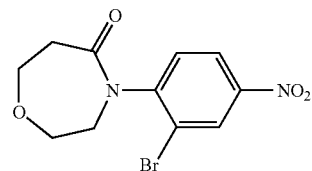

1.57 g (13.6 mmol) of 1,4-oxapan-5-one in 60 ml of DMSO are admixed at RT with 2.30 g (20.5 mmol) of potassium tert-butoxide, and the mixture is stirred at room temperature for 30 min. 3.00 g (13.6 mmol) of 2-bromo-1-fluoro-4-nitrobenzene are added and the mixture is stirred at 60° C. After 2 h, the heating bath is removed and then the mixture is stirred at RT for 18 h. Then it is added to 600 ml of water and 200 ml of saturated aqueous sodium chloride solution and extracted three times with 300 ml each time of ethyl acetate. The combined organic phases are dried over sodium sulfate. After filtration, the solvents are removed under reduced pressure. The residue is prepurified by chromatography on silica gel (1:1 cyclohexane/ethyl acetate; then ethyl acetate). After chromatographing again on silica gel (60:1 dichloromethane/methanol), 839 mg (20% of theory) of the desired compound are obtained.

$^1$H NMR (400 MHz, DMSO-d$_6$, δ/ppm): 8.50 (d, 1H), 8.28 (dd, 1H), 7.66 (d, 1H), 3.92-3.83 (m, 4H), 3.82-3.75 (m, 2H), 2.90-2.81 (m, 2H).

HPLC (Method 1): $R_t$=3.59 min.

MS (DCI, m/z): 316 (M+H)$^+$.

Example 79A 4-(2-Cyclopropyl-4-nitrophenyl)-1,4-oxazepan-5-one

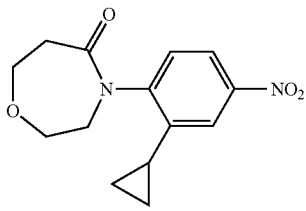

Under argon, 300 mg (0.95 mmol) of example 78A, 327 mg (3.81 mmol) of cyclopropylboronic acid, 33 mg (0.03 mmol) of tetrakis(triphenylphosphine)palladium (0) and 404 mg (1.90 mmol) potassium phosphate are suspended in 12 ml of toluene. The mixture is stirred at 120° C. for 3.5 h and then at RT for 10 h. Then it is admixed with 200 ml of water and 200 ml of ethyl acetate, the aqueous phase is extracted twice with ethyl acetate and the combined organic phases are washed once with water. After drying over sodium sulfate and filtration, the solvents are removed under reduced pressure. The reaction product (98% of theory) is converted further without further purification.

HPLC (Method 1): $R_t$=3.73 min.

MS (DCI, m/z): 277 (M+H)$^+$.

Example 80A 4-(4-Amino-2-cyclopropylphenyl)-1,4-oxazepan-5-one

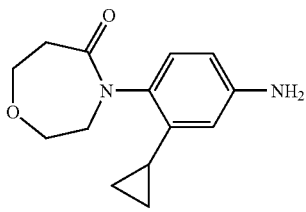

394 mg (1.42 mmol) of example 79A are dissolved in 23 ml of ethanol and admixed with 1.29 g (5.70 mmol) of tin chloride dihydrate. The mixture is heated to reflux for 20 min and then the reaction is ended by adding 100 ml of water. Sodium hydroxide solution is used to adjust the pH to 10, and extraction is effected three times with ethyl acetate. The combined organic phases are dried over sodium sulfate. Subsequently, the mixture is filtered and the filtrate is freed of the solvent. The reaction product is converted further without further purification.

LC-MS (Method 3): $R_t$=2.13 min.

MS (ESIpos, m/z): 247 (M+H)$^+$.

Example 81A 1-(2-Bromo-4-nitrophenyl)tetrahydropyrimidin-2 (1H)-one

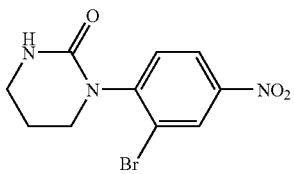

910 mg (9.09 mmol) of tetrahydropyrimidinone in 39 ml of DMSO are admixed at RT with 1.53 g (13.6 mmol) of potassium tert-butoxide, and the mixture is stirred at room temperature for 30 min. 2.00 g (9.09 mmol) of 2-bromo-1-fluoro-4-nitrobenzene are added and the mixture is stirred at 60° C. After 18 h, it is cooled and added to 600 ml of water and 160 ml of saturated aqueous sodium chloride solution. It is extracted three times with 300 ml each time of ethyl acetate, and the combined organic phases are dried over sodium sulfate. After filtration, the solvents are removed under reduced pressure and the residue is purified by chromatography on silica gel (60:1 dichloromethane/ethanol). This affords 481 mg (17% of theory) of the desired compound.

$^1$H NMR (400 MHz, DMSO-d$_6$, δ/ppm): 8.46 (d, 1H), 8.24 (dd, 1H), 7.65 (d, 1H), 6.83 (br. s, 1H), 3.58-3.44 (m, 2H), 3.31-3.23 (m, 2H), 2.03-1.90 (m, 2H).

HPLC (Method 5): $R_t$=2.84 min.

MS (ESIpos, m/z): 300 (M+H)$^+$.

Example 82A 1-(2-Ethyl-4-nitrophenyl)tetrahydropyrimidin-2 (1H)-one

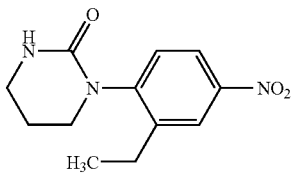

Under argon, 278 mg (0.92 mmol) of example 81A, 410 mg (5.56 mmol) of ethylboronic acid, 64 mg (0.06 mmol) of tetrakis(triphenylphosphine)palladium(0) and 393 mg (1.85 mmol) of potassium phosphate are suspended in 12 ml of toluene and stirred at 120° C. After 20 h, the mixture is admixed once again with 410 mg (5.56 mmol) of ethylboronic acid, 64 mg (0.06 mmol) of tetrakis(triphenylphosphine)palladium (0) and 393 mg (1.85 mmol) of potassium phosphate, and then stirred at 120° C. for 22 h. Then the mixture is admixed with 100 ml of water and 80 ml of ethyl acetate, and the aqueous phase is extracted twice with ethyl acetate and the combined organic phases are dried over sodium sulfate. After filtration, the solvents are removed under reduced pressure and the residue is purified by preparative HPLC with a gradient of water and acetonitrile. This affords 22 mg (7% of theory) of the desired product.

HPLC (Method 1): $R_t$=3.70 min.
MS (DCI, m/z): 250 (M+H)$^+$.

Example 83A 1-(4-Amino-2-ethylphenyl)tetrahydropyrimidin-2(1H)-one

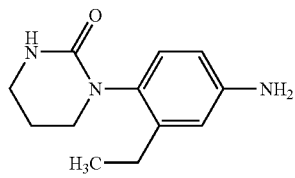

16.8 mg (0.067 mmol) of example 82A are dissolved in 1 ml of ethanol and admixed with 60.8 g (0.270 mmol) of tin chloride dihydrate. The mixture is heated to reflux for 20 min, before the reaction is ended by adding 15 ml of water. Sodium hydroxide solution is used to adjust the pH to 10, and extraction is then effected three times with ethyl acetate. The combined organic phases are dried over sodium sulfate. After filtration, the filtrate is freed of the solvent. The reaction product is converted without further purification.

LC-MS (Method 7): $R_t$=2.06 min.
MS (ESIpos, m/z): 220 (M+H)$^+$.

Example 84A 1-(2-Isopropyl-4-nitrophenyl)tetrahydropyrimidin-2(1H)-one

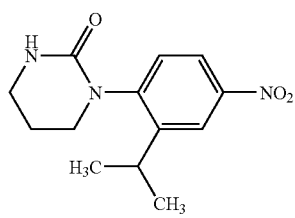

347 mg (3.47 mmol) of tetrahydropyrimidinone in 21 ml of DMSO are admixed at RT with 584 mg (5.21 mmol) of potassium tert-butoxide, and the mixture is stirred at RT for 45 min. 700 mg (3.82 mmol) of 1-fluoro-2-isopropyl-4-nitrobenzene are added and the mixture is stirred at 60° C. After 18 h, it is cooled and diluted with 250 ml of water. It is extracted three times with ethyl acetate and the combined organic phases are dried over sodium sulfate. After filtration, the solvents are removed under reduced pressure and the residue is purified by chromatography on silica gel (1:5→1:10 cyclohexane/ethyl acetate). This affords 140 mg (14% of theory) of the desired compound.

$^1$H NMR (400 MHz, DMSO-d$_6$, δ/ppm): 8.13 (d, 1H), 8.05 (dd, 1H), 7.46 (d, 1H), 6.68 (br. s, 1H), 3.69-3.60 (m, 1H), 3.37-3.21 (m, 2H), 3.14-3.04 (m, 2H), 2.03-1.93 (m, 2H), 1.20 (dd, 6H).

HPLC (Method 1): $R_t$=3.87 min.
MS (DCI, m/z): 264 (M+H)$^+$.

Example 85A 1-(4-Amino-2-isopropylphenyl)tetrahydropyrimidin-2(1H)-one

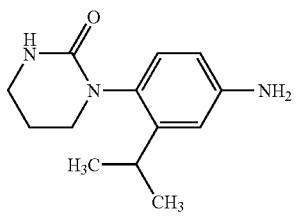

130 mg (0.493 mmol) of example 84A are dissolved in 8 ml of ethanol and admixed with 445 g (1.97 mmol) of tin chloride dihydrate. The mixture is heated to reflux for 20 h, before the reaction is ended by adding 100 ml of water. Sodium hydroxide solution is used to adjust the pH to 10, and extraction is then effected three times with ethyl acetate. The combined organic phases are dried over sodium sulfate. After filtration, the filtrate is freed of the solvent. The reaction product (82 mg) is converted without further purification.

HPLC (Method 1): $R_t$=2.95 min.
MS (ESIpos, m/z): 234 (M+H)$^+$.

Example 86A

1-{4-Nitro-2-[(1E)-prop-1-en-1-yl]phenyl}pyrimidin-2(1H)-one

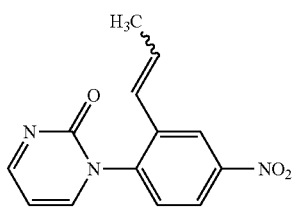

295 mg (2.76 mmol) of pyrimidin-2-one are dissolved in 10 ml of anhydrous N,N-dimethylformamide and admixed with 371 mg (3.3 mmol) of potassium tert-butoxide. After 1 h, 500 mg (2.76 mmol) of example 36A are added and the mixture is heated to 50° C. for 16 h. It is allowed to cool and the insoluble constituents are filtered off. The solution is purified by preparative HPLC with a gradient of water and acetonitrile. The product fractions are combined and concentrated to dryness under reduced pressure. This affords 45 mg (6% of theory) of the desired compound.

$^1$H NMR (400 MHz, DMSO-d$_6$, δ/ppm): δ=8.75 (m, 1H), 8.25-8.5 (m, 2H), 8.1 (m, 1H), 7.8 (d, 1H), 6.6 (m, 1H), 6.1 (m, 1H), 5.9 (m, 1H), 1.6-1.8 (dd, 3H).

Example 87A 1-(4-Amino-2-propylphenyl)tetrahydropyrimidin-2(1H)-one

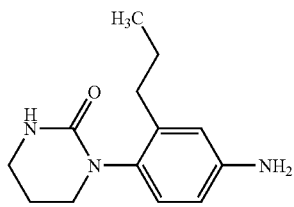

44 mg (0.17 mmol) of example 86A are dissolved in 8 ml of a 1:1 mixture of ethanol and ethyl acetate, and admixed with 65 mg (1.02 mmol) of ammonium formate and 50 mg of palladium on carbon. The mixture is heated to 80° C. After 45 min, it is allowed to cool and filtered through silica gel. Then it is washed with ethyl acetate and the filtrate is concentrated to dryness under reduced pressure. This affords 42 mg (100% of theory) of the desired compound.

LC-MS (Method 7): R$_t$=2.30 min

MS (ESIpos): m/z=234 (M+H)$^+$

Example 88A

2-Fluoro-5-nitrophenol

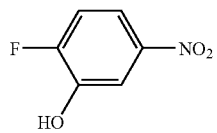

116 ml (116 mmol) of boron tribromide (1 molar solution in dichloromethane) are added dropwise at −10° C. over a period of 1 h to a solution of 5.00 g (29.2 mmol) of 1-fluoro-2-methoxy-4-nitrobenzene at such a rate that the temperature does not exceed −5° C. The solution is left at 0° C. for 5 h, then added slowly to 600 ml of ice-water and diluted with 100 ml of ethyl acetate. After phase separation, the aqueous phase is extracted twice with ethyl acetate. The combined organic phases are dried over sodium sulfate. After filtration, the solvents are removed under reduced pressure. The residue is purified by chromatography on silica gel (10:1 cyclohexane/ethyl acetate). This affords 1.45 g (30% of theory) of the desired compound.

$^1$H NMR (400 MHz, DMSO-d$_6$, δ/ppm): 10.99 (s, 1H), 7.78 (dd, 1H), 7.73 (ddd, 1H), 7.44 (dd, 1H).

HPLC (Method 1): R$_t$=3.60 min.

MS (DCI, m/z): 174 (M+NH$_4$)$^+$.

Example 89A

2-Ethoxy-1-fluoro-4-nitrobenzene

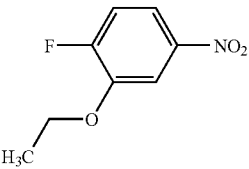

1.00 g (6.37 mmol) of example 88A are dissolved in 15 ml of DMF and admixed with 1.76 g (12.7 mmol) of potassium carbonate. Subsequently, 1.19 g (7.64 mmol) of iodoethane are added and the mixture is stirred at RT. After 1.5 h, it is admixed with 100 ml each of toluene and water, the phases are separated and the aqueous phase is extracted twice with 150 ml each time of toluene. The combined organic phases are washed with saturated aqueous sodium hydrogencarbonate solution and then dried over sodium sulfate. The mixture is freed of the solvent under reduced pressure, and the resulting solid is dried under high vacuum. This affords 1.06 g (89% of theory) of the desired product.

$^1$H NMR (400 MHz, DMSO-d$_6$, δ/ppm): δ=7.95 (dd, 1H), 7.89 (ddd, 1H), 7.52 (dd, 1H), 4.25 (q, 2H), 1.38 (t, 3H).

GC/MS (Method 9): R$_t$=6.42 min.

MS (EI-pos): m/z=185 (M+H)$^+$.

Example 90A 1-(2-Ethoxy-4-nitrophenyl)piperidin-2-one

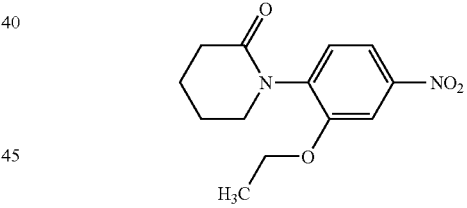

Under argon, 243 mg (2.45 mmol) of piperidin-2-one in 12 ml of DMF are admixed at 0° C. with 330 mg (2.95 mmol) of potassium tert-butoxide, and the mixture is stirred at room temperature for 30 min. 500 mg (2.70 mmol) of example 89A in 30 ml of DMF are added and the mixture is stirred at RT. After 18 h, it is added to 150 ml of saturated aqueous ammonium chloride solution and then extracted three times with 100 ml each time of ethyl acetate. The combined organic phases are washed with 200 ml of water and then dried over sodium sulfate. After filtration, the solvents are removed under reduced pressure. The residue is purified by chromatography on silica gel (1:5 cyclohexane/ethyl acetate). This affords 256 mg (39% of theory) of the desired compound.

$^1$H NMR (400 MHz, DMSO-d$_6$, δ/ppm): 7.89-7.81 (m, 2H), 7.50-7.42 (m, 1H), 4.18 (q, 2H), 3.47 (t, 2H), 2.38 (t, 2H), 1.92-1.78 (m, 4H), 1.33 (t, 3H).

HPLC (Method 1): R$_t$=3.93 min.

MS (DCI, m/z): 265 (M+H)$^+$.

Example 91A

1-(4-Amino-2-ethoxyphenyl)piperidin-2-one

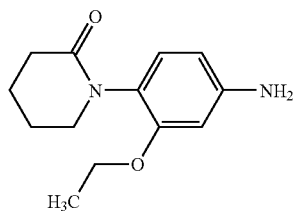

235 mg (0.889 mmol) of the product from example 90A are dissolved in 40 ml of THF and admixed with 50 mg of 10% palladium on activated carbon. Hydrogenation is effected in a hydrogen atmosphere under standard pressure overnight, then the mixture is filtered with suction through kieselguhr, washed three times with THF and concentrated cautiously under reduced pressure. This affords 262 mg of crude product, which is converted further without purification.

$^1$H NMR (400 MHz, DMSO-d$_6$, δ/ppm): 6.68 (d, 1H), 6.22 (d, 1H), 6.08 (dd, 1H), 5.06 (s. 2H), 3.88 (q, 2H), 3.38-3.28 (m, 2H), 2.33-2.24 (m, 2H), 1.85-1.70 (m, 4H), 1.26 (t, 3H).
LC-MS (Method 6): R$_t$=1.37 min.
MS (ESIpos, m/z): 235 (M+H)$^+$.

Example 92A

3-({[tert-Butyl(diphenyl)silyl]oxy}methyl)piperidin-2-one

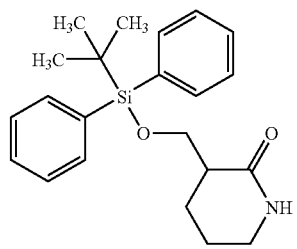

A solution of 5.00 g (38.7 mmol) of 3-hydroxymethylpiperidin-2-one in 40 ml of N,N-dimethylformamide is admixed successively with 3.16 g (46.5 mmol) of imidazole, and dropwise with 11 ml (42.6 mmol) of tert-butyl(diphenyl)silyl chloride. After stirring at RT for 3 hours, the mixture is admixed with approx. 400 ml of water and extracted three times with ethyl acetate. The combined organic extracts are washed successively with saturated ammonium chloride solution, water and saturated sodium chloride solution. After drying over anhydrous magnesium sulfate, the mixture is filtered and the filtrate is freed of the solvent under reduced pressure. The resulting residue is purified by suction filtration through silica gel with 20:1→1:1 cyclohexane/ethyl acetate as the eluent. This affords 9.43 g (66% of theory) of the title compound.

$^1$H NMR (400 MHz, CDCl$_3$, δ/ppm): 7.69-7.65 (m, 4H), 7.42-7.34 (m, 6H), 5.82 (s, broad, 1H), 4.03 (dd, 1H), 3.93 (dd, 1H), 3.32-3.28 (m, 2H), 2.53-2.48 (m, 1H), 2.07-1.99 (m, 1H), 1.96-1.87 (m, 2H), 1.78-1.68 (m, 1H), 1.04 (s, 9H).
HPLC (Method 3): R$_t$=2.79 min.
MS (ESIpos, m/z): 368 (M+H)$^+$.

Example 93A

1-(4-Amino-2-chlorophenyl)-3-({[tert-butyl(diphenyl)silyl]oxy}methyl)piperidin-2-one

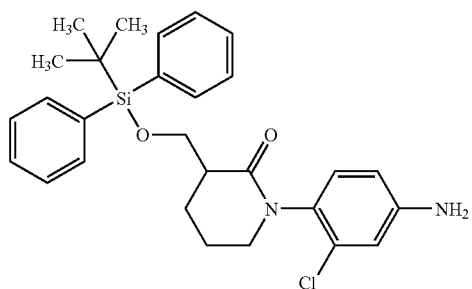

2.75 g (10.8 mmol) of 3-chloro-4-iodoaniline are dissolved in 20 ml of anhydrous dioxane and admixed successively with 4.98 g (13.5 mmol) of the compound from example 92A, 103 mg (0542 mmol) of copper(I) iodide, 4.61 g (21.7 mmol) of potassium phosphate and 116 µl (1.085 mmol) of N,N'-dimethylethylenediamine. The reflux apparatus is inertized by repeated application of a gentle vacuum and flushing with argon. The reaction mixture is heated to reflux for 15 hours. After this time, it is allowed to cool to RT. It is admixed with water and extracted with ethyl acetate. The organic extract is washed successively with water and saturated sodium chloride solution. Then it is dried over anhydrous magnesium sulfate and filtered, and the filtrate is freed of the solvent under reduced pressure. The crude product thus obtained is first purified by suction filtration through silica gel with 20:1→1:4 cyclohexane/ethyl acetate as the eluent. This affords 3.12 g of a still-contaminated product which is purified further by means of preparative HPLC with an acetonitrile/water mixture. This affords 0.71 g (13% of theory) of the title compound.

$^1$H NMR (400 MHz, DMSO-d$_6$, δ/ppm): 7.67-7.62 (m, 4H), 7.48-7.40 (m, 6H), 6.91 and 6.81 (2 d, together 1H), 6.67 and 6.62 (2 d, together 1H), 6.50 and 6.47 (2 dd, together, 1H), 5.41 (s, broad, 2H), 4.08-4.00 (m, 1H), 3.78-3.73 (m, 1H), 3.50-3.41 (m, 1H), 3.40-3.32 (m, 1H, partly obscured by the water signal), 2.07-1.96 (m, 3H), 1.92-1.81 (m, 2H), 1.01 and 1.00 (2 s, together 9H).
HPLC (Method 5): R$_t$=3.26 min.
MS (ESIpos, m/z): 493/495 ($^{35}$Cl/$^{37}$Cl) (M+H)$^+$.

Example 94A

N-[(2R)-3-({4-[3-({[tert-Butyl(diphenyl)silyl]oxy}methyl)-2-oxopiperidin-1-yl]-3-chlorophenyl}-amino)-2-hydroxypropyl]-5-chlorothiophene-2-carboxamide

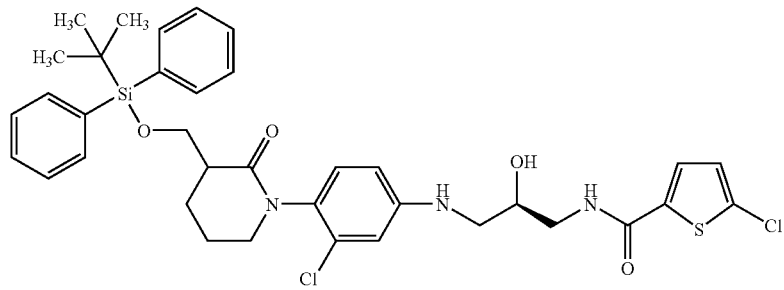

A solution of 665 mg (1.35 mmol) of the compound from example 93A and 323 mg (1.48 mmol) of the compound from example 1A in 3 ml of acetonitrile is admixed with 452 mg (2.02 mmol) of magnesium perchlorate and stirred at RT for 15 hours. Without pretreatment, the mixture is purified by means of preparative HPLC with an acetonitrile/water mixture. This affords 871 mg (91% of theory) of the title compound.

$^1$H NMR (400 MHz, DMSO-$d_6$, δ/ppm): 8.60 (t, 1H), 7.68-7.62 (m, 5H), 7.48-7.40 (m, 6H), 7.18 (d, 1H), 6.97 and 6.86 (2 d, together 1H), 6.70 and 6.64 (2 d, together 1H), 6.56 and 6.53 (2 dd, together, 1H), 5.98 (t, broad, 1H), 5.11 (d, 1H), 4.09-4.01 (m, 1H), 3.80-3.73 (m, 2H), 3.51-3.42 (m, 1H), 3.38-3.22 (m, 2H, partly obscured by the water signal), 3.71-3.08 (m, 1H), 3.00-2.93 (m, 1H), 2.58-2.52 (m, 1H), 2.08-1.96 (m, 3H), 1.91-1.82 (m, 2H), 1.01 and 1.00 (2 s, together 9H).

HPLC (Method 4): $R_t$=3.40 min.
MS (ESIpos, m/z): 710/712/714 (Cl$_2$, $^{35}$Cl/$^{37}$Cl) (M+H)$^+$.

Example 95A

N-[((5S)-3-{4-[3-({[tert-Butyl(diphenyl)silyl]oxy}methyl)-2-oxopiperidin-1-yl]-3-chlorophenyl}-2-oxo-1,3-oxazolidin-5-yl)methyl]-5-chlorothiophene-2-carboxamide

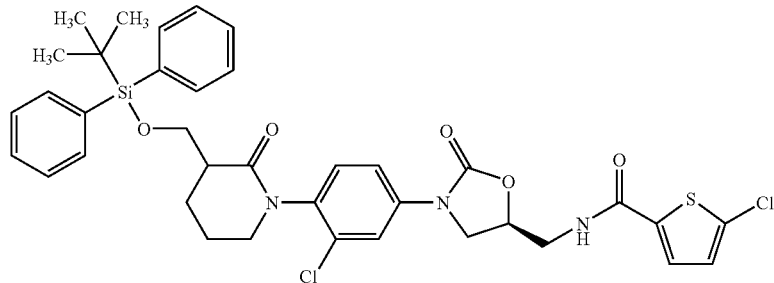

A solution of 850 mg (1.196 mmol) of the compound from example 94A and 387 mg (2.39 mmol) of carbonyldiimidazole in 30 ml of butyronitrile is admixed with 3 mg (0.024 mmol) of 4-dimethylaminopyridine and heated to reflux. After 15 hours, the majority of the solvent is removed on a rotary evaporator. The product is isolated further by means of preparative HPLC with an acetonitrile/water mixture. This affords 605 mg (69% of theory) of the title compound.

$^1$H NMR (400 MHz, DMSO-$d_6$, δ/ppm): 8.97 (t, 1H), 7.80 and 7.72 (2 d, together 1H), 7.68 (d, 1H), 7.66-7.63 (m, 4H), 7.52-7.41 (m, 7H), 7.37 and 7.23 (2 d, together 1H), 7.19 (d, 1H), 4.88-4.82 (m, 1H), 4.22-4.17 (m, 1H), 4.09-4.03 (m, 1H), 3.89-3.83 (m, 1H), 3.81-3.74 (m, 1H), 3.61-3.37 (m, 3H), 2.64-2.57 (m, 1H), 2.11-2.00 (m, 3H), 1.97-1.86 (m, 2H), 1.02 and 1.00 (2 s, together 9H).

HPLC (Method 4): $R_t$=3.44 min.
MS (ESIpos, m/z): 736/738/740 (Cl$_2$, $^{35}$Cl/$^{37}$Cl) (M+H)$^+$.

Example 96A

3-Allylpiperidin-2-one

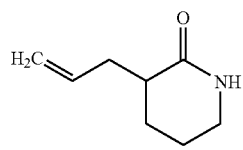

A solution of 5.00 g (50.4 mmol) of piperidin-2-one in 75 ml of anhydrous tetrahydrofuran is admixed dropwise at a temperature of 0° C. with 69 ml (110 mmol) of a 1.6 molar solution of n-butyllithium in hexane. After a further hour at 0° C., the reaction mixture is cooled to −78° C. and then admixed dropwise with a solution of 5.3 ml (60.5 mmol) of allyl bromide in 25 ml of anhydrous tetrahydrofuran. After the addition has ended, the reaction mixture is warmed to RT within 45 minutes. Then 500 ml of water are added, and the mixture is extracted three times with approx. 200 ml each time of ethyl acetate. The combined organic extracts are washed successively with water and saturated sodium chloride solution, and dried over anhydrous magnesium sulfate. After filtration, the solvent is removed on a rotary evaporator. This affords 4.89 g (70% of theory) of the title compound.

$^1$H NMR (400 MHz, CDCl$_3$, δ/ppm): 5.99 (s, broad, 1H), 5.83-5.72 (m, 1H), 5.10-5.03 (m, 2H), 3.31-3.27 (m, 2H), 2.70-2.64 (m, 1H), 2.38-2.24 (m, 2H), 1.96-1.88 (m, 2H), 1.77-1.67 (m, 1H), 1.59-1.51 (m, 1H).

HPLC (Method 1): R$_t$=3.57 min.

MS (DCI, NH$_3$, m/z): 140 (M+H)$^+$, 157 (M+NH$_4$)$^+$, 174 (M+N$_2$H$_7$)$^+$.

Example 97A

3-Allyl-1-(4-amino-2-chlorophenyl)piperidin-2-one

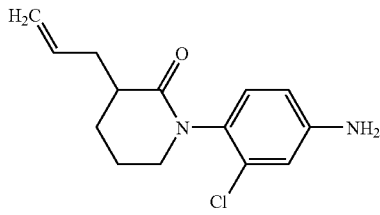

Analogously to the process described under example 93A, 6.00 g (23.7 mmol) of 3-chloro-4-iodoaniline and 4.11 g (29.6 mmol) of the compound from example 96A are used to obtain 1.57 g (25% of theory) of the title compound. The purification is effected by suction filtration using silica gel with 2:1→1:2 cyclohexane/ethyl acetate as the eluent.

$^1$H NMR (400 MHz, CDCl$_3$, δ/ppm): 6.98 and 6.95 (two d, together 1H), 6.75 and 6.73 (two d, together 1H), 6.57 and 6.54 (two dd, together 1H), 5.90-5.78 (m, 1H), 5.12-5.03 (m, 2H), 3.73 (s, broad, 2H), 3.51-3.38 (m, 2H), 2.78-2.68 (m, 1H), 2.53-2.31 (m, 2H), 2.07-1.85 (m, 4H).

HPLC (Method 1): R$_t$=3.88 min.

MS (DCI, NH$_3$, m/z): 265/267 ($^{35}$Cl/$^{37}$Cl) (M+H)$^+$.

Example 98A

N-((2R)-3-{[4-(3-Allyl-2-oxopiperidin-1-yl)-3-chlorophenyl]amino}-2-hydroxypropyl)-5-chlorothiophene-2-carboxamide

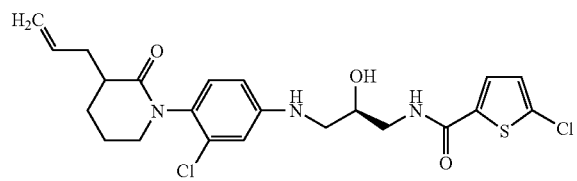

In analogy to the process described under example 94A, 1.40 g (5.29 mmol) of the compound from example 97A are used to obtain 2.09 g (82% of theory) of the title compound. The purification is effected by suction filtration using silica gel with 5:1→1:4 cyclohexane/ethyl acetate as the eluent.

$^1$H NMR (400 MHz, CDCl$_3$, δ/ppm): 7.32-7.31 (m, 1H), 7.22-7.19 (m, 1H), 6.93-6.84 (m, 2H), 6.56 (s, 1H), 6.43-6.39 (m, 1H), 5.87-5.73 (m, 1H), 5.12-5.07 (m, 2H), 4.58-4.52 (m, 1H), 4.15-4.09 (m, 1H), 3.71-3.64 (m, 1H), 3.60-3.40 (m, 2H), 3.33-3.30 (m, 2H), 3.01-2.96 (m, 2H), 2.73-2.63 (m, 1H), 2.59-2.48 (m, 1H), 2.46-2.32 (m, 1H), 2.07-1.86 (m, 3H), 1.80-1.67 (m, 1H).

HPLC (Method 2): R$_t$=4.38 min.

MS (ESIpos, m/z): 482/484/486 (Cl$_2$, $^{35}$Cl/$^{37}$Cl) (M+H)$^+$.

Example 99A

3-Allyl-1-(4-amino-2-methylphenyl)piperidin-2-one

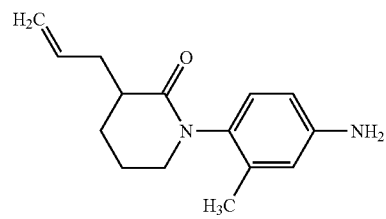

Analogously to the process described under example 93A, 2.68 g (11.5 mmol) of 4-iodo-3-methylaniline and 2.0 g (14.3 mmol) of the compound from example 96A are used to obtain, after preparative HPLC, 1.31 g (47% of theory) of the title compound.

HPLC (Method 1): R$_t$=3.76 and 3.98 min.

MS (DCI, NH$_3$, m/z): 245 (M+H)$^+$, 262 (M+NH$_4$)$^+$.

Example 100A

N-((2R)-3-{[4-(3-Allyl-2-oxopiperidin-1-yl)-3-methylphenyl]amino}-2-hydroxypropyl)-5-chlorothiophene-2-carboxamide

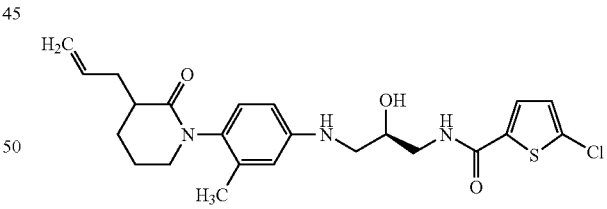

In analogy to the process described under example 94A, 1.3 g (5.32 mmol) of the compound from example 99A are used to obtain, after preparative HPLC 990 mg (83% of theory) of the title compound.

$^1$H NMR (400 MHz, DMSO-d$_6$, δ/ppm): 8.60 (t, 1H), 7.69 (d, 1H), 7.18 (d, 1H), 6.79 and 7.75 (2 d, together, 1H), 6.44-6.39 (m, 2H), 5.83-73 (m, 1H), 5.48 and 5.03 (2 s, broad, together 1H), 5.10-5.05 (m, 2H), 3.81-3.76 (m, 1H), 3.48-3.40 (m, 1H), 3.37-3.22 (m, 4H, partly obscured by the water signal), 3.11-3.05 (m, 1H), 2.98-2.92 (m, 1H), 2.57-2.47 (m, 1H, partly obscured by the DMSO signal), 2.43-2.35 (m, 1H), 2.33-2.18 (m, 1H), 1.93 and 1.92 (2 s, together 3H), 1.92-1.87 (m, 2H), 1.86-1.77 (m, 1H), 1.61-1.53 (m, 1H).

HPLC (Method 2): $R_t$=4.16 min.

MS (DCI, NH$_3$, m/z): 462/464 ($^{35}$Cl/$^{37}$Cl) (M+H)$^+$, 479/481 (M+NH$_4$)$^+$.

Example 101A

N-({(5S)-3-[4-(3-Allyl-2-oxopiperidin-1-yl)-3-chlorophenyl]-2-oxo-1,3-oxazolidin-5-yl}methyl)-5-chlorothiophene-2-carboxamide

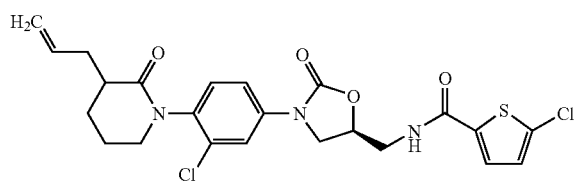

Analogously to the process described under example 95A, 2.05 g (4.25 mmol) of the compound from example 98A are converted to 1.44 g (67% of theory) of the title compound as a diastereomer mixture. The purification is effected by suction filtration using silica gel with 5:1→1:3 cyclohexane/ethyl acetate as the eluent.

$^1$H NMR (400 MHz, CDCl$_3$, δ/ppm): 7.72-7.67 (m, 1H), 7.44-7.37 (m, 1H), 7.33-7.31 (m, 1H), 7.23-7.18 (m, 1H), 6.92-6.87 (m, 2H), 5.88-5.77 (m, 1H), 5.12-5.06 (m, 2H), 4.82-4.77 (m, 1H), 4.06-3.98 (m, 1H), 3.82-3.74 (m, 2H), 3.71-3.63 (m, 1H), 3.61-3.42 (m, 2H), 2.77-2.66 (m, 1H), 2.60-2.50 (m, 1H), 2.47-2.32 (m, 1H), 2.09-1.88 (m, 3H), 1.81-1.63 (m, 1H).

HPLC (Method 2): $R_t$=4.50 min.

MS (ESIpos, m/z): 508/510/512 (Cl$_2$, $^{35}$Cl/$^{37}$Cl) (M+H)$^+$.

The diastereomer mixture can be separated on the preparative scale chromatographically into the pure diastereomers. To this end, 1.10 g of the compound from example 101A are dissolved in 16 ml of the eluent and chromatographed in four portions. This affords 386 mg (35% of theory) of the title compound (diastereomer 2) and 417 mg (38% of theory) of diastereomer 1.

Method: column: Daicel Chiralpak AD-H, 5 μm, 250 mm×20 mm; eluent: ethanol+1% water+0.2% trifluoroacetic acid; flow rate: 15 ml/min; temperature: 40° C.; UV detection: 220 nm.

Retention time: 10.5 min (diastereomer 1), 18.8 min (diastereomer 2)

$^1$H NMR (400 MHz, CDCl$_3$, δ/ppm): 7.72 and 7.67 (2 d, together 1H), 7.43 and 7.39 (2 dd, together 1H), 7.33 and 7.32 (2 d, together 1H), 7.22 and 7.19 (2 d, together 1H), 6.89 (d, 1H), 6.81 (t, 1H), 5.88-5.77 (m, 1H), 5.12-5.06 (m, 2H), 4.83-4.78 (m, 1H), 4.07-4.00 (m, 1H), 3.80 (dd, 2H), 3.71-3.63 (m, 1H), 3.62-3.41 (m, 2H), 2.77-2.66 (m, 1H), 2.62-2.51 (m, 1H), 2.47-2.32 (m, 1H), 2.09-1.90 (m, 3H), 1.82-1.68 (m, 1H).

HPLC (Method 4): $R_t$=2.60 min.

MS (ESIpos, m/z): 508/510/512 (Cl$_2$, $^{35}$Cl/$^{37}$Cl) (M+H)$^+$.

Example 102A

N-({(5S)-3-[4-(3-Allyl-2-oxopiperidin-1-yl)-3-methylphenyl]-2-oxo-1,3-oxazolidin-5-yl}methyl)-5-chlorothiophene-2-carboxamide

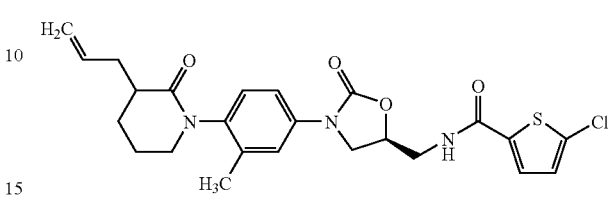

Analogously to the process described under example 95A, 980 mg (2.12 mmol) of the compound from example 100A are converted to 790 mg (76% of theory) of the title compound.

$^1$H NMR (400 MHz, CDCl$_3$, δ/ppm): 7.41-7.37 (m, 2H), 7.33 and 7.32 (2 d, together 1H), 7.12-7.06 (m, 1H), 6.88 (d, 1H), 6.85-6.77 (m, 1H), 5.87-5.77 (m, 1H), 5.12-5.08 (m, 2H), 4.79-4.70 (m, 1H), 4.03-3.98 (m, 1H), 3.82-3.73 (m, 2H), 3.64-3.50 (m, 2H), 3.44-3.22 (m, 1H), 2.77-2.66 (m, 1H), 2.59-2.51 (m, 1H), 2.47-2.31 (m, 1H), 2.19 and 2.18 (2 s, together 3H), 2.09-1.98 (m, 2H), 1.96-1.87 (m, 1H), 1.79-1.68 (m, 1H).

HPLC (Method 2): $R_t$=4.56 min.

MS (ESIpos, m/z): 488/490 ($^{35}$Cl/$^{37}$Cl) (M+H)$^+$.

Example 103A 1-(5-Chloro-2-methyl-4-nitrophenyl)-3-methylpyridin-2(1H)-one

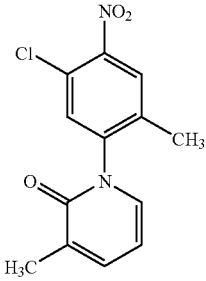

1.50 g (13.8 mmol) of 2-hydroxy-3-methylpyridine in 70 ml of DMF are admixed at 0° C. with 2.31 g (20.6 mmol) of potassium tert-butoxide, and the mixture is stirred at room temperature for 30 min. 2.87 g (15.1 mmol) of 2-chloro-4-fluoro-5-methylnitrobenzene are added while continuing to stir at RT. After 17 h, the mixture is admixed with 1000 ml of water and then extracted three times with ethyl acetate. The combined organic phases are dried over sodium sulfate and, after filtration, the solvents are removed under reduced pressure. The residue is purified by chromatography on silica gel (2:1 cyclohexane/ethyl acetate). This affords 2.15 g (56% of theory) of the desired compound.

$^1$H NMR (400 MHz, DMSO-d$_6$, δ/ppm): 8.18 (s, 1H), 7.85 (s, 1H), 7.48-7.44 (m, 2H), 6.31 (dd, 1H), 2.08 (s, 3H), 2.05 (s, 3H).

HPLC (Method 1): R$_t$=4.05 min.
MS (DCI, m/z): 279 (M+H)$^+$.

Example 104A

3-Methyl-1-{2-methyl-5-[methyl(propyl)amino]-4-nitrophenyl}pyridin-2(1H)-one

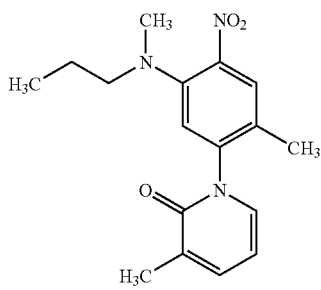

400 mg (1.44 mmol) of example 103A and 315 mg (4.31 mmol) of 1-methylpropylamine in 10 ml of DMF are stirred at 120° C. After 4 h, the mixture is admixed with 200 ml of water and then extracted three times with ethyl acetate. The combined organic phases are dried over sodium sulfate and, after filtration, the solvents are removed under reduced pressure. The residue is purified by preparative HPLC with an acetonitrile/water mixture. This affords 216 mg (48% of theory) of the desired compound.

$^1$H NMR (400 MHz, DMSO-d$_6$, δ/ppm): 7.77 (s, 1H), 7.70-7.45 (m, 2H), 7.14 (s, 1H), 6.26 (dd, 1H), 3.05 (t, 2H), 2.72 (s, 3H), 2.07 (s, 3H), 2.05 (s, 3H), 1.51 (dt, 2H), 0.81 (t, 3H).
HPLC (Method 2): R$_t$=4.36 min.
MS (DCI, m/z): 316 (M+H)$^+$.

Example 105A

1-{4-Amino-2-methyl-5-[methyl(propyl)amino]phenyl}-3-methylpyridin-2(1H)-one

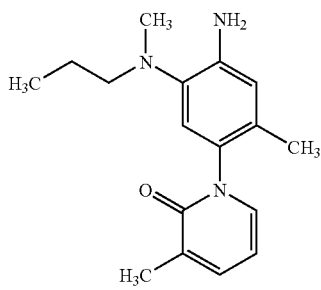

200 mg (0.63 mmol) of example 104A are dissolved in a mixture of 5 ml of THF and 5 ml of ethanol. Then 7.7 mg (0.03 mmol) of platinum(IV) oxide hydrate are added and hydrogenation is effected at RT in a hydrogen atmosphere under standard pressure for 17 h. Subsequently, the mixture is filtered and the filtrate is freed of the solvent. The reaction product is converted further without further purification.

$^1$H NMR (400 MHz, DMSO-d$_6$, δ/ppm): 7.37-7.33 (m, 1H), 7.29-7.26 (m, 1H), 6.67 (s, 1H), 6.58 (s, 1H), 6.15 (dd, 1H), 4.86 (s, 2H), 2.71 (t, 2H), 2.01 (s, 3H), 1.82 (s, 3H), 1.45 (dt, 2H), 1.36 (s, 3H), 0.85 (t, 3H).
HPLC (Method 4): R$_t$=1.75 min.
MS (ESIpos, m/z): 286 (M+H)$^+$.

Example 106A

1-{5-[[2-(Dimethylamino)ethyl](methyl)amino]-2-methyl-4-nitrophenyl}-3-methylpyridin-2(1H)-one

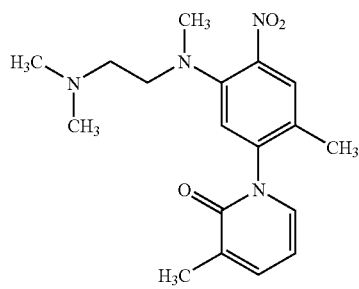

400 mg (1.44 mmol) of example 103A and 880 mg (8.61 mmol) of N,N,N'-trimethylethane-1,2-diamine in 10 ml of DMF are stirred at 120° C. After 2 h, the mixture is admixed with 200 ml of water and then extracted three times with dichloromethane. The combined organic phases are dried over sodium sulfate and, after filtration, the solvents are removed under reduced pressure. The residue is purified by preparative HPLC with an acetonitrile/water mixture. This affords 349 mg (71% of theory) of the desired compound.

$^1$H NMR (400 MHz, DMSO-d$_6$, δ/ppm): 7.76 (s, 1H), 7.47-7.40 (m, 2H), 7.15 (s, 1H), 6.27 (dd, 1H), 3.18 (t, 2H), 2.76 (s, 3H), 2.43 (t, 2H), 2.14 (s, 6H), 2.05 (s, 3H), 1.95 (s, 3H).
HPLC (Method 2): R$_t$=3.66 min.
MS (DCI, m/z): 345 (M+H)$^+$.

Example 107A

1-{4-Amino-5-[[2-(dimethylamino)ethyl](methyl)amino}-2-methylphenyl]-3-methylpyridin-2(1H)-one

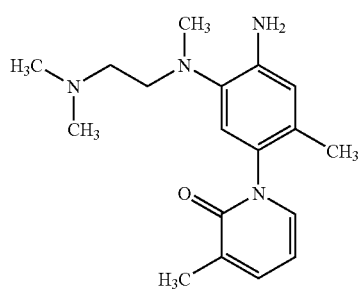

325 mg (0.94 mmol) of example 106A are dissolved in a mixture of 10 ml of THF and 10 ml of ethanol. Then 11 mg (0.05 mmol) of platinum(IV) oxide hydrate are added and hydrogenation is effected at RT in a hydrogen atmosphere under standard pressure for 17 h. Subsequently, the mixture is filtered and washed with THF, and the filtrate is freed of the solvent. The reaction product is converted further without further purification.

$^1$H NMR (400 MHz, DMSO-d$_6$, δ/ppm): 7.29-7.25 (m, 1H), 7.38-7.33 (m, 1H), 6.68 (s, 1H), 6.55 (s, 1H), 6.15 (dd, 1H), 5.75 (s, 2H), 2.79 (t, 2H), 2.55 (s, 3H), 2.39 (t, 2H), 2.21 (s, 6H), 2.02 (s, 3H), 1.83 (s, 3H).

HPLC (Method 1): R$_t$=3.26 min.

MS (DCI, m/z): 315 (M+H)$^+$.

Example 108A

3-Methyl-1-(2-methyl-4-nitro-5-propoxyphenyl)pyridin-2(1H)-one

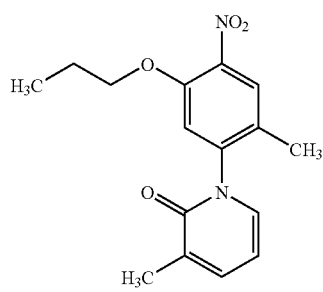

300 mg (1.08 mmol) of example 103A and 151 mg (2.69 mmol) of potassium hydroxide are stirred in 7.5 ml of 1-propanol at 60° C. for 30 h. Then the mixture is admixed with 200 ml of water and extracted three times with ethyl acetate. The combined organic phases are dried over sodium sulfate and, after filtration, the solvents are removed under reduced pressure. The product thus obtained is converted further without purification.

$^1$H NMR (400 MHz, DMSO-d$_6$, δ/ppm): 7.92 (s, 1H), 7.47-7.41 (m, 2H), 7.33 (s, 1H), 6.29 (dd, 1H), 4.09 (t, 2H), 2.08 (s, 3H), 1.98 (s, 3H), 1.75-1.66 (m, 2H), 0.95 (t, 3H).

HPLC (Method 1): R$_t$=4.33 min.

MS (DCI, m/z): 320 (M+H)$^+$.

Example 109A 1-(4-Amino-2-methyl-5-propoxyphenyl)-3-methylpyridin-2(1H)-one

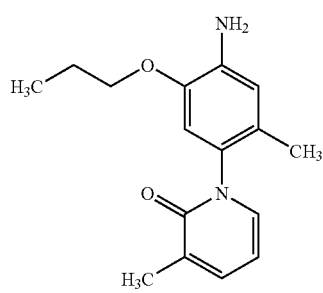

400 mg (1.32 mmol) of example 108A are dissolved in a mixture of 10 ml of THF and 10 ml of ethanol. Then 16 mg (0.07 mmol) of platinum(IV) oxide hydrate are added, and hydrogenation is effected at RT in a hydrogen atmosphere under standard pressure for 3 days. Subsequently, the mixture is filtered and washed with THF, and the filtrate is freed of the solvent. The reaction product is converted further without further purification.

HPLC (Method 3): R$_t$=1.68 min.

MS (ESIpos, m/z): 273 (M+H)$^+$.

Example 110A

1-Benzyl-3,5-dichloropyrazin-2(1H)-one

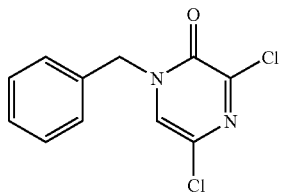

To a solution of 92 g (725 mmol) of oxalyl chloride in 188 ml of 1,2-dichlorobenzene are added 26.5 g (145 mmol) of N-benzylaminoacetonitrile. The solution is heated to 60° C. for 20 min and to 90° C. for 6 h. It is allowed to cool and left at this temperature for 15 h. The solvent is removed under reduced pressure and the residue is eluted with silica gel and with a gradient from cyclohexane to 5:1 cyclohexane/ethyl acetate. The product fractions are combined and concentrated to dryness under reduced pressure. The residue is crystallized from diethyl ether. This affords 22 g (60% of theory) of the desired compound.

$^1$H NMR (400 MHz, CDCl$_3$, δ/ppm): δ=7.4 (m, 3H), 7.35 (m, 2H), 7.15 (s, 1H), 5.1 (s, 2H).

LC-MS (Method 3): R$_t$=2.04 min

MS (ESIpos): m/z=255 (M+H)$^+$

Example 111A

1-Benzyl-5-chloro-3-ethoxypyrazin-2(1H)-one

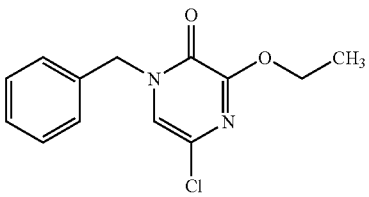

To a solution of 1.00 g (3.92 mmol) of example 110A in 8 ml of anhydrous ethanol are added 660 mg (7.8 mmol) of potassium ethoxide. After 2 h, 165 mg (196 mmol) of potassium ethoxide are added and, after a further 30 min, another 165 mg (196 mmol) of potassium ethoxide. After a further 30 min, the solvent is removed under reduced pressure and the residue is diluted with water. The mixture is extracted repeatedly with dichloromethane, and the combined organic phases are washed with saturated sodium chloride solution, dried over magnesium sulfate, filtered and concentrated to dryness under reduced pressure. This affords 1.0 g (96% of theory) of the desired compound.

$^1$H NMR (400 MHz, CDCl$_3$, δ/ppm): δ=7.4-7.3 (m, 5H), 6.8 (s, 1H), 5.05 (s, 2H), 4.4 (q, 2H), 1.45 (t, 3H).

LC-MS (Method 5): R$_t$=2.27 min

MS (ESIpos): m/z=265 (M+H)$^+$

Example 112A

3-Ethoxypyrazin-2(1H)-one

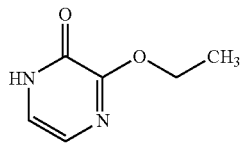

1.4 g (5.4 mmol) of example 111A are dissolved in 200 ml of a 1:1 mixture of ethanol and ethyl acetate. 200 mg of palladium on carbon are added. The mixture is heated at reflux for 1 h before, at this temperature, a further 200 mg of palladium on carbon and 2.1 g (32.5 mmol) of ammonium formate are added. After a further 30 min, another 200 mg of palladium on carbon and 2.1 g (32.5 mmol) of ammonium formate are added. The mixture is stirred at this temperature for a further 30 min, before it is allowed to cool and filtered through silica gel. The filtrate is concentrated to dryness under reduced pressure, and the residue is dissolved in methanol and purified by preparative HPLC with a gradient of water and acetonitrile. The product fractions are combined and concentrated to dryness under reduced pressure. This affords 579 mg (79% of theory) of the desired compound.

$^1$H NMR (400 MHz, DMSO-d$_6$, δ/ppm): δ=6.95 (d, 1H), 6.75 (d, 1H), 4.25 (q, 2H), 1.3 (t, 3H).
LC-MS (Method 6): $R_t$=2.17 min
MS (ESIpos): m/z=141 (M+H)$^+$

Example 113A

3-Ethoxy-1-(2-methyl-4-nitrophenyl)pyrazin-2(1H)-one

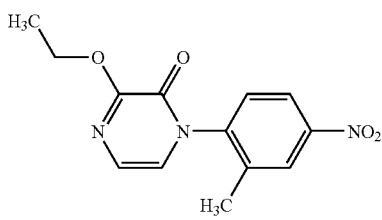

300 mg (2.14 mmol) of example 112A are dissolved in 7 ml of dimethyl sulfoxide and admixed at room temperature with 288 mg (2.6 mmol) of potassium tert-butoxide. The suspension is stirred at room temperature for 30 min, before 332 mg (2.14 mmol) of 1-fluoro-2-methyl-4-nitrobenzene are added and the reaction solution is heated to 80° C. for 20 h. It is diluted cautiously with water. The solution is extracted repeatedly with dichloromethane. The combined organic extracts are washed with water and saturated sodium chloride solution, dried over magnesium sulfate, filtered and concentrated under reduced pressure. The residue is crystallized from methanol and tert-butyl methyl ether. This affords 429 mg (72% of theory) of the desired compound.

$^1$H NMR (400 MHz, CDCl$_3$, δ/ppm): δ=8.25 (d, 1H), 8.2 (dd, 1H), 7.4 (d, 1H), 6.95 (d, 1H), 6.65 (d, 1H), 4.5 (m, 2H), 2.25 (s, 3H), 1.5 (t, 3H).

LC-MS (Method 5): $R_t$=1.90 min
MS (ESIpos): m/z=276 (M+H)$^+$

Example 114A 1-(4-Amino-2-methylphenyl)-3-ethoxypyrazin-2(1H)-one

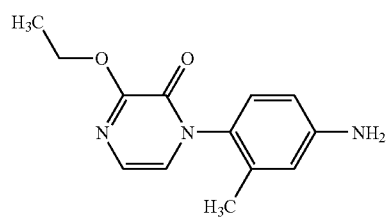

445 mg (1.62 mmol) of example 113A are dissolved in 64 ml of 1:1 mixture of ethanol and ethyl acetate and admixed with 611 mg (9.7 mmol) of ammonium formate and 50 mg of palladium on carbon. The mixture is heated to 80° C. After 1 h, it is allowed to cool and filtered through silica gel. It is washed with ethyl acetate and the filtrate is concentrated to dryness under reduced pressure. This affords 400 mg (100% of theory) of the desired compound.

$^1$H NMR (400 MHz, DMSO-d$_6$, δ/ppm): δ=7.0 (d, 1H), 6.85 (d, 1H), 6.8 (d, 1H), 6.5-6.4 (m, 2H), 5.3 (s, 2H), 4.3 (q, 2H), 1.8 (s, 3H) 1.3 (t, 3H).
LC-MS (Method 3): $R_t$=1.37 min
MS (ESIpos): m/z=246 (M+H)$^+$

Example 115A

1-[2-(Methoxymethyl)-4-nitrophenyl]piperidin-2-one

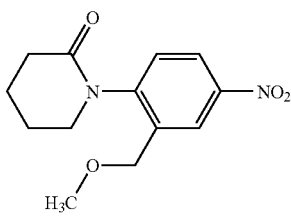

1.34 g (13.5 mmol) of piperidin-2-one are dissolved in 40 ml of anhydrous dimethyl sulfoxide and admixed with 1.82 g (16.2 mmol) of potassium tert-butoxide. After 1 h, 2.5 g (13.5 mmol) of example 27A dissolved in 10 ml of anhydrous dimethyl sulfoxide are added, and the mixture is heated to 80° C. for 3 h. The reaction solution is allowed to cool and left to stand for a further 48 h, before being diluted with ethyl acetate and washed with water and 1N hydrochloric acid. The organic phase is dried over magnesium sulfate, filtered and concentrated to dryness under reduced pressure. The residue is applied to silica gel and separated on silica gel with a 1:1 mixture of cyclohexane and ethyl acetate. The product fractions are combined and concentrated to dryness under reduced pressure. This affords 620 mg (17% of theory) of the desired compound.

¹H NMR (400 MHz, DMSO-d₆, δ/ppm): δ=8.25 (m, 2H), 7.6 (d, 1H), 4.35 (m, 2H), 4.0 (q, 2H), 4.0 (b, 2H), 3.55 (m, 2H), 3.3 (s, 3H) 2.4 (b, 2H).

Example 116A

1-[4-Amino-2-(methoxymethyl)phenyl]piperidin-2-one

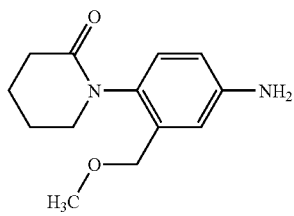

630 mg (2.38 mmol) of example 115A are dissolved in 50 ml of a 1:1 mixture of ethanol and ethyl acetate and admixed with 752 mg (11.9 mmol) of ammonium formate and 65 mg of palladium on carbon. The mixture is heated to 80° C. for 30 min. It is allowed to cool and filtered through silica gel. It is washed with ethyl acetate and ethanol, and the filtrate is concentrated to dryness under reduced pressure. This affords 560 mg (99% of theory) of the desired compound.

LC-MS (Method 6): $R_t$=1.19 min
MS (ESIpos): m/z=235 (M+H)⁺

WORKING EXAMPLES

Example 1

5-Chloro-N-({(5S)-3-[3-chloro-4-(3-methoxy-2-oxopyridin-1(2H)-yl)phenyl]-2-oxo-1,3-oxazolidin-5-yl}methyl)thiophene-2-carboxamide

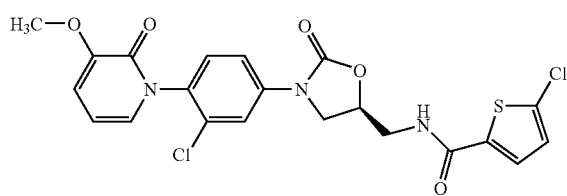

A solution of 247 mg (0.98 mmol) of the product from example 3A in 6 ml of acetonitrile is admixed with 236 mg (1.08 mmol) of the product from example 1A. To the suspension are added 330 mg (1.48 mmol) of magnesium perchlorate, after which the mixture is left to stir at RT for 17 h. Then 400 mg (2.46 mmol) of 1,1'-carbonyldiimidazole and 12 mg (0.09 mmol) of DMAP are added, and the mixture is heated to 60° C. After 4 h, it is diluted with water, saturated aqueous sodium chloride solution and ethyl acetate. The water phase is extracted twice with ethyl acetate and the combined organic phases are dried over sodium sulfate. After filtration, the mixture is freed of the solvent and the residue is prepurified by chromatography on silica gel (20:1 dichloromethane/methanol). Subsequent purification by means of preparative HPLC with an acetonitrile/water mixture affords 65 mg (13% of theory) of the desired product.

¹H NMR (400 MHz, DMSO-d₆, δ/ppm): 8.97 (t, 1H), 7.86 (dd, 1H), 7.60 (d, 1H), 7.63-7.54 (m, 1H), 7.49 (d, 1H), 7.19 (d, 1H), 7.07 (dd, 1H), 6.90 (dd, 1H), 6.25 (dd, 1H), 4.93-4.82 (m, 1H), 4.24 (dd, 1H), 3.99 (dd, 1H), 3.74 (s, 3H), 3.65-3.56 (m, 2H).

HPLC (Method 2): $R_t$=4.03 min.
MS (ESIpos, m/z): 494 (M+H)⁺.

Example 2

5-Chloro-N-({(5S)-3-[4-(3-methoxy-2-oxopyridin-1(2H)-yl)-3-methylphenyl]-2-oxo-1,3-oxazolidin-5-yl}methyl)thiophene-2-carboxamide

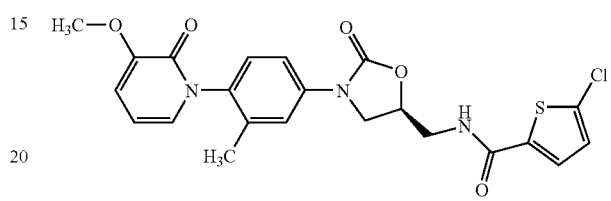

A solution of 106 mg (0.460 mmol) of the product from example 16A in 9 ml of acetonitrile is admixed with 110 mg (0.506 mmol) of the product from example 1A. To the suspension are added 154 mg (0.690 mmol) of magnesium perchlorate, after which the mixture is left to stir at RT for 18 h. Then 186 mg (1.15 mmol) of 1,1'-carbonyldiimidazole and 5 mg (0.05 mmol) of DMAP are added, and the mixture is heated to 60° C. After 4 h, it is cooled and diluted with water. The water phase is extracted three times with ethyl acetate, and the combined organic phases are washed with saturated aqueous sodium chloride solution and dried over sodium sulfate. After filtration, the mixture is freed of the solvent and the residue is purified by chromatography on silica gel (20:1 dichloromethane/ethanol). After removing the solvent, 150 mg (68% of theory) of the desired product are obtained.

¹H NMR (400 MHz, DMSO-d₆, δ/ppm): 8.97 (t, 1H), 7.69 (d, 1H), 7.57-7.45 (m, 2H), 7.28-7.13 (m, 2H), 7.03 (d, 1H), 6.90 (d, 1H), 6.24 (dd, 1H), 4.93-4.80 (m, 1H), 4.22 (dd, 1H), 3.92-3.85 (m, 1H), 3.74 (s, 3H), 3.62 (dd, 2H), 2.00 (s, 3H).

HPLC (Method 2): $R_t$=4.04 min.

Example 3

5-Chloro-N-({(5S)-3-[4-(3-methoxy-2-oxopyridin-1(2H)-yl)-3,5-dimethylphenyl]-2-oxo-1,3-oxazolidin-5-yl}methyl)thiophene-2-carboxamide

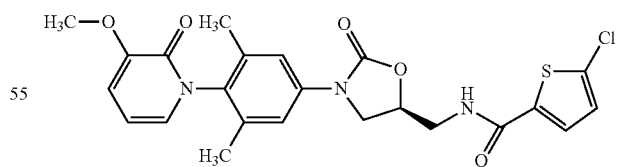

A solution of 195 mg (0.799 mmol) of the product from example 18A in 10 ml of acetonitrile is admixed with 191 mg (0.878 mmol) of the product from example 1A. To the suspension are added 267 mg (1.197 mmol) of magnesium perchlorate, after which the mixture is left to stir at RT for 5 h. Then 259 mg (1.59 mmol) of 1,1'-carbonyldiimidazole and 9 mg (0.08 mmol) of DMAP are added, and the mixture is heated to 60° C. After 24 h, the mixture is cooled and diluted with 50 ml of water. The water phase is extracted three times with ethyl acetate and the combined organic phases are dried over sodium sulfate. After filtration, the mixture is freed of the solvent and the residue is purified by chromatography on silica gel (20:1 dichloromethane/ethanol). After removing the solvents, 258 mg (65% of theory) of the desired product are obtained.

$^1$H NMR 300 MHz, DMSO-$d_6$, δ/ppm): 8.98 (t, 1H), 7.69 (d, 1H), 7.42-7.32 (m, 2H), 7.20 (dd, 1H), 7.00-6.88 (m, 2H), 6.28 (dd, 1H), 4.91-4.80 (m, 1H), 4.20 (dd, 1H), 3.90-3.82 (m, 1H), 3.75 (s, 3H), 3.60 (dd, 2H), 1.95 (s, 6H).

HPLC (Method 2): $R_t$=4.05 min.

MS (ESIpos, m/z): 494 (M+H)$^+$.

Example 4

5-Chloro-N-({(5S)-3-[4-(3-ethoxy-2-oxopyridin-1(2H)-yl]-3-methylphenyl]-2-oxo-1,3-oxazolidin-5-yl}methyl)thiophene-2-carboxamide

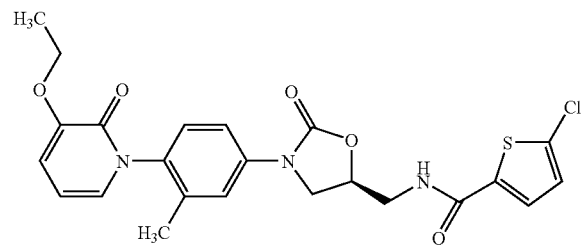

250 mg (0.544 mmol) of example 15A are dissolved in 2.5 ml of anhydrous N,N-dimethylformamide, admixed with 150 mg (1.1 mmol) of potassium carbonate and stirred for a further 30 min. 128 mg (0.872 mmol) of iodoethane are added and the mixture is heated to 60° C. for 5 h. Then it is diluted with 1 ml of dimethyl sulfoxide, filtered and purified by preparative HPLC with a water/acetonitrile gradient. The product fractions are concentrated to dryness under reduced pressure and the residue is dried under reduced pressure. After removing the solvents, 104 mg (39% of theory) of the desired product are obtained.

$^1$H NMR (400 MHz, DMSO-$d_6$, δ/ppm): δ=8.95 (t, 1H), 7.70 (d, 1H), 7.55-7.46 (m, 2H), 7.25-7.17 (m, 2H), 7.03 (d, 1H), 6.88 (d, 1H), 6.22 (t, 1H), 4.90-4.82 (m, 1H), 4.22 (t, 1H), 4.02-3.92 (m, 2H), 3.91-3.84 (m, 1H), 3.61 (t, 2H), 2.01 (s, 3H), 1.35 (t, 3H).

LC-MS (Method 4): $R_t$=2.20 min

MS (ESIpos): m/z=488 (M+H)$^+$

Analogously to the preparation of example 4, the corresponding alkyl halide and example 15A are used to prepare the following derivatives.

Example 5

N-[((5S)-3-{4-[3-(2-Amino-2-oxoethoxy)-2-oxopyridin-1(2H)-yl]-3-methylphenyl}-2-oxo-1,3-oxazolidin-5-yl)methyl]-5-chlorothiophene-2-carboxamide

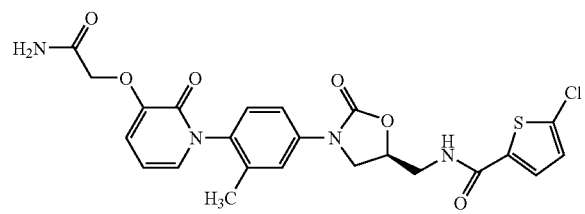

Yield: 41.1 mg (53% of theory)

$^1$H NMR (400 MHz, DMSO-$d_6$, δ/ppm): δ=8.99 (t, 1H), 7.70 (d, 1H), 7.56-7.49 (m, 2H), 7.48-7.39 (m, 2H), 7.24 (d, 1H), 7.20 (d, 1H), 7.14 (d, 1H), 6.97 (d, 1H), 6.26 (t, 1H), 4.90-4.82 (m, 1H), 4.45 (s, 2H), 4.22 (t, 1H), 3.91-3.85 (m, 1H), 3.61 (t, 2H), 2.03 (s, 3H).

LC-MS (Method 4): $R_t$=1.88 min

MS (ESIpos): m/z=517 (M+H)$^+$

Example 6

5-Chloro-N-[((5S)-3-{4-[3-(2-methoxyethoxy)-2-oxopyridin-1(2H)-yl]-3-methylphenyl}-2-oxo-1,3-oxazolidin-5-yl)methyl]thiophene-2-carboxamide

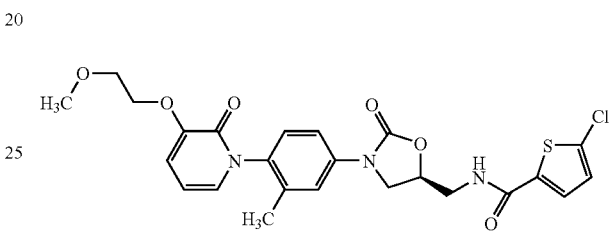

Yield: 39.1 mg (50% of theory)

$^1$H NMR (400 MHz, DMSO-$d_6$, δ/ppm): δ=8.99 (t, 1H), 7.70 (d, 1H), 7.55-7.47 (m, 2H), 7.26-7.18 (m, 2H), 7.05 (d, 1H), 6.93 (d, 1H), 6.22 (t, 1H), 4.90-4.82 (m, 1H), 4.22 (t, 1H), 4.10-3.99 (m, 2H), 3.91-3.81 (m, 1H), 3.66 (t, 2H), 3.61 (t, 2H), 2.54 (s, 3H), 2.02 (s, 3H).

LC-MS (Method 4): $R_t$=2.09 min

MS (ESIpos): m/z=518 (M+H)$^+$

Example 7

5-Chloro-N-[((5S)-3-{3-methyl-4-[2-oxo-3-(2-oxopropoxy)pyridin-1(2H)-yl]phenyl}-2-oxo-1,3-oxazolidin-5-yl)methyl]thiophene-2-carboxamide

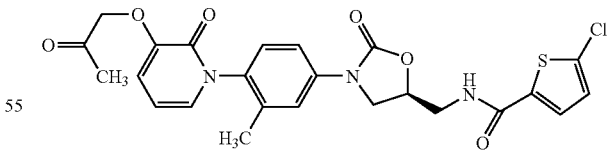

Yield: 24.8 mg (32% of theory)

$^1$H NMR (400 MHz, DMSO-$d_6$, δ/ppm): δ=8.98 (t, 1H), 7.70 (d, 1H), 7.55-7.49 (m, 2H), 7.25 (d, 1H), 7.20 (d, 1H), 7.11-7.07 (m, 1H), 6.85 (dd, 1H), 6.20 (t, 1H), 4.90-4.82 (m, 1H), 4.77 (s, 2H), 4.22 (t, 1H), 3.91-3.85 (m, 1H), 3.62 (t, 2H), 2.15 (s, 3H), 2.02 (d, 3H).

LC-MS (Method 4): $R_t$=2.04 min

MS (ESIpos): m/z=516 (M+H)$^+$

Example 8

5-Chloro-N-[((5S)-3-{4-[3-(2-fluoroethoxy)-2-oxopyridin-1(2H)-yl]-3-methylphenyl}-2-oxo-1,3-oxazolidin-5-yl)methyl]thiophene-2-carboxamide

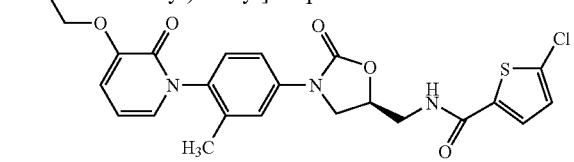

Yield: 52.9 mg (52% of theory)

$^1$H NMR (400 MHz, DMSO-d$_6$, δ/ppm): δ=9.0 (t, 1H), 7.7 (d, 1H), 7.50 (m, 2H), 7.2 (m, 2H), 7.1 (m, 1H), 7.0 (m, 1H), 6.2 (t, 1H), 4.85 (m, 1H), 4.8 (m, 1H), 4.7 (m, 1H), 4.2 (m, 3H), 3.9 (m, 1H), 3.6 (t, 2H), 2.0 (s, 3H).

LC-MS (Method 4): R$_t$=2.23 min

MS (ESIpos): m/z=506 (M+H)$^+$

Example 9

5-Chloro-N-[((5S)-3-{4-[3-(2-hydroxy-2-methylpropoxy)-2-oxopyridin-1(2H)-yl]-3-methylphenyl}-2-oxo-1,3-oxazolidin-5-yl)methyl]thiophene-2-carboxamide

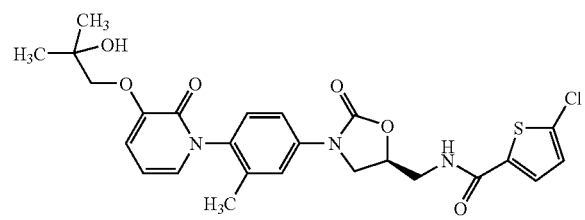

Yield: 17.5 mg (11% of theory)

$^1$H NMR (400 MHz, DMSO-d$_6$, δ/ppm): δ=8.98 (t, 1H), 7.70 (d, 1H), 7.56-7.47 (m, 2H), 7.26-7.17 (m, 2H), 7.05 (d, 1H), 6.93 (d, 1H), 6.21 (t, 1H), 4.91-4.82 (m, 1H), 4.64 (s, 1H), 4.22 (t, 1H), 3.92-3.84 (m, 1H), 3.77-3.55 (m, 3H), 2.02 (s, 3H), 1.22-1.16 (m, 6H).

LC-MS (Method 5): R$_t$=2.05 min

MS (ESIpos): m/z=532 (M+H)$^+$

Example 10

5-Chloro-N-[((5S)-3-{3-methyl-4-[3-(2-morpholin-4-yl-2-oxoethoxy)-2-oxopyridin-1(2H)-yl]phenyl}-2-oxo-1,3-oxazolidin-5-yl)methyl]thiophene-2-carboxamide

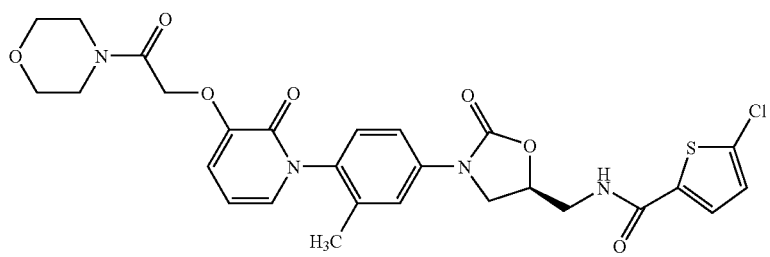

Yield: 50.6 mg (43% of theory)

$^1$H NMR (400 MHz, DMSO-d$_6$, δ/ppm): δ=8.98 (t, 1H), 7.70 (d, 1H), 7.55-7.49 (m, 2H), 7.26-7.18 (m, 2H), 7.13-7.07 (m, 1H), 6.88 (dd, 1H), 6.22 (t, 1H), 4.90-4.80 (m, 3H), 4.22 (t, 1H), 3.9-3.84 (m, 1H), 3.64-3.38 (m, 10H), 2.02 (s, 3H).

LC-MS (Method 5): R$_t$=1.90 min

MS (ESIpos): m/z=586 (M+H)$^+$

Example 11

5-Chloro-N-[((5S)-3-{3-methyl-4-[3-[2-(methylamino)-2-oxoethoxy]-2-oxopyridin-1(2H)-yl]phenyl}-2-oxo-1,3-oxazolidin-5-yl)methyl]thiophene-2-carboxamide

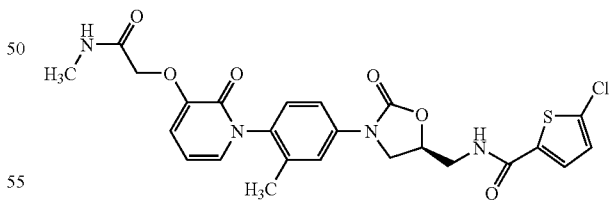

Yield: 43.4 mg (41% of theory)

$^1$H NMR (400 MHz, DMSO-d$_6$, δ/ppm): δ=8.98 (t, 1H), 8.02-7.95 (m, 1H), 7.69 (d, 1H), 7.56-4.49 (b, 2H), 7.25 (d, 1H), 7.20 (d, 1H), 7.14 (d, 1H), 6.93 (d, 1H), 6.25 (t, 1H), 4.90-4.82 (m, 1H), 4.47 (s, 2H), 4.22 (t, 1H), 3.92-3.85 (m, 1H), 3.62 (t, 2H), 2.65 (s, 3H), 2.02 (s, 3H).

LC-MS (Method 5): R$_t$=1.87 min

MS (ESIpos): m/z=531 (M+H)$^+$

Example 12

N-[((5S)-3-{4-[3-[2-(tert-Butylamino)-2-oxoethoxy]-2-oxopyridin-1(2H)-yl]-3-methylphenyl}-2-oxo-1,3-oxazolidin-5-yl)methyl]-5-chlorothiophene-2-carboxamide

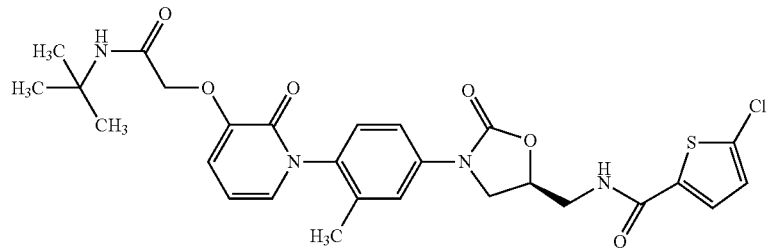

Yield: 40.9 mg (40% of theory)

¹H NMR (400 MHz, DMSO-d₆, δ/ppm): δ=8.98 (t, 1H), 8.00 (d, 1H), 7.70 (d, 1H), 7.61-7.50 (m, 2H), 7.25 (d, 1H), 7.20 (d, 1H), 7.15 (dd, 1H), 7.02 (dd, 1H), 6.26 (t, 1H), 4.90-4.82 (m, 1H), 4.41 (s, 2H), 4.22 (t, 1H), 3.91-3.85 (m, 1H), 3.61 (t, 2H), 2.02 (s, 3H), 1.27 (s, 9H).

LC-MS (Method 5): $R_t$=2.17 min

MS (ESIpos): m/z=573 (M+H)⁺

Example 13

5-Chloro-N-[((5S)-3-{3-methyl-4-[2-oxo-3-(2,2,2-trifluoroethoxy)pyridin-1(2H)-yl]phenyl}-2-oxo-1,3-oxazolidin-5-yl)methyl]thiophene-2-carboxamide

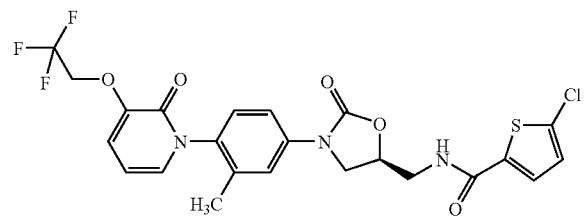

Yield: 11.9 mg (11% of theory)

¹H NMR (400 MHz, CDCl₃, δ/ppm): δ=7.51-7.45 (m, 2H), 7.33 (d, 1H), 7.21-7.18 (m, 1H), 7.12 (dd, 1H), 7.00 (dd, 1H), 6.90 (d, 1H), 6.70-6.62 (d, 1H), 6.22 (t, 1H), 4.88-4.78 (m, 1H), 4.66-4.50 (m, 2H), 4.16-4.04 (m, 1H), 3.90-3.82 (m, 2H), 3.76-3.66 (m, 1H), 2.13 (s, 3H).

LC-MS (Method 3): $R_t$=2.13 min

MS (ESIpos): m/z=542 (M+H)⁺

Example 14

5-Chloro-N-[((5S)-3-{4-[3-[2-(dimethylamino)-2-oxoethoxy]-2-oxopyridin-1(2H)-yl]-3-methylphenyl}-2-oxo-1,3-oxazolidin-5-yl)methyl]thiophene-2-carboxamide

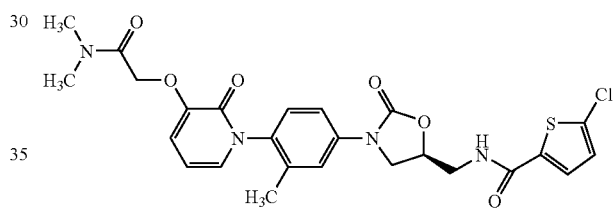

Yield: 51.7 mg (47% of theory)

¹H NMR (400 MHz, DMSO-d₆, δ/ppm): δ=8.98 (t, 1H), 7.70 (d, 1H), 7.56-7.47 (m, 2H), 7.25 (d, 1H), 7.20 (d, 1H), 7.09 (d, 1H), 6.83 (d, 1H), 6.21 (t, 1H), 4.90-4.82 (m, 1H), 4.78 (s, 2H), 4.22 (t, 1H), 3.92-3.84 (m, 1H), 3.62 (t, 2H), 3.00 (s, 3H), 2.85 (s, 3H), 2.02 (s, 3H).

LC-MS (Method 3): $R_t$=1.71 min

MS (ESIpos): m/z=545 (M+H)⁺

Example 15

5-Chloro-N-[((5S)-3-{4-[3-(2-hydroxyethoxy)-2-oxopyridin-1(2H)-yl]-3-methylphenyl}-2-oxo-1,3-oxazolidin-5-yl)methyl]thiophene-2-carboxamide

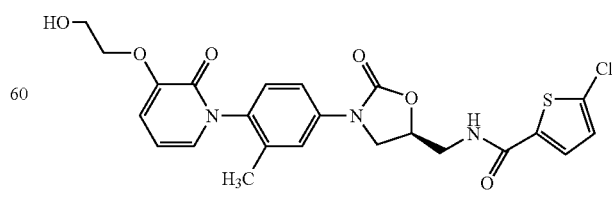

2.0 g (4.35 mmol) of example 15A are dissolved in 9 ml of anhydrous N,N-dimethylformamide, admixed with 3.6 g (26.1 mmol) of potassium carbonate and stirred for a further 30 min. The mixture is diluted with a further 3 ml of anhydrous N,N-dimethylformamide, admixed with 3.1 g (13.05 mmol) of (2-bromoethoxy)(tert-butyl)dimethylsilane and heated to 60° C. for 7 h. The mixture is allowed to cool, filtered and purified by preparative HPLC with a water/acetonitrile gradient. The product fractions are concentrated to dryness under reduced pressure and the residue is dried under reduced pressure. This affords 1.17 g (53% of theory) of the desired compound.

$^1$H NMR (400 MHz, DMSO-$d_6$, δ/ppm): δ=8.98 (t, 1H), 7.70 (d, 1H), 7.56-7.47 (m, 2H), 7.25-7.17 (m, 2H), 7.05 (dd, 1H), 6.93 (dd, 1H), 6.22 (t, 1H), 4.91 (t, 1H), 4.87-4.82 (m, 1H), 4.22 (t, 1H), 4.00-3.84 (m, 3H), 3.75-3.68 (m, 2H), 3.61 (t, 2H), 2.02 (s, 3H).

LC-MS (Method 5): $R_t$=1.93 min
MS (ESIpos): m/z=504 (M+H)$^+$

Example 16

5-Chloro-N-{[(5S)-3-{4-[3-(2-hydroxyethoxy)-2-oxopyridin-1(2H)-yl]-3,5-dimethylphenyl}-2-oxo-1,3-oxazolidin-5-yl]methyl}thiophene-2-carboxamide

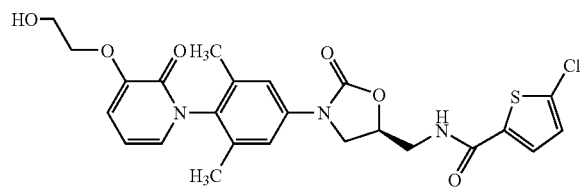

A solution of 108 mg (0.228 mmol) of the product from example 23A in 2 ml of DMF is admixed with 189 mg (1.37 mmol) of potassium carbonate. After 1 h at RT, 0.15 ml (0.684 mmol) of (2-bromoethoxy)-tert-butyldimethylsilane is added dropwise and the mixture is stirred at 60° C. After 2 h, it is cooled and added to 50 ml of water. After phase separation, it is extracted three times with 80 ml of ethyl acetate. The combined organic phases are washed with saturated aqueous sodium chloride solution and then dried over sodium sulfate. After filtration, the mixture is freed of the solvent, and the residue is taken up in 6 ml of dichloromethane and admixed at RT with 2 ml of trifluoroacetic acid. After 2 h at RT, the mixture is diluted with 50 ml of dichloromethane, and washed twice with water, then with saturated aqueous sodium hydrogencarbonate solution and then with water again. It is dried over sodium sulfate and then freed of the solvent. Since reactant is still present, the residue is dissolved once again in 4 ml of dichloromethane and admixed with 1 ml of trifluoroacetic acid. After 3.5 h at RT, the mixture is diluted with 50 ml of dichloromethane and washed with saturated aqueous sodium hydrogencarbonate solution and with water. Then it is dried over sodium sulfate and then freed of the solvent. The residue is purified by chromatography on silica gel (20:1 dichloromethane/ethyl acetate). This affords 83 mg (70% of theory) of the desired product.

$^1$H NMR (400 MHz, DMSO-$d_6$, δ/ppm): 8.98 (t, 1H), 7.70 (d, 1H), 7.38 (dd, 2H), 7.20 (d, 1H), 6.99-6.90 (m, 2H), 6.26 (dd, 1H), 4.97-4.80 (m, 2H), 4.22 (dd, 1H), 3.95 (dd, 2H), 3.86 (m, 1H), 3.76-3.70 (m, 2H), 3.60 (dd, 2H), 1.96 (s, 6H).

HPLC (Method 1): $R_t$=3.93 min.
MS (DCI, m/z): 518 (M+H)$^+$.

Example 17

5-Chloro-N-[((5S)-3-{4-[3-(difluoromethoxy)-2-oxopyridin-1(2H)-yl]-3-methylphenyl}-2-oxo-1,3-oxazolidin-5-yl)methyl]thiophene-2-carboxamide

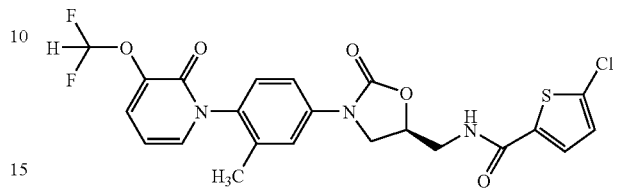

100 mg (0.172 mmol) of example 15A are dissolved in 1.5 ml of anhydrous N,N-dimethylformamide, admixed with 121 mg (0.87 mmol) of potassium carbonate and stirred for 30 min. 68.9 mg (0.435 mmol) of ethyl chloro(difluoro)acetate are added and the mixture is heated to 60° C. for 6 h. Then it is filtered and purified by preparative HPLC with a water/acetonitrile gradient. The product fractions are concentrated to dryness under reduced pressure and the residue is dried under reduced pressure. This affords 21 mg (19% of theory) of the desired compound.

$^1$H NMR (400 MHz, DMSO-$d_6$, δ/ppm): δ=9.0 (t, 1H), 7.6 (d, 1H), 7.05 (b, 2H), 7.5 (d, 2H), 7.3 (d, 1H), 7.2 (d, 1H), 7.05 (t, 1H), 6.3 (t, 1H), 4.85 (m, 1H), 4.2 (t, 1H), 3.9 (m, 1H), 3.6 (t, 2H), 2.0 (s, 3H).

LC-MS (Method 4): $R_t$=2.04 min
MS (ESIpos): m/z=510 (M+H)$^+$

Example 18

5-Chloro-N-({(5S)-3-[4-(3-ethoxy-2-oxopyrazin-1(2H)-yl)-3-methylphenyl]-2-oxo-1,3-oxazolidin-5-yl}methyl)thiophene-2-carboxamide

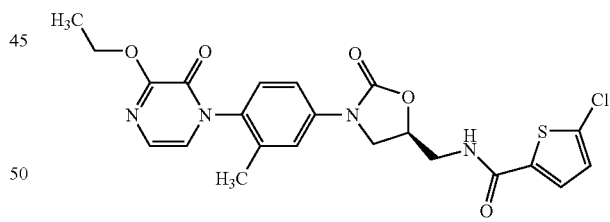

400 mg (1.63 mmol) of example 114A are dissolved in 16 ml of anhydrous acetonitrile and admixed at 0° C. with 443 mg (1.71 mmol) of example 1A. The mixture is admixed with 546 mg (2.45 mmol) of magnesium perchlorate, the cooling is removed and the mixture is stirred at RT for 5 h. Then 528 mg (3.26 mmol) of 1,1-carbonyldiimidazole and 4 mg (0.03 mmol) of N,N-dimethylaminopyridine are added, and the mixture is heated at reflux for 15 h. It is allowed to cool and the solvent is distilled off under reduced pressure. The residue is taken up in ethyl acetate and washed twice with water, with saturated sodium hydrogencarbonate solution and with saturated sodium chloride solution, and dried over magnesium sulfate. After filtration, it is concentrated to dryness under reduced pressure. The residue is partly dissolved in acetonitrile and it is purified by preparative HPLC with a gradient of water and acetonitrile. The product fractions are combined and concentrated to dryness under reduced pressure. This affords 273 mg (34% of theory) of the desired compound.

$^1$H NMR (400 MHz, DMSO-$d_6$, δ/ppm): δ=8.98 (t, 1H), 7.70 (d, 1H), 7.56-7.50 (m, 2H), 7.30 (d, 1H), 7.20 (d, 1H), 7.07 (d, 1H), 6.88 (d, 1H), 4.90-4.82 (m, 1H), 4.30 (q, 2H), 4.21 (t, 1H), 3.90-3.84 (m, 1H), 3.61 (t, 2H), 2.05 (s, 3H), 1.34 (t, 3H).

LC-MS (Method 6): $R_t$=2.22 min
MS (ESIpos): m/z=489 (M+H)$^+$

Example 19

5-Chloro-N-({(5S)-3-[3-(ethoxymethyl)-4-(2-oxopyridin-1(2H)-yl)phenyl]-2-oxo-1,3-oxazolidin-5-yl}methyl)thiophene-2-carboxamide

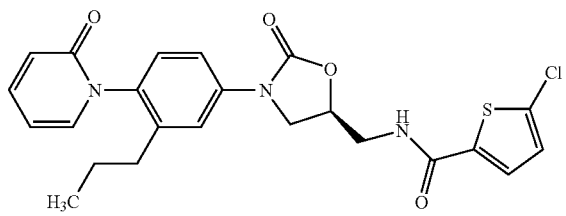

90 mg (0.39 mmol) of example 38A are dissolved in 6 ml of anhydrous acetonitrile and admixed at 0° C. with 122 mg (0.47 mmol) of example 1A. 131 mg (0.59 mmol) of magnesium perchlorate are added, the cooling is removed and the mixture is stirred at RT for 15 h. The solvent is concentrated under reduced pressure and the residue is diluted with 9 ml of butyronitrile. Then it is admixed with 127 mg (0.79 mmol) of 1,1-carbonyldiimidazole and 1 mg (0.01 mmol) of N,N-dimethylaminopyridine, and heated at reflux for 15 h. It is allowed to cool and the solvent is distilled off under reduced pressure, and the residue is partly dissolved in acetonitrile and purified by preparative HPLC with a gradient of water and acetonitrile. The product fractions are combined and concentrated to dryness under reduced pressure. This affords 33 mg (18% of theory) of the desired compound.

$^1$H NMR (400 MHz, DMSO-$d_6$, δ/ppm): δ=8.98 (t, 1H), 7.70 (d, 1H), 7.56-7.46 (m, 4H), 7.24-7.17 (m, 2H), 6.47 (d, 1H), 6.30 (dt, 1H), 4.90-4.82 (m, 1H), 4.26-4.19 (m, 1H), 3.92-3.85 (m, 1H), 3.62 (t, 2H), 2.30 (t, 2H), 1.49-1.36 (m, 2H), 0.71 (t, 3H).

LC-MS (Method 6): $R_t$=2.20 min
MS (ESIpos): m/z=472 (M+H)$^+$

Example 20

5-Chloro-N-[((5S)-3-{3-methyl-4-[2-oxo-3-(trifluoromethyl)pyridin-1(2H)-yl]phenyl}-2-oxo-1,3-oxazolidin-5-yl)methyl]thiophene-2-carboxamide

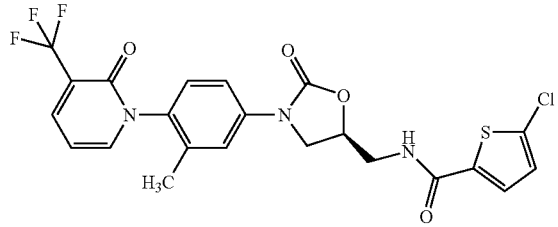

750 mg (2.8 mmol) of example 40A are dissolved in 28 ml of anhydrous acetonitrile and admixed at 0° C. with 730 mg (3.36 mmol) of example 1A. 936 mg (4.19 mmol) of magnesium perchlorate are added, the cooling is removed and the mixture is stirred at RT for 15 h. The solvent is concentrated under reduced pressure and the residue is diluted with 55 ml of butyronitrile. Then the mixture is admixed with 906 mg (5.59 mmol) of 1,1-carbonyldiimidazole and 7 mg (0.06 mmol) of N,N-dimethylaminopyridine, and heated at reflux for 15 h. It is allowed to cool, the solvent is distilled off under reduced pressure, and the residue is partly dissolved in acetonitrile and purified by preparative HPLC with a gradient of water and acetonitrile. The product fractions are combined and concentrated to dryness under reduced pressure. This affords 828 mg (58% of theory) of the desired compound.

$^1$H NMR (400 MHz, DMSO-$d_6$, δ/ppm): δ=8.98 (t, 1H), 8.07 (d, 1H), 7.89 (d, 1H), 7.70 (d, 1H), 7.58-7.52 (m, 2H), 7.33 (d, 1H), 7.20 (d, 1H), 6.47 (t, 1H), 4.91-4.82 (m, 1H), 4.23 (t, 1H), 3.92-3.85 (m, 1H), 3.62 (t, 2H), 2.04 (s, 3H).

LC-MS (Method 6): $R_t$=2.14 min
MS (ESIpos): m/z=512 (M+H)$^+$

Example 21

5-Chloro-N-[((5S)-3-{5-methyl-4-(3-methyl-2-oxopyridin-1(2H)-yl)-2-[methyl(propyl)amino]-phenyl}-2-oxo-1,3-oxazolidin-5-yl)methyl]thiophene-2-carboxamide

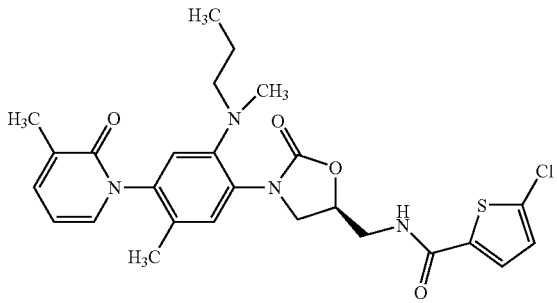

A solution of 180 mg (0.631 mmol) of the product from example 105A in 5 ml of acetonitrile is admixed with 151 mg (0.694 mmol) of the product from example 1A. To the suspension are added 211 mg (0.95 mmol) of magnesium perchlorate, after which the mixture is left to stir at RT for 17 h. Then 256 mg (1.58 mmol) of 1,1'-carbonyldiimidazole and 7.7 mg (0.06 mmol) of DMAP are added and the mixture is stirred at 60° C. for 17 h. The crude mixture is purified by means of preparative HPLC with an acetonitrile/water mixture. This affords 106 mg (30% of theory) of the desired product.

$^1$H NMR (400 MHz, DMSO-$d_6$, δ/ppm): 9.04 (t, 1H), 7.77 (d, 1H), 7.44-7.34 (m, 2H), 7.22 (d, 1H), 7.14 (d, 1H), 6.88 (s, 1H), 6.22 (dd, 1H), 4.95-4.82 (m, 1H), 4.00 (ddd, 1H), 3.72-3.50 (m, 3H), 2.90-2.69 (m, 2H), 2.58 (s, 3H), 2.04 (s, 3H), 1.86 (d, 3H), 1.46-1.31 (m, 2H), 0.80 (s, 3H).

HPLC (Method 2): $R_t$=4.07 min.
MS (DCI, m/z): 529 (M+H)$^+$.

Example 22

5-Chloro-N-({(5S)-3-[5-methyl-4-(3-methyl-2-oxopyridin-1(2H)-yl)-2-propoxyphenyl]-2-oxo-1,3-oxazolidin-5-yl}methyl)thiophene-2-carboxamide

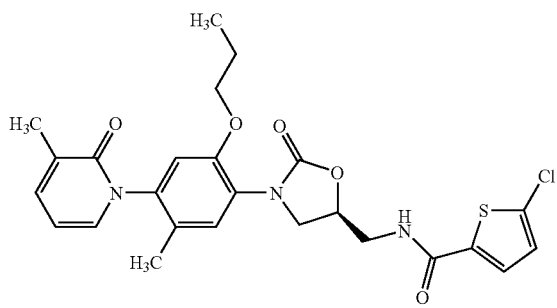

A solution of 415 mg (1.52 mmol) of the product from example 109A in 10 ml of acetonitrile is admixed with 365 mg (1.68 mmol) of the product from example 1A. To the suspension are added 510 mg (2.29 mmol) of magnesium perchlorate, after which the mixture is left to stir at RT for 17 h. Then 617 mg (3.81 mmol) of 1,1'-carbonyldiimidazole and 18 mg (0.15 mmol) of DMAP are added, and the mixture is heated to 60° C. After 48 h, the mixture is freed of the solvent and the concentrated filtrate is purified by means of preparative HPLC with an acetonitrile/water mixture. This affords 58 mg (7% of theory) of the desired product.

$^1$H NMR (400 MHz, DMSO-$d_6$, δ/ppm): 8.99 (t, 1H), 7.74 (d, 1H), 7.44-7.33 (m, 2H), 7.22 (br.s, 2H), 6.99 (s, 1H), 6.24 (dd, 1H), 4.88-4.80 (m, 1H), 4.07-3.88 (m, 3H), 3.76-3.53 (m, 3H), 2.04 (s, 3H), 1.89 (s, 3H), 1.70-1.61 (m, 2H), 0.92 (t, 3H).

HPLC (Method 2): $R_t$=4.43 min.

Example 23

5-Chloro-N-({(5S)-3-[4-(1-ethyl-2-oxo-1,2-dihydropyridin-3-yl)-3-methoxyphenyl]-2-oxo-1,3-oxazolidin-5-yl}methyl)thiophene-2-carboxamide

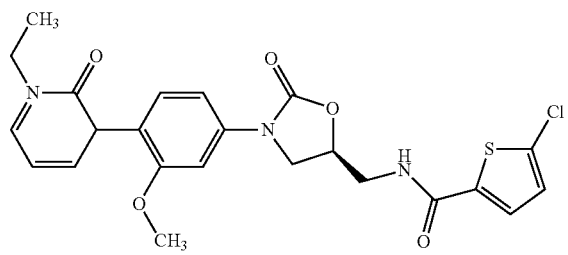

160 mg (0.67 mmol) of the compound from example 57A are dissolved in 6 ml of acetonitrile. The mixture is cooled to 0° C., and admixed with 157 mg (0.72 mmol) of the compound from example 1A and 219 mg (0.98 mmol) of magnesium perchlorate, after which the mixture is stirred at RT for 20 h. Then 159 mg (0.98 mmol) of 1,1'-carbonyldiimidazole and 8 mg (0.065 mmol) of DMAP are added, and the mixture is heated to 60° C. for 20 h. Purification is effected directly by means of preparative HPLC. This affords 190 mg (59% of theory) of the desired product.

$^1$H NMR (400 MHz, DMSO-$d_6$, δ/ppm): 8.99 (t, 1H), 7.70 (d, 1H), 7.68 (dd, 1H), 7.36-7.32 (m, 2H), 7.25 (d, 1H), 7.20 (d, 1H), 7.01 (dd, 1H), 6.26 (t, 1H), 4.89-4.81 (m, 1H), 4.22 (t, 1H), 3.94 (q, 2H), 3.88 (dd, 1H), 3.70 (s, 3H), 3.62 (t, 2H), 1.23 (t, 3H).

HPLC (Method 3): $R_t$=1.89 min.

MS (ESIpos, m/z): 488/490 ($^{35}$Cl/$^{37}$Cl) (M+H)$^+$.

Example 24

5-Chloro-N-({(5S)-3-[3-methoxy-4-(1-methyl-2-oxo-1,2-dihydropyridin-3-yl)phenyl]-2-oxo-1,3-oxazolidin-5-yl}methyl)thiophene-2-carboxamide

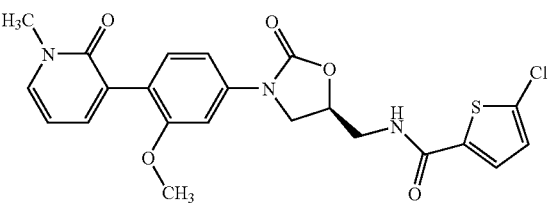

260 mg (1.13 mmol) of the product from example 59A are reacted analogously to example 23 with the product from example 1A. Purification is effected by means of preparative HPLC. This affords 310 mg (58% of theory) of the desired product.

$^1$H NMR (400 MHz, DMSO-$d_6$, δ/ppm): 8.98 (t, 1H), 7.70 (d, 1H), 7.67 (dd, 1H), 7.36-7.33 (m, 2H), 7.23 (d, 1H), 7.20 (d, 1H), 7.01 (dd, 1H), 6.24 (t, 1H), 4.89-4.81 (m, 1H), 4.23 (t, 1H), 3.88 (dd, 1H), 3.70 (s, 3H), 3.62 (t, 2H), 3.46 (s, 3H).

HPLC (Method 2): $R_t$=3.99 min.

MS (ESIpos, m/z): 474/476 ($^{35}$Cl/$^{37}$Cl) (M+H)$^+$.

Example 25

5-Chloro-N-({(5S)-3-[3-methoxy-4-(2-oxo-1-propyl-1,2-dihydropyridin-3-yl)phenyl]-2-oxo-1,3-oxazolidin-5-yl}methyl)thiophene-2-carboxamide

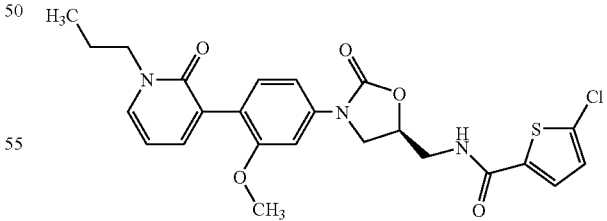

110 mg (0.43 mmol) of the product from example 53A are reacted analogously to example 23 with the product from example 1A. Purification is effected by means of preparative HPLC. This affords 113 mg (51% of theory) of the desired product.

$^1$H NMR (400 MHz, DMSO-$d_6$, δ/ppm): 9.00 (t, 1H), 7.70 (d, 1H), 7.44 (d, 1H), 7.32-7.28 (m, 2H), 7.26 (d, 1H), 7.20 (d, 1H), 7.11 (d, 1H), 6.19 (t, 1H), 4.91-4.83 (m, 1H), 4.25 (t, 1H), 3.90 (dd, 1H), 3.73 (s, 3H), 3.63 (t, 2H), 2.52-2.49 (m, 2H), 1.50-1.48 (m, 2H), 0.91 (t, 3H).
HPLC (Method 4): $R_t$=2.43 min.
MS (ESIpos, m/z): 502/504 ($^{35}$Cl/$^{37}$Cl) (M+H)$^+$.

Example 26

5-Chloro-N-({(5S)-3-[3-ethoxy-4-(2-oxopiperidin-1-yl)phenyl]-2-oxo-1,3-oxazolidin-5-yl}methylythiophene-2-carboxamide

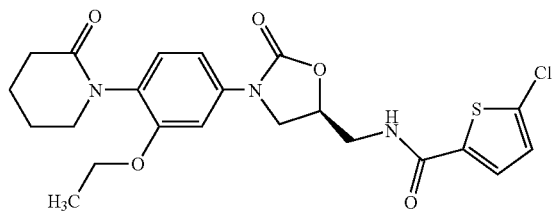

A solution of 220 mg (0.939 mmol) of the product from example 91A in 10 ml of acetonitrile is admixed with 224 mg (1.03 mmol) of the product from example 1A. To the suspension are added 314 mg (1.41 mmol) of magnesium perchlorate, after which the mixture is left to stir at RT for 5 h. Then 380 mg (2.35 mmol) of 1,1'-carbonyldiimidazole and 11 mg (0.09 mmol) of DMAP are added, and the mixture is stirred at RT. After 18 h, it is diluted with 100 ml of water. The water phase is extracted three times with ethyl acetate and the combined organic phases are dried over sodium sulfate. Subsequent purification by means of preparative HPLC with a gradient of water and acetonitrile affords 137 mg (30% of theory) of the desired product.
$^1$H NMR (400 MHz, DMSO-d$_6$, δ/ppm): 8.97 (t, 1H), 7.69 (d, 1H), 7.32 (d, 1H), 7.20 (d, 1H), 7.11 (d, 1H), 6.98 (dd, 1H), 4.90-4.78 (m, 1H), 4.19 (dd, 1H), 3.99 (q, 2H), 3.85 (dd, 1H), 3.60 (dd, 2H), 3.44-3.35 (m, 2H), 2.37-2.28 (m, 2H), 1.88-1.77 (m, 4H), 1.30 (t, 3H).
LC-MS (Method 5): $R_t$=4.03 min.
MS (ESIpos, m/z): 478 (M+H)$^+$.

Example 27

5-Chloro-N-({(5S)-3-[3-(methoxymethyl)-4-(2-oxopiperidin-1-yl)phenyl]-2-oxo-1,3-oxazolidin-5-yl}methyl)thiophene-2-carboxamide

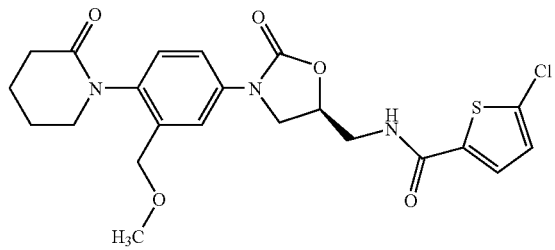

560 mg (2.39 mmol) of example 116A are dissolved in 24 ml of anhydrous acetonitrile and admixed at 0° C. with 624 mg (2.87 mmol) of example 1A. 800 mg (3.89 mmol) of magnesium perchlorate are added, the cooling is removed and the mixture is stirred at RT for 15 h. The solvent is removed under reduced pressure, and the residue is dissolved with 50 ml of anhydrous butyronitrile and then admixed with 775 mg (4.78 mmol) of 1,1-carbonyldiimidazole and 6 mg (0.05 mmol) of N,N-dimethylaminopyridine. After heating at reflux for 16 h, the mixture is admixed with ethyl acetate, and the organic phase is removed, washed twice with water, once with saturated sodium hyrodencarbonate solution and once with saturated sodium chloride solution, dried, filtered and concentrated to dryness under reduced pressure. The residue is partly dissolved in dimethyl sulfoxide and purified by preparative HPLC with a gradient of water and acetonitrile. The product fractions are combined and concentrated to dryness under reduced pressure. This affords 560 mg (49% of theory) of the desired compound.
$^1$H NMR (400 MHz, DMSO-d$_6$, δ/ppm): δ=8.97 (t, 1H), 7.70 (d, 1H), 7.59-7.54 (m, 1H), 7.52-7.45 (m, 1H), 7.24-7.17 (m, 2H), 4.87-4.78 (m, 1H), 4.30 (d, 1H), 4.22-4.14 (m, 2H), 3.90-3.83 (m, 1H), 3.63-3.52 (m, 3H), 3.37-3.27 (m, 4H), 2.40-2.32 (m, 2H), 1.90-1.80 (m, 4H).
LC-MS (Method 5): $R_t$=1.93 min
MS (ESIpos): m/z=478 (M+H)$^+$ Example 28

5-Chloro-N-({(5S)-3-[3-(ethoxymethyl)-4-(2-oxopiperidin-1-yl)phenyl]-2-oxo-1,3-oxazolidin-5-yl}methyl)thiophene-2-carboxamide

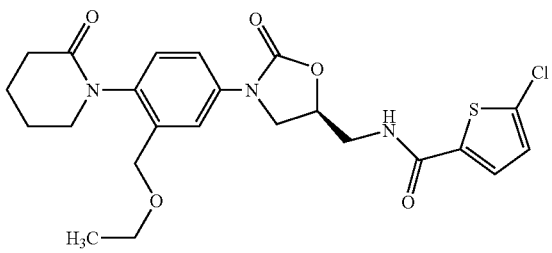

147 mg (0.58 mmol) of example 75A are dissolved in 6 ml of anhydrous acetonitrile and admixed at 0° C. with 184 mg (0.71 mmol) of example 1A. 198 mg (0.89 mmol) of magnesium perchlorate are added, the cooling is removed and the mixture is stirred at RT for 15 h. The solvent is removed under reduced pressure, and the residue is diluted with 10 ml of anhydrous butyronitrile and admixed with 192 mg (1.18 mmol) of 1,1-carbonyldiimidazole and 2 mg (0.01 mmol) of N,N-dimethylaminopyridine. After 16 h at reflux, the mixture is admixed with ethyl acetate, and the organic phase is removed, washed twice with water, once with saturated sodium hydrogencarbonate solution and once with saturated sodium chloride solution, dried, filtered and concentrated to dryness under reduced pressure. The residue is partly dissolved in dimethyl sulfoxide, and purification is effected by preparative HPLC with a gradient of water and acetonitrile, and the product fractions are combined and concentrated to dryness under reduced pressure. This affords 190 mg (65% of theory) of the desired compound.
$^1$H NMR (400 MHz, DMSO-d$_6$, δ/ppm): δ=8.97 (t, 1H), 7.70 (d, 1H), 7.57 (d, 1H), 7.52-7.44 (m, 1H), 7.24-7.17 (m, 2H), 4.87-4.78 (m, 1H), 4.33 (d, 1H), 4.23-4.15 (m, 2H), 3.89-3.82 (m, 1H), 3.64-3.51 (m, 3H), 3.45 (q, 2H), 3.39-3.33 (m, 1H), 2.39-2.30 (m, 2H), 1.88-1.78 (m, 4H) 1.20-1.11 (m, 3H).
LC-MS (Method 5): $R_t$=2.06 min
MS (ESIpos): m/z=492 (M+H)$^+$

Example 29

5-Chloro-N 4-({(5S)-3-[3-methyl-4-(5-oxo-1,4-oxazepan-4-yl)phenyl]-2-oxo-1,3-oxazolidin-5-yl}methyl)thiophene-2-carboxamide

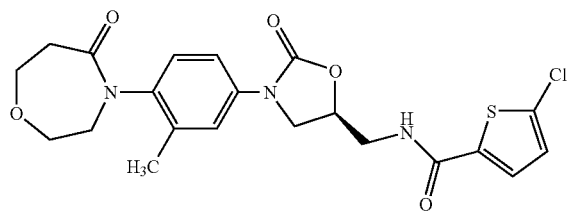

373 mg (1.69 mmol) of example 77A are dissolved in 20 ml of anhydrous acetonitrile and admixed at 0° C. with 526 mg (2.03 mmol) of example 1A. 567 mg (2.54 mmol) of magnesium perchlorate are added, the cooling is removed and the mixture is stirred at RT for 15 h. Then the mixture is concentrated to dryness under reduced pressure and taken up in 30 ml of butyronitrile. It is admixed with 549 mg (3.39 mmol) of 1,1-carbonyldiimidazole and 4 mg (0.03 mmol) of N,N-dimethylaminopyridine, and heated at reflux for 5 h. It is allowed to cool and the solvent is distilled off under reduced pressure. The residue is dissolved in acetonitrile and purified by preparative HPLC with a gradient of water and acetonitrile. The product fractions are combined and concentrated to dryness under reduced pressure. This affords 462 mg (59% of theory) of the desired compound.

$^1$H NMR (400 MHz, DMSO-$d_6$, δ/ppm): δ=8.97 (t, 1H), 7.70 (d, 1H), 7.42-7.35 (m, 2H), 7.20 (d, 1H), 7.13 (d, 1H), 4.87-4.79 (m, 1H), 4.17 (t, 1H), 3.85-3.78 (m, 6H), 3.65-3.56 (m, 3H), 2.92-2.84 (m, 1H), 2.75-2.67 (m, 1H), 2.15 (s, 3H).

LC-MS (Method 6): $R_t$=1.88 min
MS (ESIpos): m/z=464 (M+H)$^+$

Example 30

5-Chloro-N-({(5S)-3-[3-cyclopropyl-4-(5-oxo-1,4-oxazepan-4-yl)phenyl]-2-oxo-1,3-oxazolidin-5-yl}methyl)thiophene-2-carboxamide

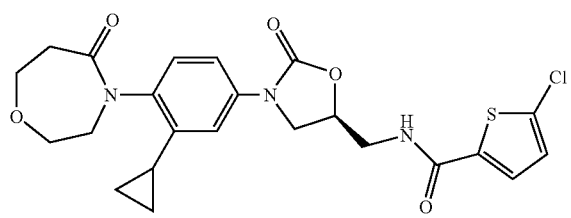

A solution of 236 mg (0.95 mmol) of the product from example 80A in 12 ml of acetonitrile is admixed with 229 mg (1.05 mmol) of the product from example 1A. To the suspension are added 320 mg (1.44 mmol) of magnesium perchlorate, after which the mixture is left to stir at RT for 5 h. Then 388 mg (2.40 mmol) of 1,1'-carbonyldiimidazole and 12 mg (0.09 mmol) of DMAP are added, and the mixture is stirred at RT for 12 h. Subsequently, the mixture is diluted with water, the water phase is extracted three times with ethyl acetate and the combined organic phases are dried over sodium sulfate. After filtration, the mixture is freed of the solvent and the residue is purified by means of preparative HPLC with a water/acetonitrile mixture. This affords 138 mg (29% of theory) of the desired product.

$^1$H NMR (400 MHz, DMSO-$d_6$, δ/ppm): 8.94 (t, 1H), 7.67 (d, 1H), 7.32 (ddd, 1H), 7.18 (d, 1H), 7.12 (d, 1H), 7.06 (dd, 1H), 4.86-4.75 (m, 1H), 4.16 (ddd, 1H), 3.91-3.72 (m, 6H), 3.67-3.52 (m, 3H), 2.92 (ddd, 1H), 2.69 (ddd, 1H), 1.92-1.84 (m, 1H), 1.01-0.82 (m, 2H), 0.77-0.68 (m, 1H), 0.50-0.41 (m, 1H).

HPLC (Method 1): $R_t$=3.99 min
MS (DCI, m/z): 507 (M+NH$_4$)$^+$.

Example 31

5-Chloro-N-({(5S)-3-[3-ethyl-4-(2-oxotetrahydropyrimidin-1(2H)-yl)phenyl]-2-oxo-1,3-oxazolidin-5-yl}methyl)thiophene-2-carboxamide

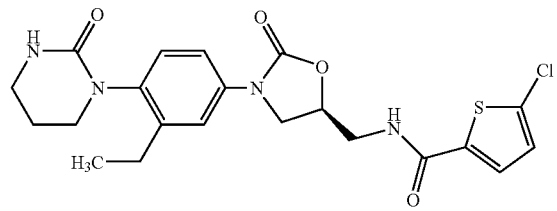

A solution of 12.8 mg (0.058 mmol) of the product from example 83A in 1 ml of acetonitrile is admixed with 14 mg (0.06 mmol) of the product from example 1A. To the suspension are added 19 mg (0.09 mmol) of magnesium perchlorate, after which the mixture is left to stir at RT for 4.5 h. Then 23.6 mg (0.146 mmol) of 1,1'-carbonyldiimidazole and 1 mg (0.01 mmol) of DMAP are added, and the mixture is stirred at RT for 18 h. Subsequently, the mixture is admixed with DMSO and purified by means of preparative HPLC with a water/acetonitrile mixture. This affords 10 mg (36% of theory) of the desired product.

$^1$H NMR (400 MHz, DMSO-$d_6$, δ/ppm): 8.95 (t, 1H), 7.68 (d, 1H), 7.42-7.29 (m, 2H), 7.21-7.12 (m, 2H), 6.42 (br. s, 1H), 4.89-4.78 (m, 1H), 4.18 (ddd, 1H), 3.88-3.82 (m, 1H), 3.65-3.48 (m, 4H), 3.40-3.18 (m, 4H), 1.98-1.87 (m, 2H), 1.13 (t, 3H).

HPLC (Method 1): $R_t$=3.98 min
MS (ESIpos, m/z): 463 (M+H)$^+$.

Example 32

5-Chloro-N-({(5S)-3-[3-isopropyl-4-(2-oxotetrahydropyrimidin-1(2H)-yl)phenyl]-2-oxo-1,3-oxazolidin-5-yl}methyl)thiophene-2-carboxamide

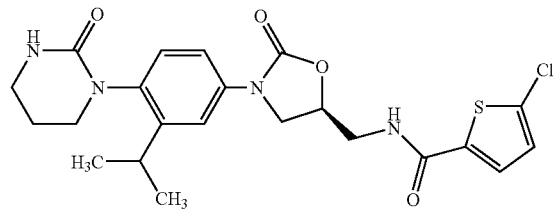

A solution of 75 mg (0.32 mmol) of the product from example 85A in 4 ml of acetonitrile is admixed with 77 mg (0.35 mmol) of the product from example 1A. To the suspension are added 107 mg (0.482 mmol) of magnesium perchlorate, after which the mixture is left to stir at RT for 5 h. Then 130 mg (0.804 mmol) of 1,1'-carbonyldiimidazole and 4 mg (0.03 mmol) of DMAP are added, and the mixture is stirred at RT for 18 h. Subsequently, it is diluted with water and extracted three times with ethyl acetate. The combined organic phases are dried over sodium sulfate. After filtration, the mixture is freed of the solvent under reduced pressure and the residue is purified by means of preparative HPLC with a water/acetonitrile mixture. This affords 51 mg (33% of theory) of the desired product.

$^1$H NMR (400 MHz, DMSO-d$_6$, δ/ppm): 8.96 (t, 1H), 7.68 (d, 1H), 7.44 (m, 1H), 7.29 (ddd, 1H), 7.18 (d, 1H), 7.12 (d, 1H), 6.41 (br. s, 1H), 4.88-4.78 (m, 1H), 4.19 (dd, 1H), 3.86 (dd, 1H), 3.60 (dd, 2H), 3.57-3.48 (m, 1H), 3.31-3.17 (m, 3H), 3.03-2.93 (m, 1H), 2.00-1.89 (m, 2H), 1.18-1.08 (m, 6H).

HPLC (Method 1): R$_t$=4.07 min

MS (ESIpos, m/z): 477 (M+H)$^+$.

Example 33

5-Chloro-N-({(5S)-2-oxo-3-[4-(2-oxopyridin-1(2H)-yl)-3-propylphenyl]-1,3-oxazolidin-5-yl}methyl)thiophene-2-carboxamide

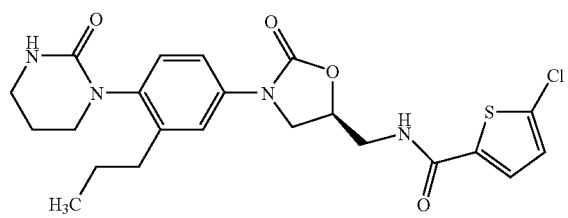

42 mg (0.18 mmol) of example 87A are dissolved in 3 ml of anhydrous acetonitrile and admixed at 0° C. with 56 mg (0.22 mmol) of example 1A. 60 mg (0.27 mmol) of magnesium perchlorate are added, the cooling is removed and the mixture is stirred at RT for 15 h. The solvent is concentrated under reduced pressure, and the residue is diluted with 5 ml of butyronitrile and admixed with 58 mg (0.36 mmol) of 1,1-carbonyldiimidazole and 0.4 mg (0.004 mmol) of N,N-dimethylaminopyridine. After 15 h at reflux, the mixture is allowed to cool and the solvent is distilled off under reduced pressure. The residue is dissolved in acetonitrile and purified by preparative HPLC with a gradient of water and acetonitrile. The product fractions are combined and concentrated to dryness under reduced pressure. This affords 44 mg (51% of theory) of the desired compound.

$^1$H NMR (400 MHz, DMSO-d$_6$, δ/ppm): δ=8.98 (t, 1H), 7.70 (d, 1H), 7.39-7.29 (m, 2H), 7.20 (d, 1H), 7.14 (d, 1H), 6.45 (br. s, 1H), 4.85-4.79 (m, 1H), 4.17 (t, 1H), 3.86-3.81 (m, 1H), 3.55-3.35 (m, 5H), 2.52-2.48 (m, 2H), 2.49-2.38 (m, 1H), 1.97-1.90 (m, 2H), 1.59-1.45 (m, 2H), 0.90 (t, 3H).

LC-MS (Method 6): R$_t$=2.10 min

MS (ESIpos): m/z=477 (M+H)$^+$

Example 34

5-Chloro-N-({(5S)-3-[3-methyl-4-(3-methyl-2-oxotetrahydropyrimidin-1(2H)-yl)phenyl]-2-oxo-1,3-oxazolidin-5-yl}methyl)thiophene-2-carboxamide

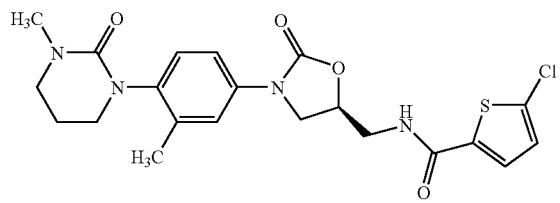

A solution of 45 mg (0.205 mmol) of the product from example 61A in 2 ml of acetonitrile is admixed with 49.1 mg (0.226 mmol) of the product from example 1A. To the suspension are added 68.7 mg (0.308 mmol) of magnesium perchlorate, after which the mixture is left to stir at RT for 3 h. Then 83.2 mg (0.513 mmol) of 1,1'-carbonyldiimidazole and 2.5 mg (0.02 mmol) of DMAP are added, and the mixture is stirred at RT. After 24 h, the mixture is diluted with 50 ml of water and the aqueous phase is extracted three times with ethyl acetate. The combined organic phases are dried over sodium sulfate. After filtration, the mixture is freed of the solvent and the residue is purified by means of preparative HPLC with an acetonitrile/water mixture. This affords 68 mg (71% of theory) of the desired product.

$^1$H NMR (400 MHz, DMSO-d$_6$, δ/ppm): 8.96 (dd, 1H), 7.68 (dd, 1H), 7.38-7.31 (m, 2H), 7.19 (d, 1H), 7.13 (d, 1H), 4.85-4.76 (m, 1H), 4.16 (dd, 1H), 3.83 (dd, 1H), 3.62-3.52 (m, 3H), 3.43-3.25 (m, 3H), 2.84 (s, 3H), 2.13 (s, 3H), 2.07-1.99 (m, 2H).

HPLC (Method 2): R$_t$=4.09 min.

MS (DCIpos, m/z): 463 (M+H)$^+$.

Example 35

5-Chloro-N-({(5S)-3-[3-methoxy-4-(3-methyl-2-oxotetrahydropyrimidin-1(2H)-yl)phenyl]-2-oxo-1,3-oxazolidin-5-yl}methyl)thiophene-2-carboxamide

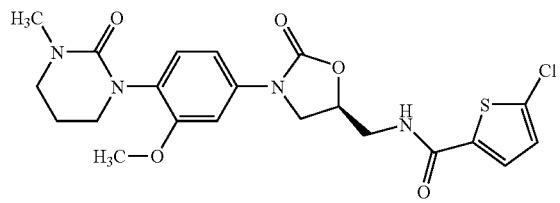

A solution of 350 mg (1.49 mmol) of the product from example 63A in 10 ml of acetonitrile is admixed with 356 mg (1.64 mmol) of the product from example 1A. To the suspension are added 498 mg (2.23 mmol) of magnesium perchlorate, after which the mixture is left to stir at RT for 2 h. Then 603 mg (3.72 mmol) of 1,1'-carbonyldiimidazole and 18 mg (0.15 mmol) of DMAP are added, and the mixture is stirred at RT. After 48 h, it is added to 200 ml of water and the aqueous phase is extracted three times with ethyl acetate. The precipitate formed is filtered off and dried under reduced pressure. This affords 232 mg (32% of theory) of the desired product.

$^1$H NMR (400 MHz, DMSO-$d_6$, δ/ppm): 8.97 (t, 1H), 7.69 (d, 1H), 7.29 (d, 1H), 7.19 (d, 1H), 7.10 (d, 1H), 6.94 (dd, 1H), 4.87-4.77 (m, 1H), 4.19 (dd, 1H), 3.85 (dd, 1H), 3.74 (s, 3H), 3.60 (t, 2H), 3.48-3.21 (m, 4H), 2.81 (s, 3H), 1.99 (tt, 2H).

HPLC (Method 2): $R_t$=4.04 min.
MS (ESIpos, m/z): 479 (M+H)$^+$.

Example 36

5-Chloro-N-{[(5S)-3-{4-[3-(2-hydroxyethyl)-2-oxotetrahydropyrimidin-1(2H)-yl]-3-methylphenyl}-2-oxo-1,3-oxazolidin-5-yl]methyl}thiophene-2-carboxamide

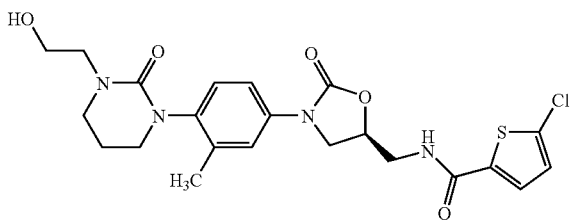

A solution of 232 mg (0.32 mmol) of the product from example 67A in 6 ml of THF is admixed with 195 mg (0.74 mmol) of a 1 molar solution of tetrabutylammonium fluoride in THF. The mixture is stirred at RT for 2 h. Then it is admixed with 60 ml of water, 30 ml of ethyl acetate and 6 ml of sodium chloride solution, and the phases are separated. The organic phase is extracted three times with ethyl acetate and the combined organic phases are dried over sodium sulfate. After filtration, the mixture is freed of the solvent and the residue is prepurified by chromatography on silica gel (20:1 dichloromethane/methanol). Subsequent purification by means of preparative HPLC with an acetonitrile/water mixture affords 29 mg (18% of theory) of the desired product.

$^1$H NMR (400 MHz, DMSO-$d_6$, δ/ppm): 8.96 (t, 1H), 7.69 (d, 1H), 7.40-7.31 (m, 2H), 7.19 (d, 1H), 7.13 (d, 1H), 4.86-4.77 (m, 1H), 4.64 (t, 1H), 4.16 (dd, 1H), 3.83 (dd, 1H), 3.59 (t, 2H), 3.58-3.40 (m, 5H), 3.38-3.22 (m, 3H), 2.12 (s, 3H), 2.06-1.95 (m, 2H).

HPLC (Method 1): $R_t$=3.91 min.
MS (ESIpos, m/z): 493 (M+H)$^+$.

Example 37

5-Chloro-N-{[(5S)-3-{3-chloro-4-[3-(2-hydroxyethyl)-2-oxotetrahydropyrimidin-1(2H)-yl]phenyl}-2-oxo-1,3-oxazolidin-5-yl]methyl}thiophene-2-carboxamide

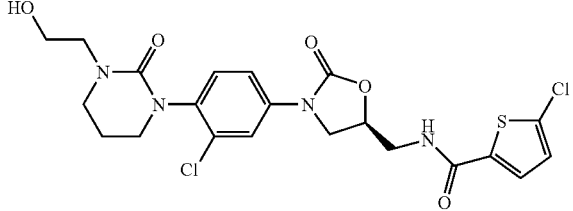

A solution of 355 mg (0.47 mmol) of the product from example 70A in 9 ml of THF is admixed with 290 mg (1.10 mmol) of a 1 molar solution of tetrabutylammonium fluoride in THF. The mixture is stirred at RT for 2 h. Then it is admixed with 80 ml of water, 50 ml of ethyl acetate and 6 ml of sodium chloride solution, and the phases are separated. The organic phase is extracted twice with ethyl acetate and the combined organic phases are dried over sodium sulfate. After filtration, the mixture is freed of the solvent and the residue is prepurified by chromatography on silica gel (20:1 dichloromethane/methanol). Subsequent purification by means of preparative HPLC with an acetonitrile/water mixture affords 39 mg (16% of theory) of the desired product.

$^1$H NMR (400 MHz, DMSO-$d_6$, δ/ppm): 8.96 (t, 1H), 7.73-7.67 (m, 2H), 7.46-7.36 (m, 1H), 7.34 (d, 1H), 7.19 (d, 1H), 4.84 (dddd, 1H), 4.64 (t, 1H), 4.19 (dd, 1H), 3.85 (dd, 1H), 3.60 (t, 2H), 3.52-3.33 (m, 6H), 3.33-3.24 (m, 1H), 2.06-1.97 (m, 2H).

HPLC (Method 1): $R_t$=3.95 min.
MS (ESIpos, m/z): 513 (M+H)$^+$.

Example 38

5-Chloro-N-{[(5S)-3-{4-[3-(2-hydroxyethyl)-2-oxotetrahydropyrimidin-1(2H)-yl]-3-(trifluoro-methyl)phenyl}-2-oxo-1,3-oxazolidin-5-yl]methyl}thiophene-2-carboxamide

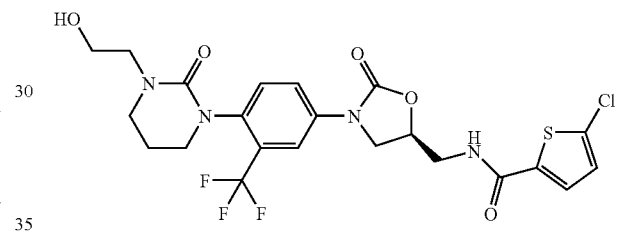

A solution of 8.88 g (11.3 mmol) of the product from example 73A in 225 ml of THF is admixed with 6.95 g (26.6 mmol) of a 1 molar solution of tetrabutylammonium fluoride in THF. The mixture is stirred at RT for 45 min. Then it is freed of the solvent and the residue is purified by chromatography on silica gel (40:1→10:1 dichloromethane/methanol). This affords 5.24 g (80% of theory) of the desired product.

$^1$H NMR (400 MHz, DMSO-$d_6$, δ/ppm): 8.96 (dd, 1H), 7.95 (dd, 1H), 7.75-7.66 (m, 2H), 7.46 (d, 1H), 7.19 (d, 1H), 4.91-4.82 (m, 1H), 4.63 (t, 1H), 4.24 (dd, 1H), 3.91 (dd, 1H), 3.63-3.22 (m, 10H), 2.06-1.97 (m, 2H).

HPLC (Method 2): $R_t$=4.03 min.
MS (ESIpos, m/z): 547 (M+H)$^+$.

Example 39

N-({(5S)-3-[4-(3-(2-Hydroxyethyl)-2-oxopiperidin-1-yl)-3-chlorophenyl]-2-oxo-1,3-oxazolidin-5-yl}methyl)-5-chlorothiophene-2-carboxamide

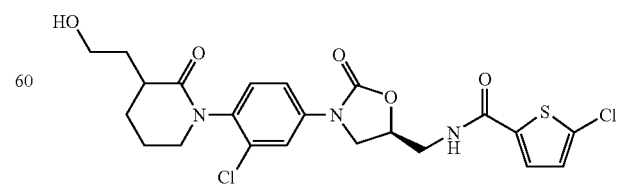

A solution of 100 mg (0.197 mmol) of the compound from example 101A in a mixture of 1 ml each of tetrahydrofuran and water is admixed with 49 μl (0.004 mmol) of a 2.5 percent solution of osmium tetroxide in tert-butanol and 126 mg (0.59 mmol) of sodium periodate. The reaction mixture is stirred at RT for 16 hours. Subsequently, it is diluted with approx. 5 ml of water and extracted with dichloromethane. The organic extract is dried over anhydrous magnesium sulfate and filtered, and the filtrate is freed of the solvent on a rotary evaporator. The resulting residue is dissolved again in a mixture of 1 ml each of tetrahydrofuran and water, and admixed with 8 mg (0.2 mmol) of sodium borohydride. After stirring at RT for 1 hour, the mixture is again diluted with approx. 5 ml of water and extracted with dichloromethane. The organic extract is dried over anhydrous magnesium sulfate and filtered, and the filtrate is freed of the solvent on a rotary evaporator. The resulting residue is purified by means of preparative HPLC with an acetonitrile/water mixture. This affords 52 mg (50% of theory) of the title compound.

$^1$H NMR (400 MHz, CDCl$_3$, δ/ppm): 7.73 and 7.68 (2 dd, together 1H), 7.43 and 7.41 (2 d, together 1H), 7.31 (d, 1H), 7.21 and 7.20 (2 d, together 1H), 6.89 (d, 1H), 6.80 (t, 1H), 4.89-4.82 (m, 1H), 4.07-4.02 (m, 2H), 3.83-3.69 (m, 5H), 3.62-3.47 (m, 2H), 2.71-2.62 (m, 1H), 2.16-1.94 (m, 4H), 1.83-1.74 (m, 2H).

HPLC (Method 5): R$_t$=1.96 min.

MS (ESIpos, m/z): 512/514/516 (Cl$_2$, $^{35}$Cl/$^{37}$Cl) (M+H)$^+$.

Example 40

N-({(5S)-3-[4-(3-(2-Hydroxyethyl)-2-oxopiperidin-1-yl)-3-chlorophenyl]-2-oxo-1,3-oxazolidin-5-yl}methyl)-5-chlorothiophene-2-carboxamide (diastereomer 1)

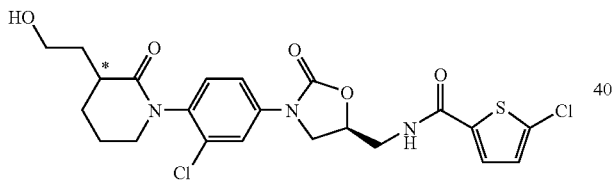

The diastereomer mixture from example 39 can be separated chromatographically on the preparative scale into the pure diastereomers. To this end, 50 mg of the compound from example 39 are dissolved in 3.5 ml of the eluent and chromatographed in one portion. This affords 13 mg (26% of theory) of the title compound (diastereomer 1) and 16 mg (32% of theory) of diastereomer 2.

Method: column: Daicel Chiralpak AD-H, 5 μm, 250 mm×20 mm; eluent: ethanol+1% water+0.2% trifluoroacetic acid; flow rate: 15 ml/min; temperature: 40° C.; UV detection: 220 nm.

Retention time: 15.9 min (diastereomer 1), 19.3 min (diastereomer 2)

$^1$H NMR (400 MHz, CDCl$_3$, δ/ppm): 7.71 (d, 1H), 7.46 and 7.43 (2 dd, together 1H), 7.30 (d, 1H), 7.22 and 7.21 (2 d, together 1H), 6.91 (d, 1H), 6.61 and 6.59 (2 t, together 1H), 4.89-4.82 (m, 1H), 4.09-4.03 (m, 1H), 3.88-3.71 (m, 5H), 3.63-3.45 (m, 2H), 2.72-2.62 (m, 1H), 2.14-1.93 (m, 4H), 1.83-1.74 (m, 1H), 1.71 (broad, 1H).

HPLC (Method 4): R$_t$=2.07 min.

MS (ESIpos, m/z): 512/514/516 (Cl$_2$, $^{35}$Cl/$^{37}$Cl) (M+H)$^+$.

Example 41

N-({(5S)-3-[4-(3-(2-Hydroxyethyl)-2-oxopiperidin-1-yl)-3-chlorophenyl]-2-oxo-1,3-oxazolidin-5-yl}methyl)-5-chlorothiophene-2-carboxamide (diastereomer 2)

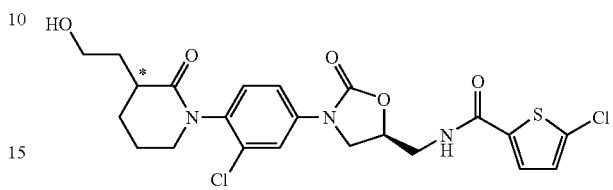

The diastereomer mixture from example 39 can be separated chromatographically on the preparative scale into the pure diastereomers. To this end, 50 mg of the compound from example 39 are dissolved in 3.5 ml of the eluent and chromatographed in one portion. This affords 16 mg (32% of theory) of the title compound (diastereomer 2) and 13 mg (26% of theory) of diastereomer 1.

Method: column: Daicel Chiralpak AD-H, 5 μm, 250 mm×20 mm; eluent: ethanol+1% water+0.2% trifluoroacetic acid; flow rate: 15 ml/min; temperature: 40° C.; UV detection: 220 nm.

Retention time: 15.9 min (diastereomer 1), 19.3 min (diastereomer 2)

$^1$H NMR (400 MHz, CDCl$_3$, δ/ppm): 7.73-7.68 (m, 1H), 7.48-4.41 (m, 1H), 7.30 (d, 1H), 7.25-7.20 (m, 1H, partly obscured by the CHCl$_3$ signal), 6.90 (d, 1H), 6.67-6.61 (m, 1H), 4.89-4.82 (m, 1H), 4.10-4.01 (m, 1H), 3.88-3.69 (m, 5H), 3.63-3.44 (m, 2H), 2.72-2.62 (m, 1H), 2.28 (broad, 1H), 2.16-1.92 (m, 4H), 1.85-1.73 (m, 1H).

HPLC (Method 4): R$_t$=2.07 min.

MS (ESIpos, m/z): 512/514/516 (Cl$_2$, $^{35}$Cl/$^{37}$Cl) (M+H)$^+$.

Example 42

5-Chloro-N-[((5S)-3-{3-chloro-4-[3-(hydroxymethyl)-2-oxopiperidin-1-yl]phenyl}-2-oxo-1,3-oxazolidin-5-yl)methyl]thiophene-2-carboxamide

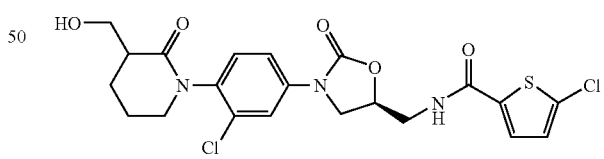

A solution of 600 mg (0.814 mmol) of the compound from example 95A in 10 ml of tetrahydrofuran is admixed at 0° C. with 855 μl (0.855 mmol) of a 1 molar solution of tetrabutylammonium fluoride in tetrahydrofuran. After five hours at RT, the reaction mixture is concentrated to dryness on a rotary evaporator. The resulting residue is purified by means of flash chromatography using silica gel with 2:1→1:2 cyclohexane/ethyl acetate as the eluent. This affords 342 mg (84% of theory) of the title compound.

$^1$H NMR (400 MHz, DMSO-d$_6$, δ/ppm): 7.72 and 7.71 (2 t, together 1H), 7.48-7.41 (m, 1H), 7.31 (d, 1H), 7.23 (d, 1H), 6.91 (d, 1H), 6.64 and 6.60 (m, 1H), 4.90-4.83 (m, 1H), 4.07 and 4.05 (2 t, together 1H), 3.87-3.73 (m, 5H), 3.60-3.45 (m, 2H), 2.72-2.61 (m, 1H), 2.10-1.96 (m, 3H), 1.76-1.63 (m, 1H).

HPLC (Method 2): $R_t$=4.09 min.

MS (ESIpos, m/z): 498/500/502 (Cl$_2$, $^{35}$Cl/$^{37}$Cl) (M+H)$^+$.

Example 43

5-Chloro-N-[((5S)-3-{3-chloro-4-[3-(hydroxymethyl)-2-oxopiperidin-1-yl]phenyl}-2-oxo-1,3-oxazolidin-5-yl)methyl]thiophene-2-carboxamide (diastereomer 1)

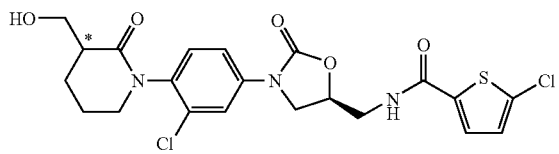

The diastereomer mixture from example 42 can be separated chromatographically on the preparative scale into the pure diastereomers. To this end, 320 mg of the compound from example 46 are dissolved in 12 ml of the eluent and chromatographed in three portions. This affords 167 mg (52% of theory) of the title compound (diastereomer 1) and 128 mg (40% of theory) of diastereomer 2.

Method: column: Daicel Chiralpak AD-H, 5 μm, 250 mm×20 mm; eluent: ethanol+1% water+0.2% trifluoroacetic acid; flow rate: 15 ml/min; temperature: 40° C.; UV detection: 220 nm.

Retention time: 12.4 min (diastereomer 1), 22.3 min (diastereomer 2)

$^1$H NMR (400 MHz, CDCl$_3$, δ/ppm): 7.71 (d, 1H), 7.47 and 7.43 (2 d, together 1H), 7.30 and 7.28 (2 d, together 1H), 7.23 and 7.22 (2 d, together 1H, partly obscured by the CHCl$_3$ signal), 6.91 and 6.90 (2 d, together 1H), 6.61 and 6.57 (2 t, together 1H), 4.89-4.83 (m, 1H), 4.10 and 4.03 (m, 1H), 3.87-3.72 (m, 5H), 3.64-3.44 (m, 2H), 2.72-2.61 (m, 1H), 2.13-1.83 (m, 4H), 1.76-1.64 (m, 1H).

HPLC (Method 4): $R_t$=2.11 min.

MS (ESIpos, m/z): 498/500/502 (Cl$_2$, $^{35}$Cl/$^{37}$Cl) (M+H)$^+$.

Example 44

N-({(5S)-3-[4-(3-(2-Hydroxyethyl)-2-oxopiperidin-1-yl)-3-methylphenyl]-2-oxo-1,3-oxazolidin-5-yl}methyl)-5-chlorothiophene-2-carboxamide

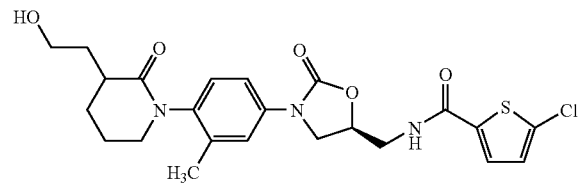

In analogy to the process described in example 39, 100 mg (0.205 mmol) of the compound from example 102A are used to obtain, after preparative HPLC, 60 mg (60% of theory) of the title compound.

$^1$H NMR (400 MHz, CDCl$_3$, δ/ppm): 7.42-7.36 (m, 2H), 7.30 (d, 1H), 7.09 (dd, 1H), 6.90 (d, 1H), 6.67-6.62 (m, 1H), 4.87-4.80 (m, 1H), 4.09-4.03 (m, 1H), 3.88-3.67 (m, 5H), 3.63-3.53 (m, 1H), 3.48-3.35 (m, 1H), 2.70-2.61 (m, 1H), 2.18 (s, 3H), 2.15-1.73 (m, 7H).

HPLC (Method 2): $R_t$=3.94 min.

MS (ESIpos, m/z): 492/494 ($^{35}$Cl/$^{37}$Cl) (M+H)$^+$.

Example 45

N-({(5S)-3-[4-(3-(2-Hydroxyethyl)-2-oxopiperidin-1-yl)-3-methylphenyl]-2-oxo-1,3-oxazolidin-5-yl}methyl)-5-chlorothiophene-2-carboxamide (diastereomer 1)

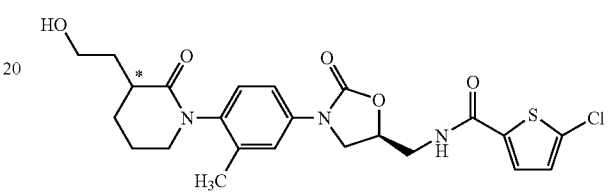

The diastereomer mixture from example 44 can be separated chromatographically on the preparative scale into the pure diastereomers. To this end, 53 mg of the compound from example 44 are dissolved in 10 ml of ethanol and chromatographed in 20 portions. This affords 20 mg (38% of theory) of the title compound (diastereomer 1) and 24 mg (45% of theory) of diastereomer 2.

Method: column: Daicel Chiralpak AD-H, 5 μm, 250 mm×20 mm; eluent: 70:30 ethanol/isohexane; flow rate: 15 ml/min; temperature: 30° C.; UV detection: 220 nm.

Retention time (Method 11): 18.52 min (diastereomer 1); 22.57 min (diastereomer 2).

$^1$H NMR (400 MHz, CDCl$_3$, δ/ppm): 7.43-7.37 (m, 2H), 7.29 (d, 1H), 7.10 (dd, 1H), 6.90 (d, 1H), 6.53-6.50 (m, 1H), 4.86-4.81 (m, 1H), 4.33-4.25 (m, 1H), 4.10-4.04 (m, 1H), 3.90-3.65 (m, 5H), 3.61-3.53 (m, 1H), 3.48-3.35 (m, 1H), 2.70-2.61 (m, 1H), 2.19 (s, 3H), 2.15-1.93 (m, 4H), 1.84-1.73 (m, 2H).

HPLC (Method 1): $R_t$=3.93 min.

Example 46

N-({(5S)-3-[4-(3-(2-Hydroxyethyl)-2-oxopiperidin-1-yl)-3-methylphenyl]-2-oxo-1,3-oxazolidin-5-yl}methyl)-5-chlorothiophene-2-carboxamide (diastereomer 2)

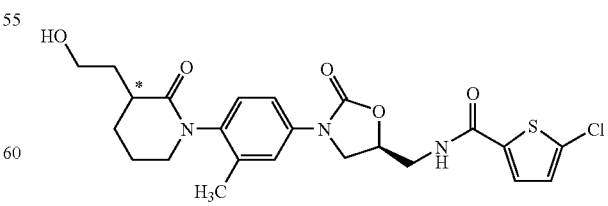

The diastereomer mixture from example 44 can be separated chromatographically on the preparative scale into the pure diastereomers. To this end, 53 mg of the compound from example 44 are dissolved in 10 ml of ethanol and chromatographed in 20 portions. This affords 24 mg (45% of theory) of the title compound (diastereomer 2) and 20 mg (38% of theory) of diastereomer 1.

Method: column: Daicel Chiralpak AD-H, 5 μm, 250 mm×20 mm; eluent: 70:30 ethanol/isohexane; flow rate: 15 ml/min; temperature: 30° C.; UV detection: 220 nm.

Retention time (Method 11): 18.52 min (diastereomer 1); 22.57 min (diastereomer 2).

$^1$H NMR (400 MHz, CDCl$_3$, δ/ppm): 7.43-7.37 (m, 2H), 7.30 (d, 1H), 7.10 (dd, 1H), 6.90 (d, 1H), 6.58-6.53 (m, 1H), 4.87-4.81 (m, 1H), 4.35-4.26 (m, 1H), 4.10-4.04 (m, 1H), 3.88-3.68 (m, 5H), 3.63-3.53 (m, 1H), 3.48-3.35 (m, 1H), 2.70-2.60 (m, 1H), 2.19 (s, 3H), 2.14-1.91 (m, 4H), 1.84-1.73 (m, 2H).

HPLC (Method 1): R$_t$=3.93 min.

Example 47

5-Chloro-N-[((5S)-3-{3-chloro-4-[3-(3-hydroxypropyl)-2-oxopiperidin-1-yl]phenyl}-2-oxo-1,3-oxazolidin-5-yl)methyl]thiophene-2-carboxamide (diastereomer 2)

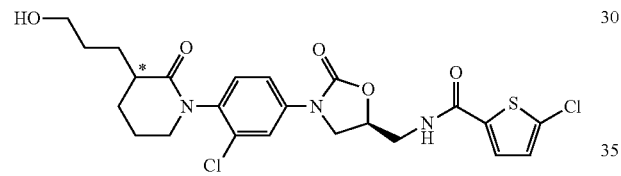

A solution of 200 mg (0.393 mmol) of the product from diastereomer 2 of example 101A in 4 ml of anhydrous tetrahydrofuran is admixed at 0° C. with 1.2 ml (0.590 mmol) of a 0.5 molar solution of 9-borabicyclo[3.3.1]nonane in tetrahydrofuran. After the dropwise addition has ended, the reaction mixture is heated to reflux for two hours. Subsequently, it is cooled again to 0° C. and admixed at this temperature with 160 μl (0.393 mmol) of 10% sodium hydroxide solution and 121 μl (1.18 mmol) of 30% hydrogen peroxide solution. The cooling bath is removed and, once the reaction mixture has reached RT, it is left to stir for another about 30 minutes. Then it is admixed with 20 ml of water and extracted with ethyl acetate. The organic extract is dried over anhydrous magnesium sulfate. After filtration, the solvent is removed on a rotary evaporator and the crude product is isolated by means of preparative HPLC of an acetonitrile/water mixture. This affords 97 mg of the reactant, example 102A, and 60 mg (56% of theory, based on conversion) of the title compound are obtained.

$^1$H NMR (400 MHz, CDCl$_3$, δ/ppm): 7.76 and 7.62 (2 d, together 1H), 7.45 and 7.33 (2 dd, together 1H), 7.31 (d, 1H), 7.20 and 7.17 (2 d, together 1H), 6.96 (s, broad, 1H), 6.88 (d, 1H), 4.86-4.78 (m, 1H), 4.01 (quart, 1H), 3.80 (dd, 1H), 3.73 (dd, 1H), 3.70-3.57 (m, 3H), 3.54-3.43 (m, 1H), 2.58-2.51 (m, 1H), 2.13-1.91 (m, 4H), 1.83-1.50 (m, 6H).

HPLC (Method 4): R$_t$=2.22 min.

MS (ESIpos, m/z): 526/528/530 (Cl$_2$, $^{35}$Cl/$^{37}$Cl) (M+H)$^+$.

Example 48

5-Chloro-N-[((5S)-3-{4-[3-(3-hydroxypropyl)-2-oxopiperidin-1-yl]-3-methylphenyl}-2-oxo-1,3-oxazolidin-5-yl)methyl]thiophene-2-carboxamide

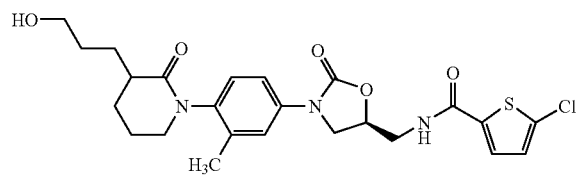

Analogously to the process described under example 47, 200 mg (0.410 mmol) of the compound from example 102A are reacted with 9-borabicyclo[3.3.1]nonane. This affords 77 mg of the reactant and 84 mg (66% of theory, based on conversion) of the title compound.

$^1$H NMR (400 MHz, CDCl$_3$, δ/ppm): 7.43-7.31 (m, 2H), 7.31 (d, 1H), 7.10-7.03 (m, 1H), 6.89 (d, 1H), 6.81-6.72 (m, 1H), 5.86-5.72 (m, 1H), 4.83-4.75 (m, 1H), 4.05-3.99 (m, 1H), 3.87-3.72 (m, 3H), 3.69-3.61 (m, 2H), 3.58-3.51 (m, 1H), 3.47-3.33 (m, 1H), 2.57-2.50 (m, 1H), 2.18 and 2.17 (2 s, together 3H), 2.10-1.87 (m, 4H), 1.79-1.51 (m, 4H).

HPLC (Method 2): R$_t$=4.01 min.

MS (ESIpos, m/z): 506/508 ($^{35}$Cl/$^{37}$Cl) (M+H)$^+$.

Example 49

5-Chloro-N-[((5S)-3-{4-[3-(3-hydroxypropyl)-2-oxopiperidin-1-yl]-3-methylphenyl}-2-oxo-1,3-oxazolidin-5-yl)methyl]thiophene-2-carboxamide (diastereomer 1)

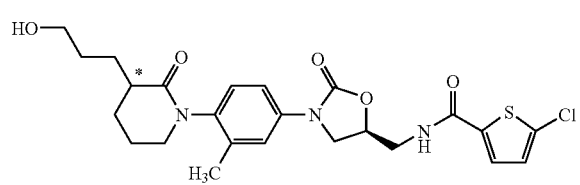

The diastereomer mixture from example 48 can be separated chromatographically on the preparative scale into the pure diastereomers. To this end, 32 mg of the compound from example 48 are dissolved in 2.5 ml of ethanol and chromatographed in one portion. This affords 14 mg (44% of theory) of the title compound (diastereomer 1) and 14 mg (44% of theory) of diastereomer 2.

Method: column: Daicel Chiralpak AD-H, 5 μm, 250 mm×20 mm; eluent: 70:30 ethanol/isohexane; flow rate: 15 ml/min; temperature: 40° C.; UV detection: 220 nm.

Retention time (Method 11): 11.62 min (diastereomer 1); 17.08 min (diastereomer 2).

$^1$H NMR (400 MHz, CDCl$_3$, δ/ppm): 7.40-7.35 (m, 2H), 7.31 (d, 1H), 7.10-7.05 (m, 1H), 6.89 (d, 1H), 6.77-6.73 (m, 1H), 4.82-4.74 (m, 1H), 4.05-4.00 (m, 1H), 3.83-3.76 (m, 2H), 3.69-3.52 (m, 4H), 3.46-3.33 (m, 1H), 2.57-2.50 (m, 1H), 2.36 (s, broad, 1H), 2.18 (s, 3H), 2.13-1.89 (m, 4H), 1.80-1.63 (m, 4H).

HPLC (Method 1): R$_t$=4.03 min.

Example 50

5-Chloro-N-[((5S)-3-{4-[3-(3-hydroxypropyl)-2-oxopiperidin-1-yl]-3-methylphenyl}-2-oxo-1,3-oxazolidin-5-yl)methyl]thiophene-2-carboxamide (diastereomer 2)

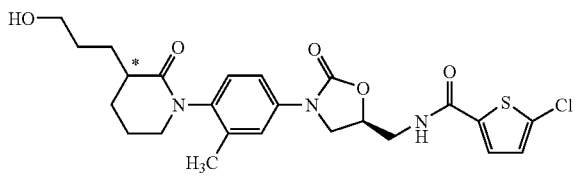

The diastereomer mixture from example 48 can be separated chromatographically on the preparative scale into the pure diastereomers. To this end, 32 mg of the compound from example 48 are dissolved in 2.5 ml of ethanol and chromatographed in one portion. This affords 14 mg (44% of theory) of the title compound (diastereomer 2) and 14 mg (44% of theory) of diastereomer 1.

Method: column: Daicel Chiralpak AD-H, 5 μm, 250 mm×20 mm; eluent: 70:30 ethanol/isohexane; flow rate: 15 ml/min; temperature: 40° C.; UV detection: 220 nm.

Retention time (Method 11): 11.62 min (diastereomer 1); 17.08 min (diastereomer 2).

$^1$H NMR (400 MHz, CDCl$_3$, δ/ppm): 7.41-7.32 (m, 2H), 7.30 (d, 1H), 7.10-7.05 (m, 1H), 6.90 (d, 1H), 6.69-6.63 (m, 1H), 4.83-4.78 (m, 1H), 4.07-4.01 (m, 1H), 3.87-3.77 (m, 2H), 3.71-3.60 (m, 3H), 3.59-3.51 (m, 1H), 3.46-3.34 (m, 1H), 2.57-2.50 (m, 1H), 2.36 (s, broad, 1H), 2.18 and 2.17 (2 s, together 3H), 2.13-1.90 (m, 4H), 1.79-1.63 (m, 4H).

HPLC (Method 1): R$_t$=4.02 min.

Example 51

5-Chloro-N-({(5S)-3-[3-(methoxymethyl)-4-(3-methyl-2-oxopyridin-1(2H)-yl)phenyl]-2-oxo-1,3-oxazolidin-5-yl}methyl)thiophene-2-carboxamide

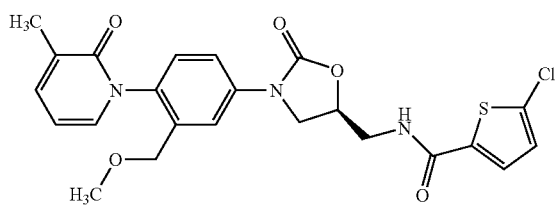

500 mg (2.05 mmol) of example 34A are dissolved in 20 ml of anhyrous acetonitrile and admixed at 0° C. with 686 mg (3.07 mmol) of example 1A. 685 mg (3.07 mmol) of magnesium perchlorate are added, the cooling is removed and the mixture is stirred at RT for 16 h. The solvent is removed under reduced pressure, and the residue is taken up in butyronitrile, admixed with 664 mg (4.01 mmol) of 1,1-carbonyldiimidazole and 5 mg (0.03 mmol) of N,N-dimethylaminopyridine, and heated at reflux. After 16 h, the same amount of N,N-dimethylaminopyridine is added again and the mixture is once again heated at reflux for 16 h. It is allowed to cool, the solvent is distilled off under reduced pressure and the mixture is diluted with 300 ml of dichloromethane. The dichloromethane phase is washed with 1N hydrochloric acid and saturated sodium chloride solution, filtered, dried over sodium sulfate and concentrated to dryness under reduced pressure. The residue is dissolved in DMSO and purified by preparative HPLC with a gradient of water and acetonitrile. The product fractions are combined and concentrated to dryness under reduced pressure. This affords 576 mg (58% of theory) of the desired compound.

$^1$H NMR (400 MHz, DMSO-d$_6$, δ/ppm): δ=8.98 (t, 1H), 7.73-7.65 (m, 2H), 7.62-7.55 (m, 1H), 7.42 (d, 1H), 7.35 (d, 1H), 7.27 (d, 1H), 7.18 (d, 1H), 6.23 (t, 1H), 4.91-4.82 (m, 1H), 4.28-4.08 (m, 3H), 3.95-3.87 (m, 1H), 3.68-3.58 (m, 2H), 3.35 (s, 3H), 2.04 (s, 3H).

LC-MS (Method 3): R$_t$=1.88 min
MS (ESIpos): m/z=488 (M+H)$^+$

Example 52

5-Chloro-N-({(5S)-3-[3-(ethoxymethyl)-4-(3-methyl-2-oxopyridin-1(2H)-yl)phenyl]-2-oxo-1,3-oxazolidin-5-yl}methyl)thiophene-2-carboxamide 388 mg (1.5 mmol) of example 34A are dissolved in 15 ml of anhydrous acetonitrile and admixed at 0° C. with 467 mg (1.80 mmol) of example 1A. 503 mg (2.25 mmol) of magnesium perchlorate are added, the cooling is removed and the mixture is stirred at RT for 16 h. The solvent is removed under reduced pressure, and the residue is taken up in butyronitrile, admixed with 487 mg (3.00 mmol) of 1,1-carbonyldiimidazole and 3.6 mg (0.03 mmol) of N,N-dimethylaminopyridine, and heated at reflux for 15 h. The mixture is allowed to cool, the solvent is distilled off under reduced pressure, and the residue is dissolved in dimethyl sulfoxide and purified by preparative HPLC with a gradient of water and acetonitrile. The product fractions are combined and concentrated to dryness under reduced pressure. This affords 395 mg (52% of theory) of the desired compound.

$^1$H NMR (400 MHz, DMSO-d$_6$, δ/ppm): δ=8.99 (t, 1H), 7.72-7.67 (m, 2H), 7.62-7.53 (m, 1H), 7.41 (d, 1H), 7.34 (d, 1H), 7.26 (d, 1H), 7.20 (d, 1H), 6.22 (t, 1H), 4.91-4.82 (m, 1H), 4.28-4.14 (m, 3H), 3.93-3.87 (m, 1H), 3.68-3.59 (m, 2H), 3.38-3.25 (m, 2H), 2.04 (s, 3H), 1.03 (t, 3H).

LC-MS (Method 5): R$_t$=2.15 min
MS (ESIpos): m/z=502 (M+H)$^+$

B. Assessment Of Pharmacological Activity

The suitability of the inventive compounds for treatment of thromboembolic disorders can be demonstrated using the following assay systems:

a) Test Descriptions (In Vitro)

a.1) Measurement of the Factor Xa Inhibition in Buffer

To determine the factor Xa inhibition of the substances listed above, a biological test system is constructed in which the conversion of a factor Xa substrate is used for determining the enzymatic activity of human factor Xa. In this test, factor Xa cleaves aminomethylcoumarin, which is measured by fluorescence, from the peptidic substrate. The determinations are carried out in microtiter plates.

Substances to be tested are dissolved in various concentrations in dimethyl sulfoxide and incubated for 30 min with human factor Xa (1.3 nmol/l dissolved in 50 mmol/l of tris buffer [C,C,C-tris(hydroxymethyl)aminomethane], 100 mmol/l of sodium chloride, 5 mmol/l of calcium chloride, 0.1% BSA [bovine serum albumin], pH 7.4) at 22° C. The substrate (5 µmol/l Boc-Ile-Glu-Gly-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulfoxide instead of test substance in dimethyl sulfoxide) and the $IC_{50}$ values are calculated from the concentration/activity relationships.

a.2) Measurement of Thrombin Inhibition in Buffer

To determine the thrombin inhibition of the substances listed above, a biological test system is constructed in which the conversion of a thrombin substrate is used for determining the enzymatic activity of human thrombin. In this test, thrombin cleaves aminomethylcoumarin, which is measured fluorescently, from the peptidic substrate. The determinations are carried out in microtiter plates.

Substances to be tested are dissolved in various concentrations in dimethyl sulfoxide and incubated for 15 min with human thrombin (0.06 nmol/l dissolved in 50 mmol/l of Tris buffer [C,C,C-tris(hydroxymethyl)aminomethane], 100 mmol/l of sodium chloride, 0.1% BSA [bovine serum albumin], pH 7.4) at 22° C. The substrate (5 µmol/l Boc-Asp (OBzl)-Pro-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulfoxide instead of test substance in dimethyl sulfoxide) and the $IC_{50}$ values are calculated from the concentration/activity relationships.

a.3) Determination of the Selectivity

To demonstrate the selectivity of the substances with respect to thrombin and factor Xa inhibition, the test substances are examined for their inhibition of other human serine proteases, such as factor XIIa, factor XIa, trypsin and plasmin. To determine the enzymatic activity of factor XIIa (10 nmol/l from Kordia), factor XIa (0.4 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of sodium chloride, 0.1% BSA [bovine serum albumin], 5 mmol/l of calcium chloride, pH 7.4) and incubated for 15 min with test substance in various concentrations in dimethyl sulfoxide and also with dimethyl sulfoxide without test substance. The enzymatic reaction is then started by addition of the appropriate substrates (5 µmol/l of H-Pro-Phe-Arg-AMC from Bachem for factor XIIa, 5 µmol/l of Boc-Ile-Glu-Gly-Arg-AMC from Bachem for trypsin, 5 µmol/l of Boc-Glu(OBzl)-Ala-Arg-AMC from Bachem for factor XIa, 50 µmol/l of MeOSuc-Ala-Phe-Lys-AMC from Bachem for plasmin). After an incubation time of 30 min at 22° C., fluorescence is measured (excitation: 360 nm, emission: 460 nm). The measured emissions of the test batches with test substance are compared to the control batches without test substance (only dimethyl sulfoxide instead of test substance in dimethyl sulfoxide), and the $IC_{50}$ values are calculated from the concentration/activity relationships.

a.4) Determination of the Factor Xa-Inhibitory Activity of the Potential Inhibitors in Plasma Samples To determine the inhibition of factor Xa in plasma samples, the factor X present in plasma is activated by a protease from rattlesnake toxin. The factor Xa activity or its inhibition by potential inhibitors is then measured by addition of a chromogenic substrate.

Various concentrations of the substances to be tested are dissolved in dimethyl sulfoxide and diluted with an aqueous refludan solution (10 µg/ml). In clear 96-well plates having a flat bottom, 30 µl of citrate plasma (Octapharma) are mixed with 10 µl of the substance dilution. Then, either 20 µl of a solution of a rattlesnake toxin (Russel viper venom (RVV); RVV reagent: Pentapharm 121-06, final concentration 0.6 mU) in an aqueous calcium chloride solution buffer (final concentration of calcium chloride 0.05 M) or 20 µl of the aqueous calcium chloride solution (final concentration of calcium chloride 0.05 M) without RVV reagent (as reference for an unstimulated sample) are added. After addition of 20 µl of ChromozymX substrate (final concentration 1.6 mmol/l, Bachem L-1565, diluted in water) the samples are measured in a SpectraFluor Reader using a measurement filter of 405 nm each minute over a period of 20 minutes. The $IC_{50}$ value is determined when about 70% of the maximum signal is reached (about 12 min).

Representative activity data from this test are listed in Table 1 below:

TABLE 1

| Example No. | $IC_{50}$ [nM] |
|---|---|
| 4 | 201 |
| 7 | 206 |
| 9 | 149 |
| 16 | 213 |
| 18 | 319 |
| 19 | 361 |
| 27 | 39 |
| 30 | 25 |
| 32 | 70 |
| 35 | 552 |
| 38 | 252 | a.5) Determination of the Thrombin-Inhibitory Activity of the Potential Inhibitors in Plasma Samples Various concentrations of the substances to be tested are dissolved in dimethyl sulfoxide and diluted with water. In white 96-well plates having a flat bottom, 20 µl of substance dilution are mixed with 20 µl of ecarin solution (ecarin reagent, from Sigma E-0504, final concentration 20 mU per batch) in Ca buffer (200 mM Hepes+560 mM sodium chloride+10 mM calcium chloride+0.4% PEG) or with 20 µl of Ca buffer (as unstimulated control). Furthermore, 20 µl of fluorogenic thrombin substrate (from Bachem I-1120, final concentration 50 µmol/l) and 20 µl of citrate plasma (from Octapharma) are added and homogenized thoroughly. The plate is measured in a SpectraFluorplus Reader using an excitation filter of 360 nm and an emission filter of 465 nm each minute over a period of 20 minutes. The $IC_{50}$ value is determined when about 70% of the maximum signal is reached (about 12 min).

Representative activity data from this test are listed in Table 2 below:

TABLE 2

| Example No. | IC$_{50}$ [nM] |
|---|---|
| 4 | 286 |
| 7 | 277 |
| 9 | 247 |
| 16 | 14 |
| 18 | 502 |
| 19 | 8 |
| 27 | 54 |
| 30 | 34 |
| 32 | 151 |
| 35 | 390 |
| 38 | 632 | a.6) Thrombin Generation Assay (Thrombogram)

The effect of the test substances on the thrombogram (thrombin generation assay according to Hemker) is determined in vitro in human plasma (Octaplas® from Octapharma). In the thrombin generation assay according to Hemker, the activity of thrombin in coagulating plasma is determined by measuring the fluorescent cleavage products of the substrate I-1140 (Z-Gly-Gly-Arg-AMC, Bachem). Reagents from Thrombinoscope (PPP reagent: 30 pM recombinant tissue factor, 24 µM phospholipids in HEPES) are used to start the coagulation reaction. The reaction is carried out in the presence of varying concentrations of test substance or the corresponding solvent. Moreover, a thrombin calibrator from Thrombinoscope is used whose amidolytic activity is required for calculating the thrombin activity in a plasma sample.

The test is carried out according to the manufacturer's instructions (Thrombinoscope BV): 4 µl of the test substance or of the solvent, 76 µl of plasma and 20 µl of PPP reagent or thrombin calibrator are incubated at 37° C. for 5 min. After addition of 20 µl of 2.5 mM thrombin substrate in 20 mM Hepes, 60 mg/ml of BSA, 102 mM calcium chloride, the thrombin generation is measured every 20 s over a period of 120 min. Measurement is carried out using a fluorometer (Fluoroskan Ascent) from Thermo Electron fitted with a 390/460 nM filter pair and a dispenser. Using the thrombinoscope software, the thrombogram is calculated and presented graphically. What is calculated are the following parameters: lag time, time to peak, peak, ETP (endogenous thrombin potential) and start tail.

a.7) Determination of the Anticoagulatory Activity

The anticoagulatory activity of the test substances is determined in vitro in human plasma, rabbit plasma and rat plasma. To this end, blood is drawn off in a mixing ratio of sodium citrate/blood of 1/9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effected a doubling of the prothrombin time is determined.

The thrombin time (TT) is determined in the presence of varying concentrations of test substance or the corresponding solvent using a commercial test kit (thrombin reagent from Roche). The test compounds are incubated with the plasma at 37° C. for 3 minutes. Coagulation is then started by addition of the thrombin reagent, and the time when coagulation occurs is determined. The concentration of test substance which effects a doubling of the thrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects a doubling of the APTT is determined.

a.8) Thromboelastography (Thromboelastogram)

The thromboelastography is carried out with the aid of the thromboelastograph ROTEM from Pentapharm and its accessories, cup and pin. The measurement is carried out in whole blood drawn off beforehand into sodium citrate monovettes from Sarstedt. The blood in the monovettes is kept in motion using a shaker and preincubated at 37° C. for 30 min. A 2 molar stock solution of calcium chloride in water is prepared. This is diluted 1:10 with an aqueous 0.9% sodium chloride solution. For the measurement, 20 µl of this 200 mM calcium chloride solution are initially charged into the cups (final concentration of calcium chloride 12.5 mM). 3.2 µl of substance or solvent are added. The measurement is started by addition of 300 µl of whole blood. After the addition, using the tip of the pipette, the mixture is briefly drawn into the pipette and released again without generating air bubbles. The measurement is carried out over a period of 2.5 hours or is stopped when fibrinolysis sets in. For evaluation, the following parameters are determined: CT (clotting time/[sec.]), CFT (clotting formation time/[sec.]), MCF (maximum clot firmness/[mm]) and the alpha angle [°]. The measurement points are determined every 3 seconds and represented graphically, with the y axis for MCF [mm] and the x axis for time [sec.].

a.9) Inhibition of the Thrombus-Bound Coagulation Factors Thrombin and Factor Xa Blood clots formed either prior to initiation of therapy with anticoagulants, during therapy breaks or in spite of therapy contain large amounts of coagulation factors which may favor the progressing thrombus formation. These coagulation factors are bound firmly to the thrombus and cannot be washed out. In certain clinical situations, this may result in a risk for the patient. In the tests carried out below, both thrombin and factor Xa having biological (procoagulatory) activity can be demonstrated in human thrombi.

Thrombi Formed In Vitro

Thrombi are formed in vitro from human plasma and examined for the activity of the bound coagulation factors thrombin and factor Xa. To this end, 300 µl of plasma are mixed with 30 µl of lipid vesicles and 30 µl of an aqueous calcium chloride solution in a 48-well MTP plate and incubated for 30 min. This and the following steps are carried out at 37° C. and with constant agitation (300 rpm). The thrombi formed are transferred into a new 48-well MTP plate and washed twice with 0.9% sodium chloride solution over a period of 10 min, the thrombus being dabbed on filter paper during the washing steps. The thrombus is transferred into buffer B (Owens Veronal Buffer, 1% BSA) and incubated for 15 min, dabbed on filter paper and incubated in test substance of various concentrations in buffer B for 30 min. The clots are then washed twice as described above. The thrombi are dabbed and transferred into buffer D: (240 µl Owren's Veronal Buffer, 1% BSA and 15.6 mM calcium chloride) and incubated with or without 0.6 µM prothrombin for 45 min. The reaction is stopped by addition of 75 µl of a 1% EDTA solution. The thrombin activity is measured separately in the thrombus in buffer A (7.5 mM $Na_2EDTA\times 2H_2O$, 175 mM sodium chloride, 1% BSA, pH 8.4) or in the supernatant from the last step. To this end, the substrate I-1120 in used in a final concentration of 50 µM, and the resulting fluorescence is measured in a fluorescence plate reader (360/465 nm).

The activity of this thrombus-bound thrombin cannot be suppressed by a selective factor Xa inhibitor in therapeutically relevant concentrations. In contrast, it can be inhibited with dual factor IIa/factor Xa inhibitors or a factor IIa reference inhibitor.

After addition of prothrombin, if thrombus-bound factor Xa is present (prothrombinase complex), new thrombin is formed which is detected by the fluorescent substrate. This renewed formation of thrombin cannot be prevented by a pure thrombin inhibitor; however, it can be inhibited by dual factor IIa/factor Xa inhibitors or by the selective factor Xa reference inhibitor.

The biological activity of the thrombus-bound thrombin activity is tested by adding fluorescently labeled fibrinogen which, by active thrombin, is converted into fibrin and bound to the thrombus. To this end, the thrombus is formed as described above and incubated in 250 µl of a fibrinogen solution (100 µg/ml) labeled with Alexa488 and 30 µl of an aqueous 100 mM calcium chloride solution (with or without various concentrations of test substances). The fluorescence of the supernatant is measured in a fluorescence plate reader at a suitable wavelength. Moreover, the thrombi are washed four times for in each case 15 min and evaluated by fluorescence microscopy. The decrease of the fluorescence from the supernatant and the increase of the fluorescence of the thrombi can be inhibited by dual factor IIa/factor Xa inhibitors, but not by the factor Xa reference inhibitor.

Intracardial Thrombi Formed In Vivo (Patient Material)

The experiments are repeated with thrombi taken from the left ventricle of patients during heart surgery. To this end, the thrombi are thawed and divided into pieces (wet weight 10-100 mg). Depending on the protocol, the thrombi are used after repeated washing or without washing, and the thrombin activity is measured analogously to the method described above using the substrate I-1120 (final concentration 100 µM).

a.10) Specific Diagnosis of Impaired Coagulation and Organ Function in Endotoxemic Mice and Rats Thrombin/Antithrombin Complexes Thrombin/antithrombin complexes (hereinbelow referred to as "TAT") are a measure for the thrombin formed endogenously by coagulation activation. TAT are determined using an ELISA assay (Enzygnost TAT micro, Dade-Behring). Plasma is obtained from citrate blood by centrifugation. 50 µl of TAT sample buffer are added to 50 µl of plasma, and the sample is shaken briefly and incubated at room temperature for 15 min. The samples are filtered off with suction, and the well is washed 3 times with wash buffer (300 µl/well). During the washings, the liquid is removed by tapping the plate. Conjugate solution (100 µl) is added, and the plate is incubated at room temperature for 15 min. The samples are sucked off, and the well is washed 3 times with wash buffer (300 µl/well). Chromogenic substrate (100 µl/well) is then added, the plate is incubated in the dark at room temperature for 30 min, stop solution is added (100 µl/well) and the color development is measured at 492 nm (Saphire plate reader).

Parameters for Organ Function

Various parameters are determined which allow conclusions to be drawn with respect to a restriction of the function of various internal organs by administration of LPS and which allow the therapeutic effect of test substances to be estimated. Citrate blood or, if appropriate, lithium/heparin blood is centrifuged, and the parameters are determined from the plasma. Typically, the following parameters are determined: creatinin, urea, aspartate aminotransferase (AST), alanine aminotransferase (ALT), total bilirubin, lactate dehydrogenase (LDH), total protein, total albumin and fibrinogen. The values give indications concerning the function of the kidneys, the liver, the cardiovascular system and the blood vessels.

Parameters for Inflammation

The extent of the inflammatory reaction triggered by endotoxin can be detected by the increase of inflammation mediators, for example interleukins (1, 6, 8 and 10), tumor necrosis factor alpha or monocyte chemoattractant protein-1 in the plasma. To this end, ELISAs or the luminex system may be used.

b) Determination of the Antithrombotic Activity (In Vivo)

b.1) Arteriovenous Shunt and Hemorrhage Model (Combi-Model Rat)

Fasting male rats (strain: HSD CPB:WU) having a weight of 300-350 g are anesthetized using Inactin (150-180 mg/kg). Thrombus formation is initiated in an arteriovenous shunt in accordance with the method described by Christopher N. Berry et al., Br. J. Pharmacol. (1994), 113, 1209-1214. To this end, the left jugular vein and the right carotid artery are exposed. The two vessels are connected by an extracorporeal shunt using a polyethylene tube (PE 60) of a length of 10 cm. In the middle, this polyethylene tube is attached to a further polyethylene tube (PE 160) of a length of 3 cm which contains a roughened nylon thread arranged to form a loop, to form a thrombogenic surface. The extracorporeal circulation is maintained for 15 minutes. The shunt is then removed and the nylon thread with the thrombus is weighed immediately. The weight of the nylon thread on its own is determined before the experiment is started.

To determine the bleeding time, immediately after opening of the shunt circulation, the tip of the tail of the rats is docked by 3 mm using a razor blade. The tail is then placed into physiological saline kept at a temperature of 37° C., and the bleeding from the cut is observed over a period of 15 min. What is determined is the time until bleeding ceases for at least 30 seconds (initial bleeding time), total bleeding time over a period of 15 minutes (cumulative bleeding time) and the quantitative blood loss via photometric determination of the collected hemoglobin.

Before the extracorporeal circulation is set up and the tip of the tail is docked, the test substances are administered to the animals while awake either intravenously via the contralateral jugular vein as a single bolus or as a bolus with subsequent continuous infusion or orally using a pharyngeal tube.

c) Determination of Pharmacokinetics (In Vivo)

To determine the in vivo pharmacokinetics, the test substances are dissolved in various formulating compositions (for example plasma, ethanol, DMSO, PEG400, etc.) or mixtures of these solubilizers and administered intravenously or perorally to mice, rats, dogs or monkeys. Intravenous administration is carried out either as a bolus injection or as an infusion. The doses administered are in the range from 0.1 to 5 mg/kg. Blood samples are taken by means of a catheter or as sacrifice plasma at various times over a period of up to 26 h. Furthermore, in some cases, samples of organs, tissue and urine are also taken. Quantitative determination of the substances in the test samples takes place using calibration samples adjusted in the matrix in question. Proteins present in the samples are removed by precipitation with acetonitrile or methanol. The samples are then fractionated by HPLC using reversed-phase columns in a 2300 HTLC system (Cohesive Technologies, Franklin, Mass., USA). The HPLC system is coupled via a turbo ion spray interface to an API 3000 Triple Quadropole mass spectrometer (Applied Biosystems, Darmstadt, Germany). The plasma concentration time course is analyzed using a validated kinetic analysis program.

The affinity of a substance for a transport protein is examined by in vitro testing in a flux assay using Caco-2 cells or cells which are overexpressed in a specific transporter (Troutman M D, Thakker D R, Pharm. Res. 20 (8) 1210-1224 (2003); Schwab D, Fischer H, Tabatabaei A, Poli S, Huwyler J, J. Med. Chem. 46, 1716-1725 (2003); Merino G, Jonker J W, Wagenaar E, Pulido M M, Molina A J, Alvarez A I, Schinkel A H, Drug Metab. Dispos. 33 (5) 614-618 (2005)). To this end, the cells are cultivated on 24- or 96-well filter plates for 4 to 15 days. To determine the permeation, the substances in a HEPES buffer are added either apically (A) or basally (B) to the cells, and the mixture is incubated for 2 h. After 0 h and 2 h, samples are taken from the cis- and trans-compartments and analyzed by LC-MS/MS. The Papp value is calculated using the formula published by Schwab et al. A substance is classified as actively transported when the ratio of Papp (B–A)/Papp (A–B) is >2 or <0.5.

e) Determination of the Endotoxinemia Activity (In Vivo)

The examination is carried out using rats or mice. In the mouse model (NMRI, male), LPS (*Escherichia coli* serotype 055:B5, Sigma-Aldrich) is injected 50 mg/kg intraperitoneally. The test substances are administered up to one hour prior to the LPS injection either intravenously via the tail vein, subcutaneously, intraperitoneally or orally using a stomach tube. Four hours after the LPS administration, the animal is anesthetized (Ketavet/Rompun) and the abdomen is opened by surgery. Sodium citrate solution (3.2% w/v) (formula: body weight in g/13 times 100 µl) is injected into the lower vena cava, and a blood sample (about 1 ml) is taken after 30 sec. Various parameters, for example cellular blood components (in particular erythrocytes, leukocytes and platelets), lactate concentration, coagulation activation (TAT) or parameters of organ dysfunction or organ failure and mortality are determined from the blood.

f) Description of the Method Used for DIC Tests on Rats

LPS (*E. coli* O55 B5, manufactured by Sigma, dissolved in PBS) is administered to male Wistar rats at a dosage of 250 µg/kg intravenously into the tail vein (administration volume 2 ml/kg). The test substance is dissolved in PEG 400/H$_2$O 60%/40% and administered orally (administration volume 5 ml/kg) 30 minutes prior to the LPS injection. 1, 5 or 4 hours after the LPS injection, the animals are exsanguinated by puncture of the heart in terminal anesthesia (Trapanal® 100 mg/kg i.p.), and citrate plasma is obtained for the determination of fibrinogen, PT, TAT and platelet number. Optionally, serum is obtained for the determination of liver enzymes, kidney function parameters and cytokines. TNFα and IL-6 are determined using commercially available ELISAs (R&D Systems).

It is also possible to measure direct parameters of organ function, for example left- and right-ventricular pressures, arterial pressures, urine excretion, kidney perfusion and blood gases and acid/base state.

C. Exemplary Embodiments Of Pharmaceutical Compositions

The inventive compounds can be converted into pharmaceutical preparations in the following ways:

Tablet:

Composition:

100 mg of the inventive compound, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Preparation:

The mixture of the inventive compound, lactose and starch is granulated with a 5% solution (m/m) of PVP in water. The granules are dried and then mixed with the magnesium stearate for 5 minutes. This mixture is compressed using a conventional tablet press (see above for format of the tablet). As guideline, a compressive force of 15 kN is used for the compression.

Oral Suspension:

Composition:

1000 mg of the inventive compound, 1000 mg of ethanol (96%), 400 mg of Rhodigel® (xanthan gum from FMC, Pennsylvania, USA) and 99 g of water.

10 ml of oral suspension are equivalent to a single dose of 100 mg of the inventive compound.

Preparation:

The Rhodigel is suspended in ethanol, and the inventive compound is added to the suspension. The water is added while stirring. The mixture is stirred for about 6 h until the swelling of the Rhodigel is complete.

Oral Solution:

Composition:

500 mg of the inventive compound, 2.5 g of polysorbate and 97 g of polyethylene glycol 400. 20 g of oral solution are equivalent to a single dose of 100 mg of the inventive compound.

Production:

The inventive compound is suspended in the mixture of polyethylene glycol and polysorbate while stirring. Stirring is continued until the inventive compound is completely dissolved.

i.v. Solution:

The inventive compound is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

The invention claimed is:

1. A compound of the formula

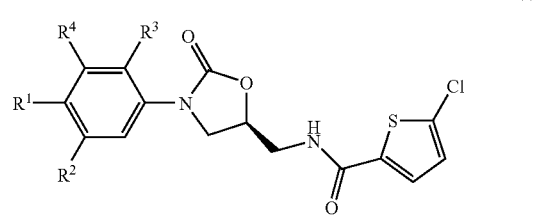

in which
R$^1$ is a group of the formula

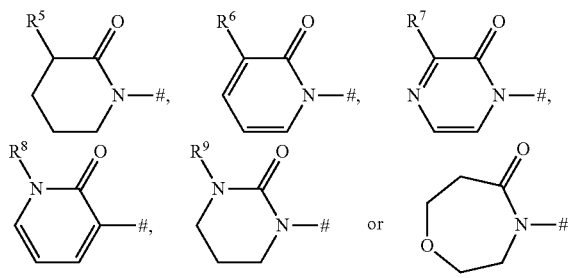

where
# is the attachment site to the phenyl ring,
R$^5$ is hydrogen or C$_1$-C$_3$-alkyl,
in which alkyl may be substituted by a hydroxyl substituent,
R$^6$ is hydrogen, trifluoromethyl, trifluoromethoxy, difluoromethoxy, C$_1$-C$_3$-alkyl or C$_1$-C$_4$-alkoxy,
in which alkoxy may be substituted by a substituent, which substituent is selected from the group consisting of halogen, hydroxy, trifluoromethyl, aminocarbonyl, C$_1$-C$_3$-alkoxy, C$_1$-C$_3$-alkylcarbonyl, C$_1$-C$_4$-alkylaminocarbonyl and morpholinocarbonyl,
R$^7$ is hydrogen, C$_1$-C$_3$-alkyl or C$_1$-C$_4$-alkoxy,
in which C$_2$-C$_3$-alkyl and C$_2$-C$_4$-alkoxy may be substituted by a hydroxyl substituent,
R$^8$ is hydrogen or C$_1$-C$_3$-alkyl,
in which C$_2$-C$_3$-alkyl may be substituted by a hydroxyl substituent,
R$^9$ is hydrogen or C$_1$-C$_3$-alkyl,
in which C$_2$-C$_3$-alkyl may be substituted by a hydroxyl substituent,
R$^2$ is chlorine, trifluoromethyl, trifluoromethoxy, difluoromethoxy, methyl, ethyl, n-propyl, isopropyl, methoxy, ethoxy, methoxymethyl, ethoxymethyl or cyclopropyl,
R$^3$ is hydrogen, C$_1$-C$_3$-alkoxy or C$_1$-C$_3$-alkylamino,
R$^4$ is hydrogen or methyl,
or a pharmaceutically acceptable salt thereof.

2. A compound as claimed in claim 1, characterized in that R$^1$ is a group of the formula

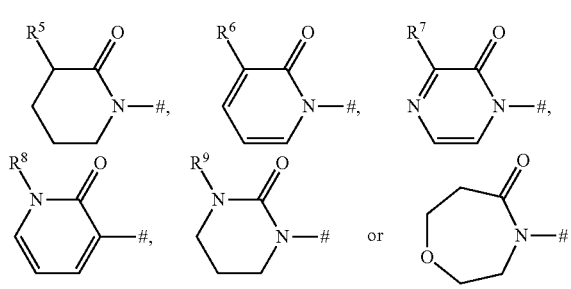

where
# is the attachment site to the phenyl ring,
R$^5$ is hydrogen or C$_1$-C$_3$-alkyl,
in which alkyl may be substituted by a hydroxyl substituent,
R$^6$ is hydrogen, trifluoromethyl, trifluoromethoxy, C$_1$-C$_3$-alkyl or C$_1$-C$_4$-alkoxy,
in which alkoxy may be substituted by a substituent, which substituent is selected from the group consisting of halogen, hydroxy, trifluoromethyl, aminocarbonyl, C$_1$-C$_3$-alkoxy, C$_1$-C$_3$-alkylcarbonyl, C$_1$-C$_4$-alkylaminocarbonyl and morpholinocarbonyl,
R$^7$ is C$_1$-C$_4$-alkoxy,
R$^8$ is C$_1$-C$_3$-alkyl,
R$^9$ is hydrogen or C$_1$-C$_3$-alkyl,
in which C$_2$-C$_3$-alkyl may be substituted by a hydroxyl substituent,
R$^2$ is chlorine, trifluoromethyl, methyl, ethyl, n-propyl, isopropyl, methoxy, ethoxy, methoxymethyl, ethoxyethyl or cyclopropyl,
R$^3$ is hydrogen, C$_1$-C$_3$-alkoxy or C$_1$-C$_3$-alkylamino, and
R$^4$ is hydrogen or methyl,
or a pharmaceutically acceptable salt thereof.

3. A compound as claimed in claim 1, characterized in that R$^1$ is a group of the formula

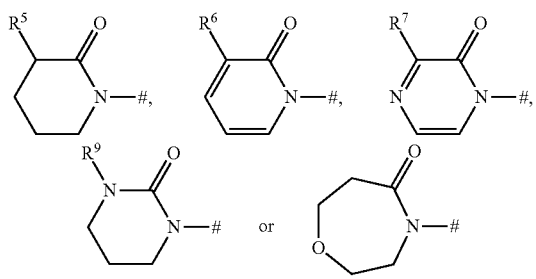

where
# is the attachment site to the phenyl ring,
R$^5$ is hydrogen or C$_1$-C$_3$-alkyl,
in which alkyl may be substituted by a hydroxyl substituent,
R$^6$ is hydrogen, trifluoromethyl, trifluoromethoxy, C$_1$-C$_3$-alkyl or C$_1$-C$_4$-alkoxy,
in which alkoxy may be substituted by a substituent, which substituent is selected from the group consisting of halogen, hydroxy, trifluoromethyl, aminocarbonyl, C$_1$-C$_3$-alkoxy, C$_1$-C$_3$-alkylcarbonyl, C$_1$-C$_4$-alkylaminocarbonyl and morpholinocarbonyl,
R$^7$ is C$_1$-C$_4$-alkoxy,
R$^9$ is hydrogen or C$_1$-C$_3$-alkyl,
in which C$_2$-C$_3$-alkyl may be substituted by a hydroxyl substituent,
R$^2$ is chlorine, trifluoromethyl, methyl, ethyl, n-propyl, isopropyl, methoxy, ethoxy, methoxymethyl, ethoxyethyl or cyclopropyl,
R$^3$ is hydrogen, C$_1$-C$_3$-alkoxy or C$_1$-C$_3$-alkylamino, and
R$^4$ is hydrogen or methyl,
or a pharmaceutically acceptable salt thereof.

4. A compound as claimed in claim 1, characterized in that R$^1$ is a group of the formula

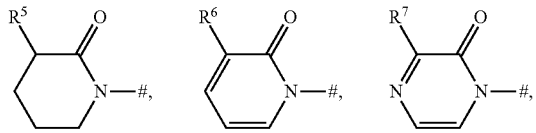

-continued

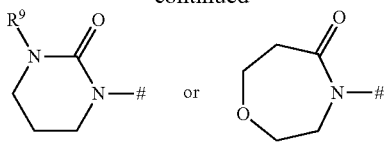

where
# is the attachment site to the phenyl ring,
$R^5$ is hydrogen,
$R^6$ is hydrogen or $C_1$-$C_4$-alkoxy,
in which alkoxy may be substituted by a hydroxyl substituent,
$R^7$ is ethoxy,
$R^9$ is hydrogen, methyl or 2-hydroxyeth-1-yl,
$R^2$ is methyl, isopropyl, methoxy, ethoxy, methoxymethyl or cyclopropyl,
$R^3$ is hydrogen, and
$R^4$ is hydrogen or methyl,
or a pharmaceutically acceptable salt thereof.

5. A process for preparing a compound of the formula (I) or a pharmaceutically acceptable salt thereof as claimed in claim 1, characterized in that

[A] the compound of the formula

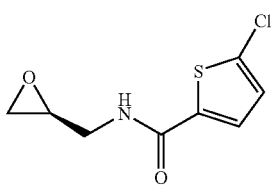

(II)

is reacted in the first stage with a compound of the formula

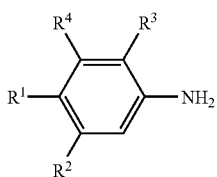

(III)

in which $R^1$, $R^2$, $R^3$ and $R^4$ are each as defined in claim 1 to give a compound of the formula

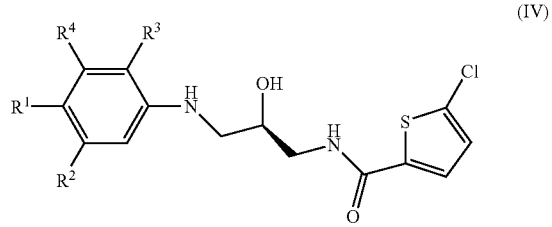

(IV)

in which $R^1$, $R^2$, $R^3$ and $R^4$ are each as defined in claim 1,
and, in the second stage, in the presence of phosgene or phosgene equivalents, the latter is cyclized to a compound of the formula (I),
or
[B] a compound of the formula

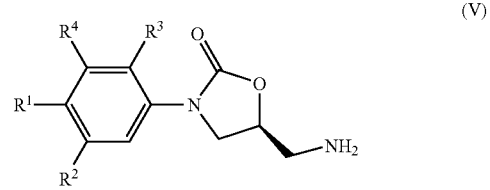

(V)

in which $R^1$, $R^2$, $R^3$ and $R^4$ are each as defined in claim 1
is reacted with a compound of the formula

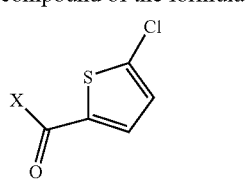

(VI)

in which
X is halogen or hydroxy.

6. A pharmaceutical composition comprising a compound as claimed in claim 1 in combination with an inert nontoxic pharmaceutically suitable excipient.

7. A method for treatment and/or prophylaxis of thromboembolic disorders in humans and animals using an anticoagulatory amount of at least one compound as claimed in claim 1.

8. A method for preventing blood coagulation in vitro, characterized in that an anticoagulatory amount of a compound as claimed in claim 1 is added.

* * * * *